US012202900B2

(12) United States Patent
De Haard et al.

(10) Patent No.: US 12,202,900 B2
(45) Date of Patent: Jan. 21, 2025

(54) COMPOSITIONS AND METHODS FOR TREATING IMMUNE THROMBOCYTOPENIA

(71) Applicant: argenx BV, Ghent (BE)

(72) Inventors: Hans De Haard, Oudelande (NL); Peter Ulrichts, Destelbergen (BE); Thierry Cousin, Bordeaux (FR); Nicolas Leupin, Zurich (CH); Torsten Dreier, Sint Martens Latem (BE); Tonke Van Bragt, Boxtel (NL)

(73) Assignee: argenx BV, Ghent (BE)

( * ) Notice: Subject to any disclaimer, the term of this patent is extended or adjusted under 35 U.S.C. 154(b) by 682 days.

(21) Appl. No.: 16/435,166

(22) Filed: Jun. 7, 2019

(65) Prior Publication Data

US 2020/0024344 A1    Jan. 23, 2020

Related U.S. Application Data

(60) Provisional application No. 62/732,414, filed on Sep. 17, 2018, provisional application No. 62/731,947, filed on Sep. 16, 2018, provisional application No. 62/682,805, filed on Jun. 8, 2018.

(51) Int. Cl.
*C07K 16/28* (2006.01)
*C07K 14/47* (2006.01)
*A61K 45/06* (2006.01)

(52) U.S. Cl.
CPC ........ *C07K 16/283* (2013.01); *C07K 14/4703* (2013.01); *A61K 45/06* (2013.01); *C07K 2317/41* (2013.01); *C07K 2317/52* (2013.01)

(58) Field of Classification Search
None
See application file for complete search history.

(56) References Cited

U.S. PATENT DOCUMENTS

| | | |
|---|---|---|
| 5,326,856 A | 7/1994 | Coughlin et al. |
| 5,624,821 A | 4/1997 | Winter et al. |
| 5,648,260 A | 7/1997 | Winter et al. |
| 5,677,425 A | 10/1997 | Bodmer et al. |
| 5,869,046 A | 2/1999 | Presta et al. |
| 5,885,573 A | 3/1999 | Bluestone et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,528,624 B1 | 3/2003 | Idusogie et al. |
| 6,737,056 B1 | 5/2004 | Presta et al. |
| 6,795,661 B2 | 9/2004 | Dall'Acqua et al. |
| 6,821,505 B2 | 11/2004 | Ward |
| 6,992,234 B2 | 1/2006 | Roopenian et al. |
| 7,083,784 B2 | 8/2006 | Dall'Acqua et al. |
| 7,183,387 B1 | 2/2007 | Presta |
| 7,670,600 B2 | 3/2010 | Dall'Acqua et al. |
| 7,683,784 B2 | 3/2010 | Nagai et al. |
| 7,704,497 B2 | 4/2010 | Dall'Acqua et al. |
| 8,012,476 B2 | 9/2011 | Dall'Acqua et al. |
| 8,021,856 B2 | 9/2011 | Umaña et al. |
| 8,067,232 B2 | 11/2011 | Kanda |
| 8,101,186 B2 | 1/2012 | Mezo et al. |
| 8,163,881 B2 | 4/2012 | Ober et al. |
| 8,195,661 B2 | 6/2012 | Asawaree |
| 8,216,805 B2 | 7/2012 | Carter et al. |
| 8,273,351 B2 | 9/2012 | Tenhoor et al. |
| 8,323,962 B2 | 12/2012 | Dall'Acqua et al. |
| 8,475,792 B2 | 7/2013 | Dall'Acqua et al. |
| 8,680,237 B2 | 3/2014 | Strome et al. |
| 8,795,661 B2 | 8/2014 | Dall'Acqua et al. |
| 8,815,246 B2 | 8/2014 | Tenhoor et al. |
| 8,834,871 B2 | 9/2014 | Ober |
| 9,260,520 B2 | 2/2016 | Tenhoor et al. |
| 10,316,073 B2 | 6/2019 | Ulrichts |
| 11,505,585 B2 | 11/2022 | Ulrichts et al. |
| 11,591,388 B2 | 2/2023 | Borgions et al. |
| 2004/0002587 A1 | 1/2004 | Watkins et al. |
| 2004/0010124 A1 | 1/2004 | Johnson et al. |
| 2004/0047862 A1 | 3/2004 | Lazarus et al. |

(Continued)

FOREIGN PATENT DOCUMENTS

| | | |
|---|---|---|
| EP | 0227110 A2 | 7/1987 |
| EP | 0904107 B1 | 3/1999 |

(Continued)

OTHER PUBLICATIONS

Newland, Adrian C et al. American journal of hematology vol. 95,2 (2020): 178-187. doi:10.1002/ajh.25680 (Year: 2020).*
Khan, Ayesha M et al. P & T: a peer-reviewed journal for formulary management vol. 42, 12 (2017): 756-763 (Year: 2017).*
Janeway, Charles A. "Immunobiology: the Immune System in Health and Disease." 2005 (Year: 2005).*
Robak, Tadeusz, et al. Blood 130.Supplement 1 (2017): 15-15 (Year: 2017).*
Bussel, James B., et al. New England Journal of Medicine 357.22 (2007): 2237-2247 (Year: 2007).*
(Robak, Tadeusz, et al Hematology 15.5 (2010): 351-359) (Year: 2010).*
Michael F. Halle, Pharmaceutical Technology, Advanstar Communications Inc. Oct. 2, 2007, vol. 31, Issue 10 (Year: 2007).*
Broome C. et al, "Efficacy and Safety of Efgartigimod PH20 Subcutaneous in Adult Patients with Primary Immune Thrombocytopenia: Advance SC, a Global Phase 3 Clinical Trial in Progress" [abstract]. Res Pract Thromb Haemost. 2021; 5 (Suppl 2) (Year: 2021).*

(Continued)

*Primary Examiner* — Michael Szperka
*Assistant Examiner* — Lia E Taylor
(74) *Attorney, Agent, or Firm* — Dechert LLP; Andrew T. Wilkins; Sharla F. Flohr

(57) ABSTRACT

A method is disclosed for the treatment of human subjects diagnosed with immune thrombocytopenia (ITP). The method comprises administering to a human subject a human neonatal Fc receptor (hFcRn) antagonist, optionally in combination with standard-of-care ITP treatment. In certain embodiments, the hFcRn antagonist is efgartigimod (ARGX-113). Standard-of-care ITP treatment may comprise administration of corticosteroids, immunosuppressants, and/ or thrombopoietin receptor (TPO-R) agonists.

14 Claims, 13 Drawing Sheets

Specification includes a Sequence Listing.

(56) References Cited

U.S. PATENT DOCUMENTS

| | | |
|---|---|---|
| 2004/0265321 A1 | 12/2004 | Johnson et al. |
| 2005/0053598 A1 | 3/2005 | Burke et al. |
| 2006/0210557 A1* | 9/2006 | Luisi .................. A61K 31/4172 514/400 |
| 2007/0041907 A1 | 2/2007 | Ober |
| 2007/0092507 A1 | 4/2007 | Balthasar et al. |
| 2009/0252729 A1 | 10/2009 | Farrington et al. |
| 2011/0066111 A1 | 3/2011 | Teschner et al. |
| 2011/0081345 A1 | 4/2011 | Moore |
| 2011/0243966 A1 | 10/2011 | Farrington et al. |
| 2012/0219551 A1 | 8/2012 | Johnson |
| 2013/0142802 A1 | 6/2013 | Chang et al. |
| 2014/0302028 A1 | 10/2014 | Zha et al. |
| 2015/0218239 A1* | 8/2015 | Ulrichts .................. A61P 25/00 424/133.1 |
| 2016/0264669 A1 | 9/2016 | Ulrichts et al. |
| 2019/0194277 A1 | 6/2019 | de Haard et al. |
| 2021/0236596 A1 | 8/2021 | Verheesen et al. |
| 2022/0275035 A1 | 9/2022 | Ulrichts et al. |
| 2023/0357382 A1 | 11/2023 | Borgions et al. |

FOREIGN PATENT DOCUMENTS

| | | |
|---|---|---|
| EP | 1355919 B1 | 11/2010 |
| EP | 1896503 B1 | 10/2014 |
| JP | 2013-507128 A | 3/2013 |
| WO | WO 1994/029351 A2 | 12/1994 |
| WO | WO 1996/022024 A1 | 7/1996 |
| WO | WO 1997/034631 A1 | 9/1997 |
| WO | WO 1999/004813 A1 | 2/1999 |
| WO | WO 1999/058572 A1 | 11/1999 |
| WO | WO 2000/042072 A2 | 7/2000 |
| WO | WO 2001/058957 A2 | 8/2001 |
| WO | WO 2002/043658 A2 | 6/2002 |
| WO | WO 2002/060919 A2 | 8/2002 |
| WO | WO 2004/016750 A2 | 2/2004 |
| WO | WO 2004/029207 A2 | 4/2004 |
| WO | WO 2004/035752 A2 | 4/2004 |
| WO | WO 2004/063343 A2 | 7/2004 |
| WO | WO 2004/063351 A2 | 7/2004 |
| WO | WO 2004/099249 A2 | 11/2004 |
| WO | WO 2005/040217 A2 | 5/2005 |
| WO | WO 2006/118772 A2 | 11/2006 |
| WO | WO 2006/130834 A2 | 12/2006 |
| WO | WO 2007/098420 A2 | 8/2007 |
| WO | WO 2009/100105 A2 | 8/2009 |
| WO | WO 2009/131702 A2 | 10/2009 |
| WO | WO 2010/014909 A1 | 2/2010 |
| WO | WO 2010/106180 A2 | 9/2010 |
| WO | WO2010111254 A1 | 9/2010 |
| WO | WO 2011/044368 A1 | 4/2011 |
| WO | WO2011080209 A2 | 7/2011 |
| WO | WO2012167039 A1 | 12/2012 |
| WO | WO 2013/000702 A1 | 1/2013 |
| WO | WO 2013/063186 A1 | 5/2013 |
| WO | WO 2013/074598 A1 | 5/2013 |
| WO | WO 2013/100702 A1 | 7/2013 |
| WO | 2013166604 A1 | 11/2013 |
| WO | WO 2014/008391 A1 | 1/2014 |
| WO | WO 2014/019727 A1 | 2/2014 |
| WO | 2014140366 A1 | 9/2014 |
| WO | WO 2014/204280 A1 | 12/2014 |
| WO | 2015071330 A1 | 5/2015 |
| WO | 2015073721 A1 | 5/2015 |
| WO | WO 2015/081073 A2 | 6/2015 |
| WO | WO 2015/100299 A1 | 7/2015 |
| WO | WO 2016/042083 A1 | 3/2016 |
| WO | WO 2016/123521 A2 | 8/2016 |
| WO | WO 2016/142782 A1 | 9/2016 |
| WO | WO 2016/180765 A1 | 11/2016 |
| WO | WO 2016/183352 A1 | 11/2016 |
| WO | WO 2017/012959 A1 | 1/2017 |
| WO | WO 2017/121330 A1 | 7/2017 |
| WO | 2017189959 A1 | 11/2017 |
| WO | 2018023136 A1 | 2/2018 |
| WO | WO 2018/083122 A1 | 5/2018 |
| WO | WO 2019/110823 A1 | 6/2019 |
| WO | WO2019118791 A1 | 6/2019 |
| WO | WO 2019/234713 A2 | 12/2019 |
| WO | 2020078905 A1 | 4/2020 |
| WO | WO2020097099 A1 | 5/2020 |
| WO | 2020227515 A1 | 11/2020 |
| WO | WO 2020/236695 A1 | 11/2020 |
| WO | 2020245420 A1 | 12/2020 |
| WO | 2021022249 A1 | 2/2021 |
| WO | 2020245420 A9 | 4/2021 |
| WO | 2021140202 A1 | 7/2021 |
| WO | 2021216756 A1 | 10/2021 |
| WO | 2022098955 A1 | 5/2022 |
| WO | 2023012515 A2 | 2/2023 |
| WO | 2023135321 A1 | 7/2023 |
| WO | 2023156614 A1 | 8/2023 |
| WO | 2023209036 A1 | 11/2023 |
| WO | 2023242361 A1 | 12/2023 |
| WO | 2023242362 A1 | 12/2023 |
| WO | 2023242371 A1 | 12/2023 |
| WO | 2023242372 A1 | 12/2023 |
| WO | 2024100453 A1 | 5/2024 |
| WO | 2024100455 A1 | 5/2024 |
| WO | 2024105445 A2 | 5/2024 |
| WO | 2024147074 A1 | 7/2024 |
| WO | 2024150073 A1 | 7/2024 |

OTHER PUBLICATIONS

Abdiche et al. (2015) "The neonatal Fc receptor (FcRn) binds independently to both sites of the IgG homodimer with identical affinity," mAbs, 7(2):331-343.

Akilesh et al. (2004) "The MHC class I-like Fc receptor promotes humorally mediated autoimmune disease," J. Clin. Invest. 113(9):1328-1333.

Alegre et al. (1994) "A Non-Activating "Humanized" Anti-CD3 Monoclonal Antibody Retains Immunosuppressive Properties in Vivo," Transplantation, 57(11):1537-1543.

Alipour-Faz et al. (2017) "A comparison between IVIG and plasma exchange as preparations before thymectomy in myasthenia gravis patients," Acta Neurol Belg, 117:245-249.

Andersen et al. (2012) "Structure-based mutagenesis reveals the albumin-binding site of the neonatal Fc receptor," Nat. Commun. 3:610. pp. 1-9.

Anonymous (2016) "argenx announces initial results from Phase 1 multiple ascending dose (MAD) study of ARGX-113 in healthy volunteers—Argenx," 1 pg.

Argen-X "ARGX-113," http://www.argen-x.com. Accessible on the Internet at URL: http://www.argen-x.com/en-GB/content/argx-113/22. [Last Accessed Jul. 5, 2017].

Argen-X (Oct. 2013) "An Emerging Antibody Force: Company Presentation," Presentation Slides.

Argen-X (Oct. 2013) "ARGX-113: Development Opportunity in Autoimmunity," Presentation Slides.

Argen-X N.V. (Apr. 24, 2014) "arGEN-X advances ARGX-113 into preclinical development for autoimmune disorders," Press Release. arGEN-X. Accessible on the Internet at URL: http://www.argen-x.com/en-GB/news-internal/argen-x-advances-argx-113-into-preclinical-devlopment-for-autoimmune-disorders/60. [Last Accessed Aug. 1, 2016].

Argen-X N.V. (Aug. 19, 2014) "arGEN-X announces positive preclinical results for ARGX-113," Press Release. Euronext. Accessible on the Internet at URL: https://www.euronext.com/nl/node/506652. [Last Accessed Aug. 1, 2016].

Argen-X N.V. (Jun. 20, 2014) Prospectus for Public Offering of arGEN-X N.V.

Armour et al. (1999) "Recombinant human IgG molecules lacking Fcgamma receptor I binding and monocyte triggering activities," Eur. J. Immunol. 29:2613-2624.

Ballow (1991) "Mechanism of action of IVIG therapy and potential uses in autoimmune connective tissue diseases," Cancer 68:1430-1436.

(56) References Cited

OTHER PUBLICATIONS

Barth et al. (2011) "Comparison of IVIg and Plex in patients with myasthenia gravis," Neurology. 76(23):2017-2023.
Blanchette et al. (1984) "Intensive plasma exchange therapy in ten patients with idiopathic thrombocytopenia purpura," Transfusion. 24(5):388-394.
Burns (2012) "Of Mice and Children: Lessons From a Kawasaki Mouse Model," Circulation. 125:1480-1481.
Burns et al. (2010) "History of outcome measures for myasthenia gravis," Muscle Nerve. 42(1):5-13.
Challa (2013) "Autoantibody depletion ameliorates disease in murine experimental autoimmune encephalomyelitis," mAbs, 5(5):655-659.
Chaudhury et al. (2003) "The major histocompatibility complex-related Fc receptor for IgG (FcRn) binds albumin and prolongs its lifespan," J. Exp. Med. 197(3):315-322.
Cipriani et al. (2009) "Met as a target for treatment of chest tumor," Lung Cancer. 63(2):169-179.
Clarkson et al. (1986) "Treatment of Refractory Immune Thrombocytopenic Purpura with an Anti-Fcgamma-Receptor Antibody," New England Journal of Medicine. 314(9):1236-1239.
Coetzee et al. (2000) "The Effect of Monoclonal Anti-human-platelet Antibodies on Platelet Kinetics in a Baboon Model: IgG Subclass Dependency," Thromb. Haemost. 83:148-156.
Crow et al. (2008) "The Mechanisms of Action of Intravenous Immunoglobulin and Polyclonal Anti-D Immunoglobulin in the Amelioration of Immune Thrombocytopenia Purpura: What Do We Really Know?" Transfusion Medicine Reviews. 22:103-116.
Crow et al. (2011) "The neonatal Fc receptor (FcRn) is not required for IVIg or anti-CD44 monoclonal antibody-mediated amelioration of murine immune thrombocytopenia," Blood. 118:6403-6406.
Darabi et al. (2006) "Current usage of intravenous immune globulin and the rationale behind it: the Massachusetts General Hospital data and a review of the literature," Transfusion. 46(5):741-753.
Debre et al. (1993) "Infusion of Fc gamma fragments for treatment of children with acute immune thrombocytopenia purpura," Lancet. 342(8877):945-949.
Deng et al. (2007) "Pharmacokinetic/pharmacodynamic modeling of IVIG effects in a murine model of immune thrombocytopenia," J. Pharm. Sci. 96(6):1625-1637.
Duncan et al. (1988) "Localization of the binding site for the human high-affinity Fc receptor on IgG," Nature, 332:563-564.
Edelman et al. (1969) "The covalent structure of an entire gammaG immunoglobulin molecule," the Journal of Immunology, 63:5335-5342.
El-Salem et al. (2014) "Treatment of MuSK-Associated Myasthenia Gravis," Curr. Treat. Options Neurol., 16:283, 17 pages.
Eymard et al. (2009) "[Antibodies in myasthenia gravis]," Rev. Neurol. (Paris). 165(2):137-143.
Federico et al. (2000) "Multifocal motor neuropathy improved by IVIg: randomized, double-blind, placebo-controlled study," Neurology. 55:1256-1262.
Flaherty et al. (Oct. 24, 2011) "Nonclinical evaluation of GMA161—an antihuman CD16 (Form) monoclonal antibody for treatment of autoimmune disorders in CD16 transgenic mice," Toxicological Sciences. 125(1):299-309.
Frusho et al. (1984) "High-dose intravenous gammaglobulin for Kawasaki disease," Lancet. 2:1055-1058.
Gan et al. (2009) "Analyses of the recycling receptor, FcRn, in live cells reveal novel pathways for lysosomal delivery," Traffic. 10:600-614.
Garcia et al. (2001) "Kinetics and thermodynamics of T cell receptor-autoantigen interactions in murine experimental autoimmune encephalomyelitis," Proc. Natl. Acad. Sci. USA. 98:6818-6823.
Genbank Database [online] (Jul. 2, 2016) "*Homo sapiens* Fc fragment of IgG receptor IIIa (FCGR3A), transcript variant 1, mRNA," Accession No. NM_000569. Accessible on the Internet at URL: http://www.ncbi.nlm.nih.gov/nuccore/NM_000569. [Last Accessed Aug. 19, 2016].
Ghetie et al. (1996) "Abnormally short serum half lives of IgGs in beta2-microglobulin deficient mice," Eur. J. Immunol. 26:690-696.
Ghetie et al. (1997) "Increasing the serum persistence of an IgG fragment by random mutagenesis," Nature Biotech. 15:637-640.
Ghetie et al. (2002) "Transcytosis and catabolismof antibody," Immunol. Res. 25(2):97-113.
Gilhus et al. (2011) "Myasthenia Gravis: a Review of Available Treatment Approaches," Autoimmune Diseases, Article ID 847393, 6 pages.
Grau (Sep. 21, 2011) "IgG core a-fucosylation and its impact on FcγRIIIa binding," Roche Glycart AG. In; MipTec 2011, Basel, Switzerland.
Grevys et al. (Apr. 22, 2015) "Fc Engineering of Human IgG1 for Altered Binding to the Neonatal Fc Receptor Affects Fc Effector Functions," J Immunol. 194(11):5497-5508.
Guptill et al. (Aug. 11, 2016) "Effect of therapeutic plasma exchange on immunoglobulins in myasthenia gravis," Autoimmunity. 49(7):472-479.
Hansen et al. (2002) "Intravenous Immunoglobulin Mediates an Increase in Anti-Platelet Antibody Clearance via the FcRn Receptor," Thromb. Haemost. 88:898-899.
Hanson (2014) "The role of the immunoglobulin G1 Fc N-glycan in FcγRIIIa affinity," Thesis for partial fulfillment of the degree of Master of Science. Iowa State University. Paper 14135.
Howard et al. (Apr. 30, 2013) "A randomized, double-blind, placebo-controlled phase II study of eculizumab in patients with refractory generalized myasthenia gravis," Muscle Nerve. 48(1):76-84.
Huang et al. (2005) "The central residues of a T cell receptor sequence motif are key determinants of autoantigen recognition in murine experimental autoimmune encephalomyelitis," Eur. J. Immunol. 35:299-304.
Hutchins et al. (1995) "Improved biodistribution, tumor targeting, and reduced immunogenicity in mice with a gamma4 variant of Campath-1H," Proc. Natl. Acad. Sci., USA, 92:11980-11984.
Idusogie et al. (2000) "Mapping of the C1q Binding Site on Rituxan, a Chimeric Antibody with a Human IgG1 Fc," J. Immunol., 164:4178-4184.
Idusogie et al. (2001) "Engineered Antibodies with Increased Activity to Recruit Complement," J. Immunol., 166:2571-2575.
Imbach et al. (1981) "High-dose intravenous gammaglobulin for idiopathic thrombocytopenia purpura in childhood," The Lancet, 1228-1231.
Imbach et al. (1985) "Intravenous immunoglobulin versus oral corticosteroids in acute immune thrombocytopenia purpura in childhood," The Lancet, 464-468.
Imbach et al. (2009) "Intravenous immunoglobulins induce potentially synergistic immunomodulations in autoimmune disorders," Vox Sanguinis, 10 pages.
Imbach, Paul (2012) "Treatment of immune thrombocytopenia with intravenous immunoglobulin and insights for other diseases," Swiss Medical Weekly, 10 pages.
International Preliminary Report on Patentability corresponding to International Patent Application No. PCT/EP2013/068399, issued Mar. 10, 2015.
International Preliminary Report on Patentability corresponding to International Patent Application No. PCT/US2014/072087, issued Jun. 28, 2016.
International Search Report and Written Opinion corresponding to International Patent Application PCT/EP2017/077966, mailed Jan. 29, 2018.
International Search Report corresponding to International Patent Application No. PCT/EP2013/068399, mailed Apr. 9, 2014.
International Search Report with Written Opinion corresponding to International Patent Application No. PCT/US2014/072087, mailed May 12, 2015.
International Search Report with Written Opinion corresponding to International Patent Application No. PCT/EP2018/084034, mailed Feb. 18, 2019.
Jacob et al. (2012) "Presence and Pathogenic Relevance of Antibodies to Clustered Acetylcholine Receptor in Ocular and Generalized Myasthenia Gravis," Arch Neurol., 69(8):994-1001.

(56) References Cited

OTHER PUBLICATIONS

Jain et al. (Aug. 20, 2012) "Fully recombinant IgG2a Fc multimers (stradomers) effectively treat collagen-induced arthritis and prevent idiopathic thrombocytopenia purpura in mice," Arthritis Research & Therapy 14:R192. pp. 1-12.
Jefferis et al. (1995) "Recognition sites on human IgG for Fcgamma receptors: the role of glycosylation," Immunology Letters, 44:111-117.
Jefferis et al. (1996) "Modulation of Fc(gamma)R and human complement activation by IgG3-core oligosaccharide interactions," Immunol. Lett. 54:101-104.
Jefferis et al. (2002) "Interaction sites on human IgG-Fc for FcgammaR: current models," Immunology Letters, 82:57-65.
Junghans (1997) "Finally! The Brambell receptor (FcRB). Mediator of transmission of immunity and protection from catabolismfor IgG," Immunologic Research. 16(1):29-57.
Junghans et al. (1996) "The protection receptor for IgG catabolismis the beta2-microglobulin-containing neonatal intestinal transport receptor," Proc. Natl. Acad. Sci. USA. 93:5512-5516.
Kanda et al. (2006) "Comparison of biological activity among nonfucosylated therapeutic IgG1 antibodies with three different N-linked Fc oligosaccharides: the high-mannose, hybrid, and complex types," Glycobiol. 17(1):104-118.
Kim et al. (1999) "Mapping of the site on human IgG1 for binding of the MHC class I related receptor, FcRn," Eur. J. Immunol. 29:2819-2825.
Law et al. (1997) "High-dose intravenous immune globulin and the response to splenectomy in patients with idiopathic thrombocytopenia purpura," N. Engl. J. Med. 336:1494-1498.
Li et al. (2005) "Complete FcRn dependence for intravenous Ig therapy in autoimmune skin blistering diseases," J. Clin. Invest. 115(12):3440-3450.
Liu et al. (2007) "Amelioration of experimental autoimmune myasthenia gravis in rats by neonatal FcR blockade," J. Immunol. 178(8):5390-5398.
Liu et al. (2009) "Comparing the Autoantibody Levels and Clinical Efficacy of Double Filtration Plasmapheresis, Immunoadsorption, and Intravenous Immunoglobulin for the Treatment of Late-Onset Myasthenia Gravis," Therapeutic Apheresis and Dialysis, 14(2):153-160.
Low et al. (2009) "Inhibitors of the FcRn:IgG Protein-Protein Interaction," AAPS Journal. 11(3):432-434.
Lund et al. (1991) "Human Fc gamma RI and Fc gamma RII interact with distinct but overlapping sites on human IgG," J. Immunol. 147:2657-2662.
Lund et al. (1992) "Multiple binding sites on the CH2 Domain of IgG for Mouse FcgammaRII," Molecular Immunology, 29(1):53-59.
Lund et al. (1995) "Oligosaccharide-protein interactions in IgG can modulate recognition by Fcgamma receptors," The FASEB Journal 9:115-119.
Lund et al. (1996) "Multiple interactions of IgG with its core oligosaccharide can modulate recognition by complement and human Fc gamma receptor I and influence the synthesis of its oligosaccharide chains," J. Immunol. 157:4963-4969.
Lutterbach et al. (2007) "Lung cancer cell lines harboring MET gene amplification are dependent on Met for growth and survival," Cancer Research. 67(5):2081-2088.
MacCallum et al. (1996) "Antibody-antigen Interactions: Contact Analysis and Binding Site Topography," J. Mol. Biol., 262:732-745.
Martin et al. (2001) "Crystal Structure at 2.8 A of an FcRn/Heterodimeric Fc Complex Mechanism of pH-Dependent Binding," Molecular Cell, 7:867-877.
Massachusetts General Hospital (Dec. 10, 2012) "Suppremol's Sm101 shows a sustained clinical activity and a favorable safety profile in primary immune thrombocytopenia (ITP) patients," Press Release. Evaluate Ltd.
Medesan et al. (1997) "Delineation of the amino acid residues involved in transcytosis and catabolism of mouse IgG," J. Immunol. 158:2211-2217.

Mendell et al. (2001) "Randomized controlled trial of IVIg in untreated chronic inflammatory demyelinating polyradiculoneuropathy," Neurology. 56:445-449.
Meriggioli et al. (2009) "Autoimmune myasthenia gravis: emerging clinical and biological heterogeneity," Lancet Neurol. 8:475-490.
Mezo et al. (2008) "Reduction of IgG in nonhuman primates by a peptide antagonist of the neonatal Fc receptor FcRn," Proc. Natl. Acad. Sci. USA. 105(7):2337-2342.
Mi et al. (2008) "Targeting the neonatal Fc receptor for antigen delivery using engineered Fc fragments," J. Immunol. 181:7550-7561.
Mohamed et al. (Jan. 7, 2013) "Massive intravascular haemolysis after high dose intravenous immunoglobulin therapy," British Journal of Haematology. 160:570.
Montoyo et al. (2009) "Conditional deletion of the MHC class I-related receptor FcRn reveals the sites of IgG homeostasis in mice," Proc. Natl. Acad. Sci. USA. 106:2788-2793.
Morea et al. (2000) "Antibody Modeling: Implications for Engineering and Design," Methods, 20:267-279.
Newburger et al. (2004) "Diagnosis, Treatment, and Long-Term Management of Kawasaki Disease: a Statement for Health Professionals From the Committee on Rheumatic Fever, Endocarditis, and Kawasaki Disease, Council on Cardiovascular Disease in the Young, American Heart Association," Pediatrics. 114:1708-1733.
Newland et al. (1983) "High-dose intravenous IgG in adults with autoimmune thrombocytopenia," the Lancet, 84-87.
Nieswandt et al. (1999) "Acute systemic reaction and lung alterations induced by an antiplatelet integrin gpIIb/IIIa antibody in mice," Blood. 94:684-693.
Niknami et al. (Jun. 2013) "Beneficial effect of a multimerized immunoglobulin Fc in an animal model of inflammatory neuropathy (experimental autoimmune neuritis)," J. Peripher. Nerv. Syst. 18(2):141-52.
Ober et al. (2004) "Exocytosis of IgG as mediated by the receptor, FcRn: an analysis at the single-molecule level," Proc. Natl. Acad. Sci. USA. 101:11076-11081.
Ober et al. (2004) "Visualizing the site and dynamics of IgG salvage by the MHC Class I-related receptor, FcRn," J. Immunol. 172:2021-2029.
Oshima et al. (1998) "Characterization of murine CD70 by molecular cloning and mAb," Int. Immunol. 10(4):517-526.
Patel et al. (2011) "Neonatal Fc receptor blockade by Fc engineering ameliorates arthritis in a murine model," J. Immunol. 187(2):1015-1022.
Pevzner et al. (2011) "Anti-LRP4 autoantibodies in AChR-and MuSK-antibody-negative myasthenia gravis," J. Neurol., 9 pages.
Prabhat et al. (2007) "Elucidation of intracellular recycling pathways leading to exocytosis of the Fc receptor, FcRn, by using multifocal plane microscopy," Proc. Natl. Acad. Sci. USA. 104:5889-5894.
Presta et al. (2002) "Engineering therapeutic antibodies for improved function," Biochemical Society Transactions, 30(4):487-490.
Reddy et al. (2000) "Elimination of Fc Receptor-Dependent Effector Functions of a Modified IgG4 Monoclonal Antibody to Human CD4," J. Immunol., 164:1925-1933.
Roopenian et al. (2003) "The MHC class I-like IgG receptor controls perinatal IgG transport, IgG homeostasis, and fate of IgG-Fc-coupled drugs," J. Immunology. 170:3528-3533.
Roopenian et al. (2007) "FcRn: the neonatal Fc receptor comes of age," Nat. Rev. Immunol. 7(9):715-725.
Roux et al. (1998) "Comparisons of the Ability of Human IgG3 Hinge Mutants, IgM, IgE, and IgA2, to Form Small Immune Complexes: a Role for Flexibility and Geometry," the Journal of Immunology, 4083-4090.
Schwab et al. (Mar. 2013) "Intravenous immunoglobulin therapy: how does IgG modulate the immune system?" Nat. Rev. Immunol. 176(13).
Seidling et al. (2013) "Analysis of high-dose intravenous immunoglobulin therapy in 16 patients with refractory autoimmune blistering skin disease: high efficacy and no serious adverse events," Acta Derm Venereol. 93:346-349.
Semple (2010) "Animal models of immune thrombocytopenia (ITP)," Annals of Hematology. 89:37-44.

(56) References Cited

OTHER PUBLICATIONS

Sesarman et al. (2010) "The neonatal Fc receptor as therapeutic target in IgG-mediated autoimmune diseases," Cell. Mol. Life Sci. 67(15):2533-2550.
Sewell: Ed. (Jan. 22, 2010) First National Immunoglobulin Database Report. Department of Health.
Shelton (1999) "Acquired myasthenia gravis: what we have learned from experimental and spontaneous animal models," Veterinary Immunology and Immunopathology. 69:239-249.
Shields et al. (2001) "High Resolution Mapping of the Binding Site on Human IgG1 for FcgammaRI, FcgammaRII, FcgammaRIII, and FcRn and Design of IgG1 Variants with Improved Binding to the FcgammaR," the Journal of Biological Chemistry, 276(9):6591-6604.
Sockolosky et al. (2015) "The neonatal Fc receptor, FcRn, as a target for drug delivery and therapy," Advanced Drug Delivery Reviews, 91:109-124.
Soliven (2012) "Autoimmune neuropathies: insights from animal models," Journal of the Peripheral Nervous System. 17:28-33.
Sorde et al. (2017) "Massive immune response against IVIg interferes with response against other antigens in mice: a new mode of action?," PLoS One, 12(10):e0186046, 15 pages.
Stamos et al. (2004) "Crystal structure of the HGF beta-chain in complex with the Sema domain of the Met receptor," Embo J. 23(12):2325-2335.
Swiercz et al. (May 27, 2014) "Use of Fc-engineered antibodies as clearing agents to increase contrast during Pet," J. Nucl. Med. 55:1204-1207.
Task Force of the Medical Scientific Advisory Board of the Myasthenia Gravis Foundation of America, et al. (2000) "Myasthenia gravis," Neurology, 55:16-23.
Tramontano et al. (1990) "Framework Residue 71 is a Major Determinant of the Position and Conformation of the Second Hypervariable Region in the VH Domains of Immunoglobulins," J. Mol. Biol., 215:175-182.
Ulrichts et al. (2018) "Neonatal Fc receptor antagonist efgartigimod safely and sustainably reduces IgGs in humans," J. Clin. Invest., 16 pages.
Ulrichts et al. (May 2017) "ARGX-113: Towards a Safe and Selective Elimination of Pathogenic Autoantibodies," 13th International Conference on Myasthenia Gravis and Related Disorders, May 15-17, 2017. New York, New York. Poster Presentation.
Vaccaro et al. (2005) "Engineering the Fc region of immunoglobulin G to modulate in vivo antibody levels," Nat. Biotechnol. 23(10):1283-1288.
Vaccaro et al. (2006) "Divergent activities of an engineered antibody in murine and human systems have implications for therapeutic antibodies" Proc. Natl. Acad. Sci. USA. 103(49):18709-18714.
Van Der Meche et al. (1992) "A randomized trial comparing intravenous immune globulin and plasma exchange in Guillain-Barre syndrome. Dutch Guillain-Barre Study Group," N. Engl. J. Med. 326:1123-1129.
Wani et al. (2006) "Familial hypercatabolic hypoproteinemia caused by deficiency of the neonatal Fc receptor, FcRn, due to a mutant beta2-microglobulin gene," Proc. Natl. Acad. Sci. USA. 103(13):5084-5989.
Woods et al. (1984) "Autoantibodies against platelet glycoprotein lb in patients with chronic immune thrombocytopenia purpura," Blood. 64:156-160.
Written Opinion corresponding to International Patent Application No. PCT/EP2013/068399, mailed Apr. 14, 2014.
Xu et al. (2000) "In Vitro Characterization of Five Humanized OKT3 Effector Function Variant Antibodies," Cellular Immunology, 200:16-26.
Yang et al., (2011) "Non-radioactive serological diagnosis of myasthenia gravis and clinical features of patients from Tianjin, China," Journal of Neurological Sciences, 301:71-76, 2011.
Ying et al. (2012) "Soluble Monomeric IgG1 Fc," the Journal of Biological Chemistry, 287(23):19399-19408.

Ying et al. (2013) "Engineered Soluble Monomeric IgG1 CH3 Domain," the Journal of Biological Chemistry, 288 (35):25154-25164.
Zhang et al. (2012) "Autoantibodies to Lipoprotein-Related Protein in Patients With Double-Seronegative Myasthenia Gravis," Arch Neurol, 69(4):445-451.
Zhou et al. (2005) "Conferring the binding properties of the mouse MHC Class I related receptor, FcRn, onto the human ortholog by sequential rounds of site-directed mutagenesis," J. Mol. Biol. 345:1071-1081.
Zhou et al. (2003) "Generation of mutated variants of the human form of the MHC class l-related receptor, FcRn, with increased affinity for mouse immunoglobulin G," J. Mol. Biol. 332:901-913.
Zinman et al. (2007) "IV immunoglobulin in patients with myasthenia gravis: a randomized controlled trial," Neurology 68:837-841.
Bussel et al., "Long-term use of the thrombopoietin-mimetic romiplostim in children with severe chronic immune thrombocytopenia (ITP) : Romiplostim in Pediatric ITP" Pediatric Blood and Cancer, Feb. 1, 2015, vol. 62, No. 2, pp. 208-213.
Dick Jr. et al., "C-Terminal Lysine Variants in Fully Human Monoclonal Antibodies: Investigation of Test Methods and Possible Causes", Biotechnology and Bioengineering, 2008, vol. 100, No. 6, pp. 1132-1143.
Eddleston et al., "Blockade of the Neonatal Fc Receptor (FcRn) Represents an Effective Mechanism for the Removal of Pathogenic Autoantibodies in Primary Immune Thrombocytopenia", Database Biosis [Online] Biosciences Information Service, Philadelphia, PA, Dec. 7, 2017, XP002794883, Database accession no. PREV201900186122 abstract & Blood, vol. 130, No. Suppl. 1, p. 230.
Howard et al., "Randomized phase 2 study of FcRn antagonist efgartigimod in generalized myasthenia gravis", Neurology, 2019, vol. 92, No. 23, pp. 1-8.
Swiss Webster Mice, by Taconic, Aug. 23, 2018, pp. 1-7.
U.S. Appl. No. 16/893,863, filed Jun. 5, 2020, Filip Borgions.
Anonymous: "A Study to Evaluate the Safety, Efficacy, and Pharmacokinetics of ARGX-113 in Patients with ITP", Apr. 6, 2017, pp. 1-7.
Bussel et al., "A Randomized, Double-Blind Study of Romiplostim to Determine its Safety and Efficacy in Children with Immune Thrombocytopenia", Blood, vol. 118, No. 1, Jul. 7, 2011, pp. 28-36.
De Haard et al., "Advancing ARGX-113 and ARGX-110 to Clinical Proof of Concept", Dec. 4, 2016, pp. 1-575.
International Search Report and Written Opinion in related PCT Application No. PCT/IB2019/054786, mailed Dec. 18, 2109 (27 pages).
Ulrichts et al., "ARGX-113, a Novel Fc-Based Approach for Antibody-Induced Pathologies Such as Primary Immune Thrombocytopenia", Blood, vol. 128, No. 22, Dec. 2016, p. 4919, 58th annual Meeting and Exposition of the American-Society-of-Hematology; San Diego, CA, Dec. 3-6, 2016.
U.S. Appl. No. 14/580,771, 2015/0218239, 10,316,073, filed Dec. 23, 2014, Aug. 6, 2015, Jun. 11, 2019, Peter Ulrichts.
U.S. Appl. No. 16/893,863, 2020/0399363, filed Jun. 5, 2020, Dec. 24, 2020, Filip Borgions.
U.S. Appl. No. 16/435,166, 2020/0024344, filed Jun. 7, 2019, Jan. 23, 2020, Hans de Haard.
PCT/IB2019/054786, WO 2019/234713, filed Jun. 7, 2019, Dec. 12, 2019, Hans de Haard.
U.S. Appl. No. 17/144,481, 2021/0236596, filed Jan. 8, 2021, Aug. 5, 2021, Peter Verheesen.
"Anthony et al., Apr. 18, 2008, Science, 320(5874): 373-376", Document D14 submitted with Notice of Opposition for European Patent No. 3087095 (Application No. 14827372.5), dated May 7, 2020.O.
"ArGEN-X advances ARGX-113 into preclinical development for autoimmune disorders, Apr. 24, 2014", Document D38 submitted with Notice of Opposition for European Patent No. 3087095 (Application No. 14827372.5), dated May 7, 2020.

(56) References Cited

OTHER PUBLICATIONS

"ArGEN-X Announces Positive Preclinical Results for ARGX-113, Aug. 19, 2014", Document D39 submitted with Notice of Opposition for European Patent No. 3087095 (Application No. 14827372.5), dated May 7, 2020.
"Assignment submission for U.S. Appl. No. 61/920,547 confirming change of legal form of arGEN-X B.V. to arGEN-X N.V. on May 28, 2014", Document D30 submitted with Notice of Opposition for European Patent No. 3087095 (Application No. 14827372.5), dated May 7, 2020.
"Auxiliary Request 1—Annotated Version" for European Patent No. 3087095 (Application No. 14827372.5), dated Oct. 28, 2020, 5 pages.
"Auxiliary Request 1—Clean Version" for European Patent No. 3087095 (Application No. 14827372.5), dated Oct. 28, 2020, 5 pages.
"Auxiliary Request 2—Annotated Version" for European Patent No. 3087095 (Application No. 14827372.5), dated Oct. 28, 2020, 5 pages.
"Auxiliary Request 2—Clean Version" for European Patent No. 3087095 (Application No. 14827372.5), dated Oct. 28, 2020, 4 pages.
"Blumberg & Lencer, Oct. 2005, Nat Biotechnol., 23(10): 1232-1234", Document D03 submitted with Notice of Opposition for European Patent No. 3087095 (Application No. 14827372.5), dated May 7, 2020.
"Bruhns et al., Apr. 2003, Immunity, 18(4): 573-571", Document D16 submitted with Notice of Opposition for European Patent No. 3087095 (Application No. 14827372.5), dated May 7, 2020.
"Brych et al., Feb. 2010, J Pharm Sci., 99(2): 764-781", Document D37 submitted with Notice of Opposition for European Patent No. 3087095 (Application No. 14827372.5), dated May 7, 2020.
"Carter, May 2006, Nat Rev immunol., 6(5): 343-357", Document D22 submitted with Notice of Opposition for European Patent No. 3087095 (Application No. 14827372.5), dated May 7, 2020.
"Challa et al., Sep.-Oct. 2013, MAbs, 5(5): 655-659", Document D10 submitted with Notice of Opposition for European Patent No. 3087095 (Application No. 14827372.5), dated May 7, 2020.
"Corrected Filing Receipt for U.S. Appl. No. 61/920,547 dated Apr. 16, 2015", Document D27 submitted with Notice of Opposition for European Patent No. 3087095 (Application No. 14827372.5), dated May 7, 2020.
"Corrected Filing Receipt for U.S. Appl. No. 61/920,547 dated Apr. 18, 2014", Document D26 submitted with to Notice of Opposition for European Patent No. 3087095 (Application No. 14827372.5), dated May 7, 2020.
"Cover Letter to the European Patent Office" for European Patent No. 3087095 (Application No. 14827372.5), dated Oct. 28, 2020, 1 page.
"Dall'Acqua et al., Nov. 1, 2002, J Immunol., 169(9): 5171-5180", Document D21 submitted with Notice of Opposition for European Patent No. 3087095 (Application No. 14827372.5), dated May 7, 2020.
"Debre et al., Oct. 16, 1993, Lancet, 342: 945-949", Document D12 submitted with Notice of Opposition for European Patent No. 3087095 (Application No. 14827372.5), dated May 7, 2020.
"Declaration of Pieter Spuijbroek", Document D42 submitted with Reply to Notice of Opposition for European Patent No. 3087095 (Application No. 14827372.5), dated Oct. 28, 2020, 5 pages.
"Dimitrov, Jan.-Feb. 2009, MAbs, 1(1): 26-28", Document D20 submitted with Notice of Opposition for European Patent No. 3087095 (Application No. 14827372.5), dated May 7, 2020.
"EP 1896503 Amended Claims and Response submitted Feb. 23, 2014 during prosecution of the application which led to grant of D1", Document D02a submitted with Notice of Opposition for European Patent No. 3087095 (Application No. 14827372.5), dated May 7, 2020.
"EP 1896503 B1 dated Oct. 29, 2014", Document D01 submitted with Reply to Notice of Opposition for European Patent No. 3087095 (Application No. 14827372.5), dated May 7, 2020.
"EP 3087095 B1 dated Aug. 7, 2019" submitted with Notice of Opposition for European Patent No. 3087095 (Application No. 14827372.5), dated May 7, 2020.
"Filing Receipt for U.S. Appl. No. 61/920,547 dated Jan. 21, 2014", Document D25 submitted with Notice of Opposition for European Patent No. 3087095 (Application No. 14827372.5), dated May 7, 2020.
"Gan et al., May 2009, Traffic, 10(5): 600-614", Document D08 submitted with Notice of Opposition for European Patent No. 3087095 (Application No. 14827372.5), dated May 7, 2020.
"Goh and Ng, Sep. 2018, Crit Rev Biotechnol., 38(6): 851-867", Document D19 submitted with Notice of Opposition for European Patent No. 3087095 (Application No. 14827372.5), dated May 7, 2020.
"Gómez-Guerrero et al., Feb. 15, 2000, J Immunol., 164(4): 2092-2101", Document D15 submitted with Notice of Opposition for European Patent No. 3087095 (Application No. 14827372.5), dated May 7, 2020.
"Inventor Assignment of U.S. Appl. No. 61/920,547 to arGEN-X B.V. executed Oct. 31, 2014 and Nov. 4, 2014", Document D29 submitted with Notice of Opposition for European Patent No. 3087095 (Application No. 14827372.5), dated May 7, 2020.
"Inventor Assignment of U.S. Appl. No. 61/920,547 to The Board of Regents of the University of Texas System executed Dec. 23, 2014", Document D28 submitted with Notice of Opposition for European Patent No. 3087095 (Application No. 14827372.5), dated May 7, 2020.
"Jefferis and Lefranc, July-Aug. 2009, MAbs, 1(4): 332-338", Document D35 submitted with Notice of Opposition for European Patent No. 3087095 (Application No. 14827372.5), dated May 7, 2020.
"Kaneko et al., Aug. 4, 2006, Science, 313(5787): 670-673", Document D17 submitted with Notice of Opposition for European Patent No. 3087095 (Application No. 14827372.5), dated May 7, 2020.
"Main Request—Annotated Version" for European Patent No. 3087095 (Application No. 14827372.5), dated Oct. 28, 2020, 5 pages.
"Main Request—Clean Version" for European Patent No. 3087095 (Application No. 14827372.5), dated Oct. 28, 2020, 5 pages.
"Notice of Opposition" to European Patent No. 3087095 (Application No. 14827372.5), dated May 7, 2020, 47 pages.
"Online Filing Acknowledgement for Notice of Opposition" for European Patent No. 3087095 (Application No. 14827372.5), dated May 7, 2020, 3 pages.
"Online Filing Acknowledgement for Reply to Notice of Opposition" for European Patent No. 3087095 (Application No. 14827372.5), dated Oct. 28, 2020, 2 pages.
"Patel et al., Jul. 15, 2011, J Immunol., 187(2): 1015-1022", Document D09 submitted with Notice of Opposition for European Patent No. 3087095 (Application No. 14827372.5), dated May 7, 2020.
"PCT Request for as filed for PCT/US2014/072087 on Dec. 23, 2014", Document D34 submitted with Notice of Opposition for European Patent No. 3087095 (Application No. 14827372.5), dated May 7, 2020.
"Proof of Employment for Inventor/Applicant Sally Ward", Document D40 submitted with Reply to Notice of Opposition for European Patent No. 3087095 (Application No. 14827372.5), dated Oct. 28, 2020, 1 page.
"Putnam and Miyake, Apr. 1958, J Biol Chem, 231(2):671-684", Document D33 submitted with Notice of Opposition for European Patent No. 3087095 (Application No. 14827372.5), dated May 7, 2020.
"Pyzik et al., Jul. 10, 2019, Front Immunol., 10: 1540", Document D31 submitted with Notice of Opposition for European Patent No. 3087095 (Application No. 14827372.5), dated May 7, 2020.
"Reply to Notice of Opposition" for European Patent No. 3087095 (Application No. 14827372.5), dated Oct. 28, 2020, 35 pages,.
"Rule 90101 of the Rules and Regulations of the Board of Regents of the University of Texas System governing intellectual property" dated Feb. 27, 2012, submitted with Reply to Notice of Opposition for European Patent No. 3087095 (Application No. 14827372.5), on Oct. 28, 2020, 21 pages.

(56) References Cited

OTHER PUBLICATIONS

"Samuelsson et al., Jan. 19, 2001, Science, 291(5503): 484-486", Document D13 submitted with Notice of Opposition for European Patent No. 3087095 (Application No. 14827372.5), dated May 7, 2020.

"Schwab and Nimmerjahn, Mar. 2013, Nat Rev Immunol., 13(3): 176-189", Document D11 submitted with Notice of Opposition for European Patent No. 3087095 (Application No. 14827372.5), dated May 7, 2020.

"Sequence alignment of SEQ ID No. 22 from D6 and SEQ ID Nos. 1, 2, and 3 from the Patent", Document D32 submitted with Notice of Opposition for European Patent No. 3087095 (Application No. 14827372.5), dated May 7, 2020.

"Sequence Alignment of SEQ ID Nos. 1-3 from Patent and corresponding portion of Uniprot ID: P01857", Document D24 submitted with Notice of Opposition for European Patent No. 3087095 (Application No. 14827372.5), dated May 7, 2020.

"Shields et al., Mar. 2, 2001, J Biol Chem., 276(9): 6591-6604", Document D23 submitted with Notice of Opposition for European Patent No. 3087095 (Application No. 14827372.5), dated May 7, 2020.

"Ulrichts et al., Oct. 1, 2018, J Clin Invest., 128(10): 4372-4386", Document D18 submitted with Notice of Opposition for European Patent No. 3087095 (Application No. 14827372.5), dated May 7, 2020.

"UniProtKB—P01857 (IGHG1_HUMAN)"submitted with Reply to Notice of Opposition for European Patent No. 3087095 (Application No. 14827372.5), dated Oct. 28, 2020, 6 pages.

"Vacarro et al., Dec. 2006, Proc Natl Acad Sci USA, 103(49): 18709-18714", Document D07 submitted with Notice of Opposition for European Patent No. 3087095 (Application No. 14827372.5), dated May 7, 2020.

"Vaccarro et al., Oct. 2005, Nat Biotechnol., 23(10): 1283-1288", Document D04 submitted with Notice of Opposition for European Patent No. 3087095 (Application No. 14827372.5), dated May 7, 2020.

"Ward & Ober, 2009, Chapter 4, Adv. Immunol., 103: 77-115", Document D05 submitted with Notice of Opposition for European Patent No. 3087095 (Application No. 14827372.5), dated May 7, 2020.

"Weiner and Carter, May 2005, 23(5): 556-557", Document D36 submitted with Notice of Opposition for European Patent No. 3087095 (Application No. 14827372.5), dated May 7, 2020.

"WO 2006/130834 A2 dated Dec. 7, 2006", Document D02 submitted with Notice of Opposition for European Patent No. 3087095 (Application No. 14827372.5), dated May 7, 2020.

"WO 2013/074598 A1 dated May 23, 2013", Document D06 submitted with Notice of Opposition for European Patent No. 3087095 (Application No. 14827372.5), dated May 7, 2020.

"WO 2015/100299 A1 dated Jul. 2, 2015" submitted with Notice of Opposition for European Patent No. 3087095 (Application No. 14827372.5), dated May 7, 2020.

Balighi et al., "Comparing early and late treatments with rituximab in pemphigus vulgaris: which one is better?", Archives of Dermatological Research, Dec. 1, 2018, 311(1): 63-69.

Clinicaltrials.gov, "A Study to Evaluate the Safety, PD, PK and Efficacy of ARGX-113 in Patients with Pemphigus", ClinicalTrials.gov Identifier NCT03334058, Nov. 7, 2017, 8 pages.

Clinicaltrials.gov, "A Study to Evaluate the Safety, PD, PK and Efficacy of ARGX-113 in Patients with Pemphigus", ClinicalTrials.gov Identifier NCT04598477, Oct. 22, 2020, 10 pages.

Combined Search and Examination Report for Great Britain Application No. GB1617270.2, mailed Aug. 3, 2017, 6 pages.

Daugherty et al., "Formulation and delivery issues for monoclonal antibody therapeutics", Adv Drug Deliv Rev., Aug. 7, 2006, 58(5-6): 686-706.

Evoli et al., "Diagnosis and therapy of myasthenia gravis with antibodies to muscle-specific kinase", Autoimmunity Reviews, 2013, 12(9): 931-935.

International Preliminary Report on Patentability for PCT International Patent Application No. PCT/IB2016/000398, mailed Sep. 12, 2017.

International Preliminary Report on Patentability for PCT International Patent Application No. PCT/IB2019/054786, mailed Dec. 8, 2020.

International Search Report with Written Opinion for PCT International Patent Application No. PCT/EP2020/065716, mailed Sep. 14, 2020.

International Search Report with Written Opinion for PCT International Patent Application No. PCT/IB2016/000398, mailed Aug. 22, 2016.

International Search Report with Written Opinion for PCT International Patent Application No. PCT/EP2021/050275, mailed Apr. 8, 2021.

Jaretzkl et al., "Myasthenia gravis: recommendations for clinical research standards. Task Force of the Medical Scientific Advisory Board of the Myasthenia Gravis Foundation of America", Ann Thorac Surg., Jul. 2000, 70(1): 327-334.

Joshi et al., "An Update on Disease Modifying Antirheumatic Drugs", Inflammation and Allergy—Drug Targets, 2014, 13: 249-261.

Kabat et al., "Unusual Distributions of amino Acids in Complementarity-determining (Hypervariable) Segments of Heavy and Light Chains of Immunoglobulins and Their Possible Roles in Specificity of Antibody-combining Sites", the Journal of Biological Chemistry, Oct. 1, 1977, 252(19): 6609-6616.

Kang et al., "Rapid Formulation Development for Monoclonal Antibodies", BioProcess International, Apr. 12, 2016, retrieved from url: https://bioprocessintl.com/manufacturing/formulation/rapid-formulation-development-for-monoclonal-antibodies/.

Li et al., "Myasthenia gravis: newer therapies offer sustained improvement", Cleveland Clinic Journal of Medicine, 2013, 80(11): 711-721.

Robak et al., "Phase II, Multiple-Dose Study of Anti-FcRn Antibody, Rozanolixizumab (UCB7665), in Patients with Primary Immune Thrombocytopenia: Interim Analysis", Blood, Dec. 7, 2017, 130(Suppl. 1): 15, $59^{th}$ Annual Meeting of the American-Society-of-Hematology, Dec. 9-12, 2017.

Rosenwasser et al., "Anti-CD23", Clinical Reviews in Allergy and Immunology, Aug. 2005, 29(1): 61-72.

Shang et al., "Modular protein expression by RNA trans-splicing enables flexible expression of antibody formats in mammalian cells from a dual-host phage display vector", Protein Engineering, Design & Selection, 2015, vol. 28, No. 10, pp. 437-444.

Silvestri et al., "Treatment-Refractory Myasthenia Gravis", Journal of Clinical Neuromuscular Disease, Jun. 2014, 15(4): 167-178.

Wang et al., "Protein aggregation and its inhibition on biopharmaceutics", International Journal of Pharmaceutics, Jan. 31, 2005, 289(1-2): 1-30.

Tavakolpour, "Current and future treatment options for pemphigus: Is it time to move towards more effective treatments?" Int Immunopharmacol. 2017;53:133-142.

Wang et al., "Antibody structure, instability, and formulation," J Pharm Sci. 2007;96(1):1-26.

Verschuuren, "A double-blind placebocontrolled study to evaluate safety and efficacy of fcrn antagonist ARGX-113 in generalized MG," Elsevier Science Publishers, Amsterdam, NL, 2018.

Basta and Dalakas, "High-dose intravenous immunoglobulin exerts its beneficial effect in patients with dermatomyositis by blocking endomysial deposition of activated complement fragments," J Clin Invest. 1994;94(5):1729-35.

Dalakas et al., "High-dose intravenous immune globulin for stiff-person syndrome," N Engl J Med. 2001;345(26):1870-6.

Dalakas, "Update on Intravenous Immunoglobulin in Neurology: Modulating Neuro-autoimmunity, Evolving Factors on Efficacy and Dosing and Challenges on Stopping Chronic IVIg Therapy," Neurotherapeutics. 2021;18(4):2397-2418.

Heo, "Efgartigimod: First Approval," Drugs. 2022;82(3):341-348.

Bas Van Der Woning, "R&D Day: Fifth Efgartigimod Indication: Myositis," ARGENX, Jul. 20, 2021, pp. 23-37.

Julien et al., "Abstract No. L10 Efgartigimod Prevents Necrosis and Allows for Muscle Fiber Regeneration in a Humanized Mouse

(56) References Cited

OTHER PUBLICATIONS

Model of Immune-mediated Necrotizing Myopathy (IMNM)," ACR Meeting Abstracts, ACR Conference 2022, Oct. 18, 2022, pp. 1-4.

PCT Search Report and Written Opinion for PCT/EP2023/054065, mailed May 3, 2023.

Kiessling, "Safety, Pharmacokinetics and Pharmacodynamics of the FCRN Inhibitor UCB7665: a Phase I Study," Journal of the Peripheral Nervous System. 2017;22(3):226-414.

Miyagawa, "Idiopathic Thrombocytopenia Purpura," Mebio. 2017;34(6):102-107.

Alipour-Faz et al., "A comparison between IVIG and plasma exchange as preparations before thymectomy in myasthenia gravis patients," Acta Neurol Belg. 2017;117(1):245-249.

Howard et al., "A double-blind placebo-controlled study to evaluate safety and efficacy of FcRn antagonist ARGX-113 (efgartigimod) in generalized myasthenia gravis," Elsevier 70th Annual Meeting of the American Academmy of Neurology, AAN, 2018.

Van Faassen, et al., "Serum albumin-binding VH Hs with variable pH sensitivities enable tailored half-life extension of biologics," Faseb J. 2020 34(6): 8155-8171 doi: 10.1096/fj.201903231R. Epub Apr. 28, 2020.

Partial International Search Report issued for International Application No. PCT/EP2023/066180, mailed Sep. 27, 2023.

International Search Report and Written Opinion issued for PCT/EP2023/066163, mailed Sep. 27, 2023.

Allen et al., "Efgartigimod in chronic inflammatory demyelinating polyneuropathy: Adhere phase 2 trial design", Muscle and Nerve 20201001 John Wiley and Sons Inc. NLD, Oct. 1, 2020, 62(Suppl 1), abstract (1 page).

Anonymous, "A Randomized, Double-Blinded, Placebo-Controlled Trial of Efgartigimod PH20 SC in Adult Patients With Pemphigus (Vulgaris or Foliaceus)", Jul. 16, 2021, Retrieved from the Internet: URL:https://rctportal.niph.go.jp/en/detail?trial_id= jRCT2061210025, 4 pages.

Anonymous, "Evaluating the Long-Term Safety and Tolerability of Efgartigimod PH20 SC Administered Subcutaneously in Patients With Generalized Myasthenia Gravis (ADAPTSC+)", Mar. 27, 2021, ClinicalTrials.gov, Retrieved from the Internet: URL:https://web.archive.org/web/20210327211859/https://clinicaltrials.gov/ct2/show/NCT04818671, 7 pages.

Anonymous, "History of Changes for Study: NCT05267600, A Phase 2/3 Study of Efgartigimod PH20 SC in Adult Participants With Bullous Pemphigoid (Ballad)", Apr. 14, 2022, p. 1-7.

Antohe et al., "Expression of functionally active FcRn and the differentiated bidirectional transport of IgG in human placental endothelial cells," Human Immunol., 2001, 62:93-105.

Azevedo, "argenx Doses First Subject in Study Evaluating Subcutaneous ARGX-113 for Autoimmune Diseases", Myasthenia Gravis News, 2017, 1-2.

Bitonti et al., "Pulmonary delivery of an erythropoietin Fc fusion protein in non-human primates through an immunoglobulin transport pathway," Proc. Natl. Acad. Sci. USA, 2004, 101:9763-9768.

Brinkhaus Maximilian et al., "The Fab region of IgG impairs the internalization pathway of FcRn upon Fc management," Nature Communications, 2022, 13(1):6073.

Burmeister et al., "Crystal structure at 2.2 A resolution of the MHC-related neonatal Fc receptor," Nature, 1994, 372(6504):336-343.

Challa et al., "Neonatal Fc receptor expression in macrophages is indispensable for IgG homeostasis," MAbs., Apr. 30, 2019, 11(5):848-860.

Dalakas et al., "A controlled trial of high-dose intravenous immune globulin infusions as treatment for dermatomyositis," N Engl J Med., 1993, 329(27):1993-2000.

Dall'Acqua et al., "Properties of human IgG1s engineered for enhanced binding to the neonatal Fc receptor (FcRn)," J. Biol. Chem., 2006, 281:23514-23524.

Deisenhofer, "Crystallographic refinement and atomic models of a human Fc fragment and its complex with fragment B of protein A from *Staphylococcus aureus* at 2.9- and 2.8-A resolution," Biochemistry, Apr. 28, 1981, 20(9):2361-2370.

Dickinson et al., "Bidirectional FcRn-dependent IgG transport in a polarized human intestinal epithelial cell line," J. Clin. Invest., Oct. 1999, 104(7):903-911.

Firan et al., "The MHC class I-related receptor, FcRn, plays an essential role in the maternofetal transfer of gamma-globulin in humans", Int. Immunol., 2001, 13(8):993-1002.

Ghanima et al., "Pharmacokinetic / Pharmacodynamic (PK/PD) Simulations Guide Selection of the Dose for Administration of Efgartigimod Subcutaneously in a Phase 3 Clinical Trial in Patients with Primary Immune Thrombocytopenia", Blood, Nov. 5, 2021, 138(Suppl. 1):3165-3165.

Ghetie et al., "FcRn: the MHC class I-related receptor that is more than an IgG transporter", Immunol Today, 1997, 18(12):592-598.

Ghetie et al., "Multiple roles for the major histocompatibility complex class I-related receptor FcRn", Annu. Rev. Immunol., 2000, 18:739-766.

Guidance for Industry Estimating the maximum safe starting dose in initial clinical trials for therapeutics in adult healthy volunteers FDA, Jul. 2005, pp. 1-27.

Hans-Hartmut et al., "Targeting FcRn for immunomodulation: Benefits, risks, and practical considerations", J Allergy Clin Immunol, Sep. 1, 2020, 146(3):479-491.

Hinton et al., "Engineered human IgG antibodies with longer serum half-lives in primates," J. Biol. Chem., 2004, 279:6213-6216.

Israel et al., "Increased clearance of IgG in mice that lack beta 2-microglobulin: possible protective role of FcRn," Immunolgy, 1996, 89:573-578.

Kabat et al., "In: Sequences of proteins of immunological interest", U.S. Department of Health and Human Services, 1991, (Title Page and Table of Contents), 11 pages.

Kasperkiewicz et al., "Pemphigus." Nat Rev Dis Primers., 2017, 3:17026.

Kasprick et al., "Treatment with anti-neonatal Fc receptor (FcRn) antibody ameliorates experimental epidermolysis bullosa acquisita in mice", British Journal of Pharmacology, Wiley-Blackwell, Mar. 6, 2020, 177(10):2381-2392.

Kiessling Peter et al., "The FcRn inhibitor rozanolixizumab reduces human serum IgG concentration: a randomized phase 1 study", Science Translational Medicine, Nov. 1, 2017, 9(414):1-12.

Kim et al., "Localization of the site of the murine IgG1 molecule that is involved in binding to the murine intestinal Fc receptor," Eur. J. Immunol., 1994, 24:2429-2434.

Kobayashi et al., "FcRn-mediated transcytosis of immunoglobulin G in human renal proximal tubular epithelial cells", Am. J. Physiol. Renal Physiol., 2002, 282:F358-F365.

Ishii-Watabe et al., "Molecular Design of Therapeutics Monoclonal Antibodies," Journal of Pharmaceutical Science and Technology, Japan, 2014, 74(1):4-11.

Matt Hoffman, "Subcutaneous Efgartigimod Shows Noninferiority to IV Formulation in Generalized Myasthenia Gravis", Mar. 23, 2022, Neurology, Retrieved from the Internet: URL:https://web.archive.org/web/20220326043901/https://www.neurologylive.com/view/subcutaneous-efgartigimod-noninferior-iv-formulation-vygart-generalized-myasthenia-gravis, 3 pages.

Maho-Vaillant et al., "FcRn Antagonism Leads to a Decrease of Desmoglein-Specific B Cells: Secondary Analysis of a Phase 2 Study of Efgartigimod in Pemphigus Vulgaris and Pemphigus Foliaceus", Frontiers in Immunology, May 18, 2022, 13(Article 863095):14 pages.

McCarthy et al., "Bidirectional transcytosis of IgG by the rat neonatal Fc receptor expressed in a rat kidney cell line: a system to study protein transport across epithelia", J. Cell Sci., 2000, 113:1277-1285.

Medesan et al., "Comparative studies of rat IgG to further delineate the Fc:FcRn interaction site," Eur. J. Immunol., 1998, 28:2092-2100.

Nih, A Study to Assess the Long-term Safety and Efficacy of a Subcutaneous Formulation of Efgartigimod PH20 SC in Adults With Pemphigus (Vulgaris or Foliaceus), Oct. 22, 2020, Retrieved from the Internet: URL:https://web.archive.org/web/20201101124721/https://clinicaltrials.gov/ct2/show/NCT04598477, 10 pages.

(56) References Cited

OTHER PUBLICATIONS

Popov et al., "The stoichiometry and affinity of the interaction of murine Fc fragments with the MHC class I-related receptor, FcRn," Mol. Immol., 1996, 33:521-530.
Raghavan et al., "Analysis of the pH Dependence of the Neonatal Fc Receptor/Immunoglobulin G Interaction Using Antibody and Receptor Variants," Biochemistry, 1995, 34:14649-14657.
Rudikoff et al., "Single amino acid substitution altering antigen-binding specificity", Proc. Natl. Acad. Sci. USA, 1982, 79(6):1979-1983.
Sewell: Ed., "First National Immunoglobulin Database Report(2008-2009)", Department of Health, Jan. 22, 2010, 82 pages.
Spiekermann et al., "Receptor-mediated Immunoglobulin G Transport Across Mucosal Barriers in Adult Life: Functional Expression of FcRn in the Mammalian Lung", J. Exp. Med., 2002, 196(3):303-310.
Vitetta et al., "Considering therapeutic antibodies", Science, Jul. 21, 2006, 313(2):308-309.
Wittlin et al. "Pharmacokinetic/Pharmacodynamic Simulations Guide Selection of the Dose for Administration of Efgartigimod Subcutaneously in a Phase 3 Clinical Trial in Patients with Primary Immune Thrombocytopenia", British Journal of Haematology; 62nd Annual Scientific Meeting of the British Society for Haematology 20220403 To 0220405 Virtual, Blackwell Publishing Ltd, Apr. 1, 2022, 197(Suppl. 1):44.
Yoshida et al., "Human Neonatal Fc Receptor Mediates Transport of IgG into Luminal Secretions for Delivery of Antigens to Mucosal Dendritic Cells," Immunity, 2004, 20:769-783.
Ha et al., "Immunoglobulin Fc Heterodimer Platform Technology: From Design to Applications in Therapeutic Antibodies and Proteins", Frontiers in Immunology, 2016, 7(394):1-16.
Arduin et al., "Highly reduced binding to high and low affinity mouse Fc gamma receptors by L234A/L235A and N297A Fc mutations engineered into mouse 1gG2a", 2015, Molecular Immunology, 63:456-463.
International Search Report received for PCT/US2006/021456, mailed on Nov. 17, 2006, 8 pages.
International Preliminary Report on Patentability for PCT International Patent Application No. PCT/EP2020/065716, mailed Dec. 16, 2021, 8 pages.
International Search Report and Written Opinion received for PCT/EP2023/050980 mailed on Apr. 12, 2023, 13 pages.
International Search Report and Written Opinion received for PCT/EP2023/061012 mailed on Aug. 3, 2023, 15 pages.
International Search Report and Written Opinion received for PCT/EP2023/066162 mailed Aug. 25, 2023, 18 pages.
International Search Report and Written Opinion received for PCT/IB2022/000443 mailed on Mar. 6, 2023, 29 pages.
Invitation to Pay Additional Fees received for PCT/IB2022/000443 mailed on Dec. 16, 2022, 19 pages.
International Preliminary Report on Patentability received for PCT/EP2018/084034, mailed on Jun. 18, 2020, 11 pages.
International Preliminary Report on Patentability received for PCT/US2006/021456, mailed Dec. 6, 2007, 8 pages.
Argenx Press Release "argenx Advances Clinical Development of Efgartigimod in Primary Sjogren's Disease", Mar. 27, 2024, 3 pages.
Argenx Press Release "argenx Announces Approval of VYVGART (efgartigimod alfa) in Japan for Adults with Primary Immune Thrombocytopenia", Mar. 26, 2024, 4 pages.
Argenx Press Release "argenx Reports Topline Results from ADDRESS Study of Efgartigimod SC in Pemphigus", Dec. 20, 2023, 5 pages.
Argenx Press Release "argenx Reports Topline Results from ADVANCE-SC Study of VYVGART Hytrulo in Primary Immune Thrombocytopenia", Nov. 28, 2023, 4 pages.
Broome C. et al., "Efficacy and safety of the neonatal Fc receptor inhibitor efgartigimod in adults with primary immune thrombocytopenia (Advance IV): a multicentre, randomised, placebo-controlled, phase 3 trial", Lancet, Nov. 4, 2023, 402(10413):1648-1659.
Bystryn et al., "IVIg selectively and rapidly decreases circulating pathogenic autoantibodies in pemphigus vulgaris", Autoimmunity, Nov. 2006; 39(7):601-607.
Howard Jr. et al., "Safety, efficacy, and tolerability of efgartigimod in patients with generalised myasthenia gravis (ADAPT): a multicentre, randomised, placebo-controlled, phase 3 trial", Lancet Neurol, 2021, 20:526-536.
Ulrichts et al., "Supplementary Data Neonatal Fc receptor antagonist efgartigimod safely and sustainably reduces IgGs in humans", J. Clin. Invest., Supplementary Data, 2018, 128(10):4372-4386, 15 pages.
Warne, "Development of high concentration protein biopharmaceuticals: the use of platform approaches in formulation development," Eur. J. Pharm. Biopharm. 2011;78(2):208-12.
Blumberg et al., "Blocking FcRn in humans reduces circulating IgG levels and inhibits IgG immune complex-mediated immune responses", Sci. Adv., Dec. 18, 2019, 5(12):eaax9586, 12 pages.
Clinicaltrials.gov, "A Study of Nipocalimab in Adults With Primary Sjogren's Syndrome (pSS)", ClinicalTrials.gov Identifier: NCT04968912, Jul. 20, 2021, 9 pages.
Clinicaltrials.gov, "A Study to Assess Effectiveness and Safety of Efgartigimod in Chinese Patients With Lupus Nephritis (ZL-1103-013)", ClinicalTrials.gov Identifier: NCT05810948, Oct. 2, 2023, 17 pages.
Clinicaltrials.gov, "Efficacy and Safety Study of Efgartigimod in Adults With Post-COVID-19 Pots (Pots)", ClinicalTrials.gov Identifier: NCT05633407, Nov. 29, 2022, 13 pages.
Clinicaltrials.gov, "History of Changes for Study: NCT05810961—a Study to Assess Effectiveness and Safety of Efgartigimod in Chinese Patients With Primary Membranous Nephropathy (ZL-1103-014)", Oct. 2, 2023, 11 pages.
Dylewski et al., "Exploiting the neonatal crystallizable fragment receptor to treat kidney disease", Kidney International, 2024, 105(1):54-64.
Goebeler et al., "Treatment of pemphigus vulgaris and foliaceus with efgartigimod, a neonatal Fc receptor inhibitor: a phase II multicentre, open-label feasibility trial", British Journal of Dermatology, 2022, 186(3):429-439.
Guptill et al., "Effect of FcRn antagonism on protective antibodies and to vaccines in IgG-mediated autoimmune diseases pemphigus and generalised myasthenia gravis", Autoimmunity, 2022, 55(8):620-631.
Hettmann et al., "Development of the clinical candidate PBD-C06, a humanized pGlu3-ABeta-specific antibody against Alzheimer's disease with reduced complement activation", Scientific Reports, 2020, 10(3294), pp. 1-13.
Howard Jr. et al., "Poster 133: Response to Coronavirus 2019 Vaccination in Patients Receiving Efgartigimod", AANEM, Sep. 21-24, 2022, 1 page.
Hubbard et al., "Poster—97: Design of a Phase 2, Multicenter, Randomized, Placebo-Controlled, Double-blind Study to Assess the Efficacy and Safety of Nipocalimab, an FcRn Antagonist, in Adults with Primary Sjogrens Syndrome", Clinical and Experimental Rheumatology, 2022, 40:2477-2579.
Knoebl et al., "Pb2305-Efgartigimod: Clinical Development of a Novel FcRn Antagonist in the Treatment of Autoimmune Diseases", Hemasphere, 2022, 6:2175-2176.
Lobner et al., "Engineered IgG1-Fc—one fragment to bind them all", Immunological Reviews, 2016, 270(1):113-131.
Olaru et al., "Neonatal Fc Receptor Promotes Immune Complex-Mediated Glomerular Disease", J Am Soc Nephrol, 2014, 25(5):918-925.
Patel et al., "Neonatal Fc receptor in human immunity: Function and role in therapeutic intervention", J Allergy Clin Immunol., Sep. 2020, 146(3):467-478.
Peene et al., "AB0520: Treatment of Primary Sjogren's Syndrome by Inhibiting FcRn: a Phase 2 Randomized, Placebo Controlled, Double-Blind, Proof of Concept Study with Efgartigimod", Scientific Abstracts, May 30, 2023, 1455-1456.
Polanco et al., "Spontaneous Remission of Nephrotic Syndrome in Idiopathic Membranous Nephropathy", J Am Soc Nephrol., 2010, 21(4):697-704.

(56) References Cited

OTHER PUBLICATIONS

Robak et al., "Single-Agent Ibrutinib Vs Chemoimmunotherapy Regimens for Treatment-Naive Patients with Chronic Lymphocytic Leukemia (CLL): a Cross-Trial Comparison", Blood, Dec. 7, 2017, 130(Suppl. 1):1750, 6 pages.

Rojas-Rivera et al., "Recent Clinical Trials Insights into the Treatment of Primary Membranous Nephropathy", Drugs, 2022, 82(2):109-132.

Ulrichts et al., "Supplementary Data Neonatal Fc receptor antagonist efgartigimod safely and sustainably reduces IgGs in humans", J. Clin. Invest., Supplementary Data, 2018, 128(10):4372-4386, pp. 1-15.

International Search Report and Written Opinion received for PCT Patent Application No. PCT/EP2023/066180, mailed on Nov. 17, 2023, 19 pages.

International Search Report and Written Opinion received for PCT Patent Application No. PCT/IB2023/000679, mailed on Apr. 3, 2024, 17 pages.

International Search Report and Written Opinion received for PCT Patent Application No. PCT/IB2023/000688, mailed on Apr. 29, 2024, 16 pages.

International Search Report and Written Opinion received for PCT Patent Application No. PCT/IB2023/000696, mailed on Jun. 4, 2024, 21 pages.

International Search Report and Written Opinion received for PCT Patent Application No. PCT/IB2024/000018, mailed on May 24, 2024, 16 pages.

International Search Report and Written Opinion received for PCT Patent Application No. PCT/IB2024/000041, mailed on Jun. 3, 2024, 14 pages.

International Search Report and Written Opinion received for PCT Patent Application No. PCT/IB2024/000120, dated Jul. 15, 2024, 14 pages.

Invitation to Pay Additional Fees received for PCT Patent Application No. PCT/IB2023/000696, mailed on Apr. 12, 2024, 15 pages.

U.S. Appl. No. 14/580,771, 2015/0218239, U.S. Pat. No. 10,316,073, filed Dec. 23, 2014, Aug. 6, 2015, Jun. 11, 2019, Peter Ulrichts.

U.S. Appl. No. 15/821,104, 2018/0179258, filed Nov. 22, 2017, Jun. 28, 2018, Peter Ulrichts.

U.S. Appl. No. 15/064,195, 2016/0264669, filed Mar. 8, 2016, Sep. 15, 2016, Peter Ulrichts.

U.S. Appl. No. 16/213,422, 2019/0194277, filed Dec. 7, 2018, Jun. 27. 2019, Johannes de Haard.

U.S. Appl. No. 16/435,166, filed Jun. 7, 2019, Hans de Haard.

* cited by examiner

COMPOSITIONS AND METHODS FOR TREATING IMMUNE THROMBOCYTOPENIA

RELATED APPLICATIONS

This application claims benefit of priority to U.S. Application No. 62/682,805, filed Jun. 8, 2018, U.S. Application No. 62/731,947, filed Sep. 16, 2018, and U.S. Application No. 62/732,414, filed Sep. 17, 2018, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Jun. 7, 2019, is named 613053_AGX5-045_Sequence_Listing.txt and is 8,115 bytes in size.

FIELD OF THE INVENTION

The invention relates generally to the treatment of immune thrombocytopenia (ITP), and more particularly to treatment methods comprising the administration of an FcRn antagonist, optionally in combination with standard-of-care treatment for ITP.

BACKGROUND OF THE INVENTION

Immune thrombocytopenia, sometimes referred to as immune thrombocytopenic purpura or idiopathic thrombocytopenia, and more generally as ITP, is characterized by a decrease of peripheral blood platelet counts to less than $100\times10^9$ per liter, as compared to $150\times10^9$ to $450\times10^9$ per liter in healthy individuals. ITP is an autoimmune disease wherein autoantibodies are formed to glycoproteins. The autoantibodies are believed both to interfere with platelet production and to accelerate platelet destruction. Depressed platelet counts in individuals may be transitory or persistent, and may stem from a variety of causes.

ITP with no identified associated causes or disorders is termed primary ITP, while ITP linked to other autoimmune or medical disorders is termed secondary ITP. Whereas ITP in adults typically has an insidious onset with no preceding viral or other illness and it normally follows a chronic course, ITP in children is usually short-lived with at least two-thirds recovering spontaneously within 6 months.

ITP can manifest itself by platelet-type bleeding (e.g., petechiae; purpura; conjunctival hemorrhage or other types of cutaneous bleeding). ITP can be associated with life-threatening complications such as intracranial bleeding. Even absent serious consequences, ITP patients suffer from a reduced quality of life, similar to other chronic diseases such as diabetes and rheumatoid arthritis.

In 2011 the American Society of Hematology (ASH) issued guidelines for the treatment of ITP. Neunert C et al., *Blood* 117: 4190-4207 (2011). In general five different approaches are available to the treating physician. In general treatment is considered necessary for patients having a platelet count persistently below $30\times10^9$/L.

One treatment approach is the use of immunosuppressive agents, such as corticosteroids. Most commonly used are prednisone (oral or IV), methylprednisone (also known as methylprednisolone), and dexamethasone.

A second approach is administration of intravenous immunoglobulin (IVIg) or anti-RhD immunoglobulin, the latter also known as Rho(D) immune globulin (anti-D). The American Society of Hematology recommends a combination of corticosteroids and IVIg if a rapid increase in platelet count is required. IVIg or anti-D is recommended when corticosteroids are contraindicated.

Corticosteroids, IVIg, and anti-D are considered first-line treatments. If first-line treatment fails, splenectomy is often considered, as the spleen plays a major role in platelet destruction. Another example of second-line treatment is the administration of a thrombopoietin receptor (TPO-R) agonist. Thrombopoietin (TPO) is an endogenous cytokine produced by the liver. It plays a major role in megakaryocyte growth and platelet delivery to circulation. Megakaryocytes and platelets present the TPO receptor. TPO-R agonists are believed to accelerate the production of platelets and their release into circulation.

At present three TPO-R agonists have been approved for use in the treatment of ITP: romiplostim, eltrombopag, and avatrombopag. Romiplostim is a fusion molecule comprising a TPO-R binding domain and a human Fc domain. The purpose of the Fc domain is to increase the half-life of the drug. Eltrombopag is a small molecule TPO-R agonist. Avatrombopag is another small molecule TPO-R agonist. A limitation of TPO-R agonists is that their long-term response rate is low (40-50%).

Yet another second-line treatment for ITP is fostamatinib, a small molecule inhibitor of spleen tyrosine kinase (Syk).

Rituximab (an anti-CD20 mAb) and alemtuzumab (an anti-CD52 mAb) are used in third-line treatment regimens.

Neonatal Fc receptor (FcRn) was originally characterized as a neonatal transport receptor for maternal IgG. It also functions in adults to protect IgG from degradation. FcRn binds to pinocytosed IgG and protects the IgG from transport to degradative lysosomes by recycling it back to the extracellular compartment.

FcRn antagonists, such as rozanolixizumab, which is a humanized, high-affinity, anti-human FcRn monoclonal antibody, have been suggested for use in an ITP treatment regimen. By binding to the FcRn receptor these molecules block the FcRn antibody salvaging mechanism, so that IgG antibodies, including pathogenic IgG antibodies, are cleared from circulation. If the autoantibodies involved in ITP are of the IgG class, FcRn antagonists may have a beneficial effect.

Apart from splenectomy, the many treatment options available today generally produce only short-term and modest improvements in the platelet counts of ITP patients. Thus, there is a need for a treatment regimen that offers more robust platelet count improvements than have been available to date. There is a particular need for a treatment regimen that improves long-term platelet responses in ITP patients, including those receiving standard treatment.

SUMMARY OF THE INVENTION

The present invention addresses these problems by providing a method of treating a human subject diagnosed with immune thrombocytopenia (ITP) comprising administering to the subject one or more doses of an FcRn antagonist. In certain embodiments, the method comprises administering to the subject one or more doses of an FcRn antagonist in combination with standard-of-care (SoC) treatment for ITP. In certain embodiments, the method further comprises administering to the subject one or more doses of at least one compound approved for SoC treatment for ITP.

Preferably a compound approved for standard-of-care treatment acts by a mechanism that is distinct from the mechanism of action of the FcRn antagonist. For example, corticosteroids, which act by dampening the immune system, can be used in combination with an FcRn antagonist. As another example, TPO-R agonists, which act by stimulating the production of platelets, can be used in combination with an FcRn antagonist.

An aspect of the invention is a method of treating a human subject diagnosed with immune thrombocytopenia (ITP), comprising administering to the subject one or more doses of a human FcRn (hFcRn) antagonist. Also provided is a human FcRn (hFcRn) antagonist for use in a method of treating immune thrombocytopenia (ITP) in a subject, the method comprising administering to the subject one or more doses of the hFcRn antagonist. In certain embodiments, the method further comprises administering to the subject one or more doses of at least one compound approved for standard-of-care treatment for ITP.

In certain embodiments, the hFcRn antagonist is an antibody or antibody fragment specifically binding to hFcRn. In certain embodiments, the antibody or antibody fragment comprises one or more CDRs specifically binding to hFcRn. In certain embodiments, the antibody or antibody fragment comprises a human Fc domain. In certain embodiments, the human Fc domain comprises one or more mutations that modify its binding to hFcRn. In certain embodiments, the one or more mutations comprise one or more of M252Y, S254T, T256E, H433K, and N434F (EU numbering). In certain embodiments, the one or more mutations comprise each of M252Y, S254T, T256E, H433K, and N434F (EU numbering). In certain embodiments, the human Fc domain comprises the mutations M252Y, S254T, T256E, H433K, and N434F (EU numbering).

In certain embodiments, the hFcRn antagonist is an isolated FcRn antagonist, wherein the FcRn antagonist consists of a variant Fc region consisting of two Fc domains which form a homodimer, wherein the amino acid sequence of each of the Fc domains consists of SEQ ID NO: 1.

In certain embodiments, the hFcRn antagonist is an isolated FcRn antagonist, wherein the FcRn antagonist consists of a variant Fc region consisting of two Fc domains which form a homodimer, wherein the amino acid sequence of each of the Fc domains consists of SEQ ID NO: 2.

In certain embodiments, the hFcRn antagonist is an isolated FcRn antagonist, wherein the FcRn antagonist consists of a variant Fc region consisting of two Fc domains which form a homodimer, wherein the amino acid sequence of each of the Fc domains consists of SEQ ID NO: 3.

In certain embodiments, the hFcRn antagonist is efgartigimod (ARGX-13).

An aspect of the invention is a method of treating a human subject diagnosed with immune thrombocytopenia (ITP), comprising administering to the subject one or more doses of a human FcRn (hFcRn) antagonist, wherein the hFcRn antagonist consists of a variant Fc region consisting of two Fc domains which form a homodimer, wherein the amino acid sequence of each of the Fc domains consists of SEQ ID NO: 1. Also provided is a human FcRn (hFcRn) antagonist for use in a method of treating immune thrombocytopenia (ITP) in a subject, the method comprising administering to the subject one or more doses of the hFcRn antagonist and wherein consists of a variant Fc region consisting of two Fc domains which form a homodimer, wherein the amino acid sequence of each of the Fc domains consists of SEQ ID NO: 1.

An aspect of the invention is a method of treating a human subject diagnosed with immune thrombocytopenia (ITP), comprising administering to the subject one or more doses of a human FcRn (hFcRn) antagonist, wherein the hFcRn antagonist consists of a variant Fc region consisting of two Fc domains which form a homodimer, wherein the amino acid sequence of each of the Fc domains consists of SEQ ID NO: 2. Also provided is a human FcRn (hFcRn) antagonist for use in a method of treating immune thrombocytopenia (ITP) in a subject, the method comprising administering to the subject one or more doses of the hFcRn antagonist and wherein consists of a variant Fc region consisting of two Fc domains which form a homodimer, wherein the amino acid sequence of each of the Fc domains consists of SEQ ID NO: 2.

An aspect of the invention is a method of treating a human subject diagnosed with immune thrombocytopenia (ITP), comprising administering to the subject one or more doses of a human FcRn (hFcRn) antagonist, wherein the hFcRn antagonist consists of a variant Fc region consisting of two Fc domains which form a homodimer, wherein the amino acid sequence of each of the Fc domains consists of SEQ ID NO: 3. Also provided is a human FcRn (hFcRn) antagonist for use in a method of treating immune thrombocytopenia (ITP) in a subject, the method comprising administering to the subject one or more doses of the hFcRn antagonist and wherein consists of a variant Fc region consisting of two Fc domains which form a homodimer, wherein the amino acid sequence of each of the Fc domains consists of SEQ ID NO: 3.

In certain embodiments, the hFcRn antagonist is efgartigimod (ARGX-113).

In certain embodiments, the method further comprises administering to the subject one or more doses of at least one compound approved for standard-of-care treatment for ITP. Thus, in an aspect, the invention is a method of treating a human subject diagnosed with immune thrombocytopenia (ITP), comprising administering to the subject one or more doses of a human FcRn (hFcRn) antagonist and one or more doses of at least one compound approved for standard-of-care treatment for ITP.

The following apply to each of the foregoing aspects and embodiments.

In certain embodiments, the hFcRn antagonist is administered in one or more doses of from about 10 nmol/kg to about 1000 nmol/kg.

In certain embodiments, the one or more doses of the hFcRn antagonist are in the range of from about 50 nmol/kg to about 300 nmol/kg.

In certain embodiments, the one or more doses of the hFcRn antagonist are in the range of from about 90 nmol/kg to about 200 nmol/kg.

In certain embodiments, the at least one compound approved for standard-of-care treatment for ITP comprises a corticosteroid. In certain embodiments, the corticosteroid is selected from the group consisting of oral prednisone, intravenous prednisone, dexamethasone, and any combination thereof.

In certain embodiments, the at least one compound approved for standard-of-care treatment for ITP comprises rituximab.

In certain embodiments, the at least one compound approved for standard-of-care treatment for ITP comprises alemtuzumab.

In certain embodiments, the at least one compound approved for standard-of-care treatment for ITP comprises fostamatinib.

In certain embodiments, the at least one compound approved for standard-of-care treatment for ITP is selected from the group consisting of cyclosporine, dapsone, and azathioprine.

In certain embodiments, the at least one compound approved for standard-of-care treatment for ITP comprises a thrombopoietin receptor agonist. In certain embodiments, the thrombopoietin receptor agonist is eltrombopag. In certain embodiments, the thrombopoietin receptor agonist is avatrombopag. In certain embodiments, the thrombopoietin receptor agonist is romiplostim. In certain embodiments, the thrombopoietin receptor agonist is a non-Fc portion of romiplostim.

In certain embodiments, the human subject has a platelet count prior to the treatment of less than $30 \times 10^9$/L.

In certain embodiments, the subject has a platelet count of $<100 \times 10^9$/L on standard-of-care treatment with at least one compound approved for standard-of-care treatment for ITP prior to treatment in accordance with a method of the invention. In certain embodiments, the subject has a platelet count of $\leq 50 \times 10^9$/L on standard-of-care treatment with at least one compound approved for standard-of-care treatment for ITP prior to treatment in accordance with a method of the invention. In certain embodiments, the subject has a platelet count of $\leq 30 \times 10^9$/L on standard-of-care treatment with at least one compound approved for standard-of-care treatment for ITP prior to treatment in accordance with a method of the invention. In certain embodiments, the subject has a platelet count of $\leq 20 \times 10^9$/L on standard-of-care treatment with at least one compound approved for standard-of-care treatment for ITP prior to treatment in accordance with a method of the invention. In certain embodiments, the subject has a platelet count of $\leq 10 \times 10^9$/L on standard-of-care treatment with at least one compound approved for standard-of-care treatment for ITP prior to treatment in accordance with a method of the invention.

In certain embodiments, the treatment results in an increase of the platelet count to more than $50 \times 10^9$/L. In certain embodiments, the increase of the platelet count to more than $50 \times 10^9$/L is sustained for at least 4 weeks.

In certain embodiments, the treatment results in an increase of the platelet count to more than $100 \times 10^9$/L. In certain embodiments, the increase of the platelet count to more than $100 \times 10^9$/L is sustained for at least 4 weeks.

As aspect of the invention is a method of treating a human subject diagnosed with immune thrombocytopenia (ITP), comprising administering to the subject one or more doses of a human FcRn (hFcRn) antagonist, wherein the hFcRn antagonist comprises an affibody specific for human FcRn. In certain embodiments, the hFcRn antagonist consists of an affibody specific for human FcRn. In certain embodiments, the affibody specific for human FcRn comprises the amino acid sequence set forth as SEQ ID NO: 4. In certain embodiments, the hFcRn antagonist is a fusion protein comprising an affibody specific for human FcRn linked to an albumin binding domain specific for human albumin. In certain embodiments, the affibody specific for human FcRn comprises the amino acid sequence set forth as SEQ ID NO: 4. In certain embodiments, the method further comprises administering to the subject one or more doses of at least one compound approved for standard-of-care treatment for ITP.

BRIEF DESCRIPTION OF THE DRAWINGS

FIG. 4A, IgG1; FIG. 4B, IgG2; FIG. 4C, IgG3; and FIG. 4D, IgG4.

DETAILED DESCRIPTION OF THE INVENTION

Figure 1:
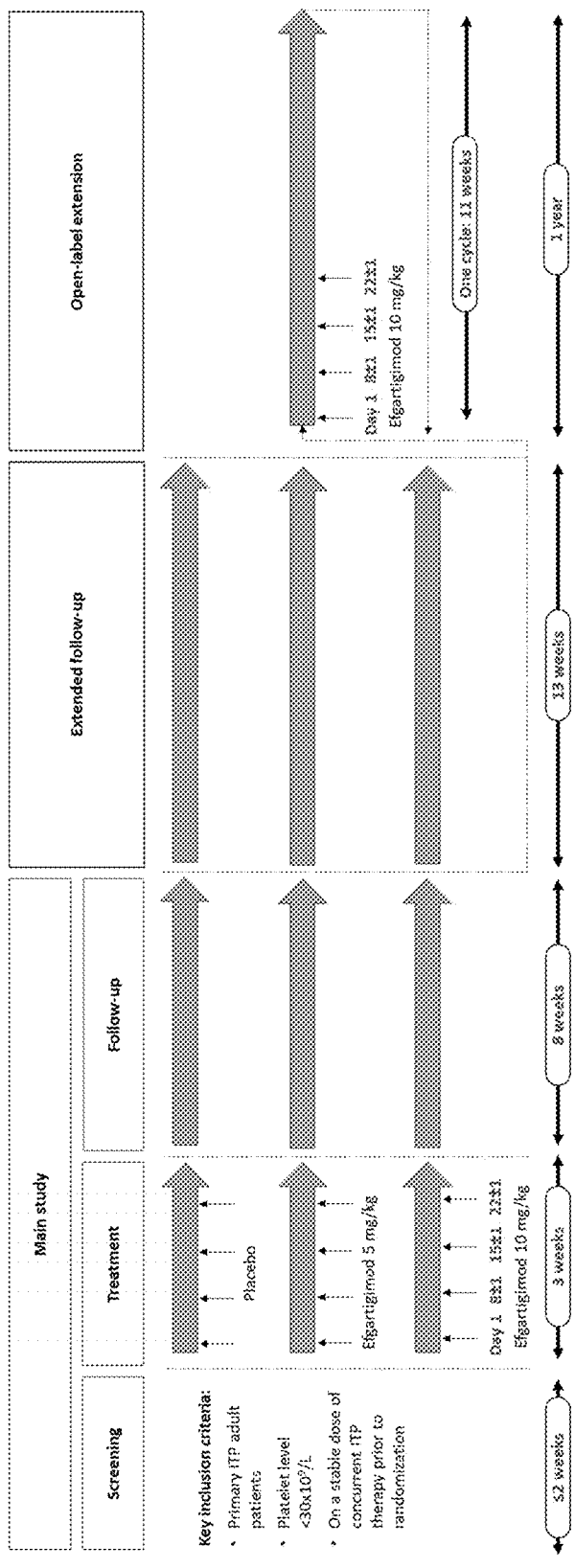
FIG. 1 depicts the design of the Phase 2 clinical trial described in Example 5.

The following is a detailed description of the invention.

Definitions

The term "ITP" as used herein refers to immune thrombocytopenia. ITP is an autoimmune disease or disorder in which pathogenic IgGs destroy platelet-producing cells (megakaryocytes) and circulating blood platelets (thrombocytes). Pathogenic IgGs drive disease progression in a multimodal approach: they accelerate platelet clearance, inhibit platelet production, directly induce platelet killing, and interfere with platelets' ability to perform their clotting function. Diagnosis of ITP generally is a diagnosis of exclusion requiring the presence of thrombocytopenia (circulating platelet count $<100 \times 10^9$/L) in the absence of other causes or disorders that may be associated with thrombocytopenia. Affected patients generally are at risk for spontaneous bleeding at platelet counts $<30 \times 10^9$/L, including life-threatening bleeding at platelet counts $<10 \times 10^9$/L. ITP can be acute or chronic. In certain individual embodiments, ITP can be categorized as newly diagnosed ITP, persistent ITP, or chronic ITP. Newly diagnosed ITP is ITP within three months of initial diagnosis. Persistent ITP is ITP lasting 3 to 12 months from diagnosis. Chronic ITP is ITP lasting more than 12 months from diagnosis. Rodeghiero F et al., *Blood* 113(11): 2386-2393 (2009).

As used herein, the phrase "standard-of-care treatment" in connection with ITP refers to any method of treatment generally recognized as being effective in the treatment of ITP. In certain embodiments, such standard-of-care treatment is in accordance with guidelines published by national or international authorities such as the American Society of Hematology. In certain embodiments, "standard-of-care treatment" entails taking a wait-and-see approach, i.e., monitoring clinical and laboratory parameters without treatment intervention while a subject has a platelet count >30×10$^9$/L and/or has no evidence of bleeding. In certain embodiments, "standard-of-care treatment" entails treatment intervention with one or more compounds discussed herein and/or splenectomy. For standard-of-care treatment involving intervention with one or more compounds, the one or more compounds can be administered on one or more occasions, and in the case of multiple occasions, each compound independently on a scheduled basis or on an as-needed basis.

The phrase "compound approved for standard-of-care treatment" as used herein means any compound that is generally recognized as being effective in the treatment of ITP. In 2011 the American Society of Hematology issued Guidelines for the treatment of ITP. Neunert C et al., *Blood* 117: 4190-4207 (2011). Any compound or class of compounds mentioned in these Guidelines is within the definition of "compound approved for standard-of-care treatment". These include, without limitation, corticosteroids, IVIg, anti-D, rituximab, and TPO-R agonists. Similarly, the International Consensus Report on the Investigation and Management of Primary Immune Thrombocytopenia of 2010 (Provan D et al., *Blood* 115: 168-186 (2010)) provides examples of compounds deemed to be within this definition. In accordance with the foregoing, a compound approved for standard-of-care treatment can also include any one or more of TPO-R agonists (e.g., romiplostim, eltrombopag, and avatrombopag), cyclosporine, azathioprine, fostamatinib, rituximab, and alemtuzumab. It will be understood that new compounds will be added to this definition as science progresses.

In certain embodiments, a "compound approved for standard-of-care treatment" as used herein excludes any one of the foregoing compounds that is generally recognized as being effective in the treatment of ITP, including, for example, any one or more of corticosteroids, IVIg, anti-D, TPO-R agonists (e.g., romiplostim, eltrombopag, and avatrombopag), cyclosporine, azathioprine, fostamatinib, rituximab, and/or alemtuzumab.

In certain embodiments, a compound approved for standard-of-care treatment excludes IVIg. In certain embodiments, a compound approved for standard-of-care treatment excludes anti-D. In certain embodiments, a compound approved for standard-of-care treatment excludes both IVIg and anti-D.

As used herein, the terms "treat," "treating," and "treatment" refer to therapeutic or preventative measures described herein. Methods of "treatment" employ administration to a subject an effective amount of an agent to prevent, cure, delay, reduce the severity of, or ameliorate one or more symptoms of a disease or disorder or recurring disease or disorder in the subject, or in order to prolong the survival of the subject beyond that expected in the absence of such treatment.

As used herein, the term "subject" refers to a mammal. In certain embodiments, a subject is a human. In certain embodiments, a human subject is an adult human at least 18 years of age. In certain embodiments, a human subject is at least 12 years of age but less than 18 years of age. In certain embodiments, a human subject is less than 12 years of age. In certain embodiments, a subject is a non-human primate.

As used herein, the term "FcRn" refers to a neonatal Fc receptor. In certain embodiments, the FcRn is a human FcRn (hFcRn). Human FcRn is well known, including its amino acid sequence, e.g., GenBank Accession No. NP_004098 encoded by the FCGRT gene as set forth in GenBank Accession No. NM-004017.

As used herein, the term "FcRn antagonist" refers to any agent that binds specifically to FcRn and inhibits the binding of immunoglobulin to the FcRn. In certain embodiments, the FcRn antagonist is a full length IgG antibody (e.g., rozanolixizumab). In certain embodiments, the FcRn antagonist is a fragment of an IgG antibody. In certain embodiments, the FcRn antagonist is an Fc fragment of an IgG antibody. In certain embodiments, the FcRn antagonist is efgartigimod (ARGX-113). As used herein, efgartigimod, also known as ARGX-113, is an isolated FcRn antagonist, wherein the FcRn antagonist consists of a variant Fc region consisting of two Fc domains which form a homodimer, wherein the amino acid sequence of each of the Fc domains consists of SEQ ID NO: 1. In certain embodiments, the FcRn antagonist consists of a variant Fc region consisting of two Fc domains which form a homodimer, wherein the amino acid sequence of each of the Fc domains consists of SEQ ID NO: 2. In certain embodiments, the FcRn antagonist consists of a variant Fc region consisting of two Fc domains which form a homodimer, wherein the amino acid sequence of each of the Fc domains consists of SEQ ID NO: 3. In certain embodiments, the FcRn antagonist is an affibody specific for human FcRn or a fusion protein comprising the affibody and an albumin binding domain (ABD). In certain embodiments, the affibody specific for human FcRn has an amino acid sequence set forth as SEQ ID NO: 4.

As used herein, the term "antibody" refers to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2, and CH3. Each light chain comprises a light chain variable region (abbreviated VL) and a light chain constant region. The light chain constant region comprises one domain (CL). The VH and VL regions can be further subdivided into regions of hypervariability, termed complementarity determining regions (CDRs), interspersed with regions that are more conserved, termed framework regions (FR).

As used herein, the term "Fc region" refers to the portion of a native immunoglobulin, e.g., IgG, formed by the Fc domains of its two heavy chains. A native Fc region is homodimeric.

As used herein, the term "Fc domain" refers generally to the portion of a single immunoglobulin heavy chain beginning in the hinge region just upstream of the papain cleavage site and ending at the C-terminus of the antibody. In the context of efgartigimod (ARGX-113), an Fc domain has an amino acid sequence set forth as SEQ ID NO: 1.

As used herein, the term "EU position" refers to the amino acid position in the EU numbering convention for the Fc region described in Edelman, G. M. et al., *Proc. Natl. Acad. Sci USA*, 63: 78-85 (1969) and Kabat et al, in "Sequences of Proteins of Immunological Interest," U.S. Dept. Health and Human Services, 5th edition, 1991.

Methods of the Invention

In its broadest aspect the present invention relates to a method of treating a human subject diagnosed with immune thrombocytopenia (ITP), the method comprising administering to the subject one or more doses of an FcRn antagonist. In certain embodiments, the FcRn antagonist is efgartigimod (ARGX-113). The present invention also provides a FcRn antagonist for use in a method of treating immune thrombocytopenia (ITP) in a subject, the method comprising administering to the subject one or more doses of the FcRn antagonist. In certain embodiments, the FcRn antagonist is a human FcRn (hFcRn) antagonist.

Thus, in certain embodiments, the present invention relates to a method of treating a human subject diagnosed with immune thrombocytopenia (ITP), the method comprising administering to the subject one or more doses of an FcRn antagonist, wherein the FcRn antagonist consists of a variant Fc region consisting of two Fc domains which form a homodimer, wherein the amino acid sequence of each of the Fc domains consists of SEQ ID NO: 1.

In certain embodiments, the present invention relates to a method of treating a human subject diagnosed with immune thrombocytopenia (ITP), the method comprising administering to the subject one or more doses of an FcRn antagonist, wherein the FcRn antagonist consists of a variant Fc region consisting of two Fc domains which form a homodimer, wherein the amino acid sequence of each of the Fc domains consists of SEQ ID NO: 2.

In certain embodiments, the present invention relates to a method of treating a human subject diagnosed with immune thrombocytopenia (ITP), the method comprising administering to the subject one or more doses of an FcRn antagonist, wherein the FcRn antagonist consists of a variant Fc region consisting of two Fc domains which form a homodimer, wherein the amino acid sequence of each of the Fc domains consists of SEQ ID NO: 3.

In certain embodiments, the method comprises administering to the subject one or more doses of an FcRn antagonist in conjunction with standard-of-care treatment for ITP. In this context, in certain embodiments, standard-of-care treatment for ITP specifically can be taking a wait-and-see approach to treatment of ITP, i.e., monitoring the patient without administering to the subject one or more doses of at least one compound approved for standard-of-care treatment for ITP. In certain embodiments, the FcRn antagonist is efgartigimod (ARGX-113).

In certain embodiments, the present invention relates to a method of treating a human subject diagnosed with immune thrombocytopenia (ITP), the method comprising administering to the subject one or more doses of an FcRn antagonist and one or more doses of at least one compound approved for standard-of-care treatment. In certain embodiments, the present invention relates to a FcRn antagonist for use in a method of treating immune thrombocytopenia (ITP) in a subject, wherein the method comprises administering to the subject one or more doses of the FcRn antagonist in combination with at least one compound approved for standard-of-care treatment for ITP. In certain embodiments, the FcRn antagonist is efgartigimod (ARGX-113).

In some embodiments, the methods of the invention comprise administering the FcRn antagonist without concurrent administration of one or more doses of at least one compound approved for standard-of-care treatment for ITP.

In some embodiments, the methods of the invention comprise administering the FcRn antagonist and concurrently administering a stable dosing regimen of one or more doses of at least one compound approved for standard-of-care treatment for ITP.

In some embodiments, the methods of the invention comprise administering the FcRn antagonist and concurrently administering a tapering dosing regimen of one or more doses of at least one compound approved for standard-of-care treatment for ITP. In some embodiments, the methods of the invention comprise administering the FcRn antagonist and concurrently administering a tapering dosing regimen of at least one compound approved for standard-of-care treatment for ITP.

In some embodiments, the methods of the invention comprise administering the FcRn antagonist and concurrently discontinuing a dosing regimen of one or more doses of at least one compound approved for standard-of-care treatment for ITP. In some embodiments, the methods of the invention comprise administering the FcRn antagonist and concurrently discontinuing a dosing regimen of at least one compound approved for standard-of-care treatment for ITP.

In certain embodiments, the subject is suffering from chronic ITP. In other embodiments, the subject is suffering from persistent ITP. In yet other embodiments, the subject is newly diagnosed with ITP. The FcRn antagonist may be a small molecule, an antibody, an antibody fragment, an affibody, or a nanobody that specifically binds to human FcRn (hFcRn). In certain embodiments the FcRn antagonist is an antibody or antibody fragment comprising one or more CDRs that specifically bind to hFcRn. Examples include full length monoclonal antibodies, such as rozanolixizumab (UCB-7665; UCB), DX-2504 (Dyax/Shire), DX-2507 (Dyax/Shire), HL161 (HanAll Biopharma Co., Ltd.). M281 (Momenta Pharmaceuticals), and SYNT001 (Syntimmune); and fragments of monoclonal antibodies, including FnAb-8 (Shanghai Jiao University). See, for example, WO 2009/131702; WO 2014/019727; WO 2014/204280; WO 2016/123521; WO 2016/183352; and WO 2017/121330. With respect to affibodies, see, for example, Seijsing J et al., *Sci Rep* 8: 5141 (2018). With respect to nanobodies, see, for example, Andersen J T et al., *Sci Rep* 3: 1118 (2013).

In a preferred embodiment, the FcRn antagonist is a human Fc region that has been engineered to modify its affinity to hFcRn. Examples include efgartigimod (ARGX-113), which is an isolated Fc region of a human IgG1 antibody, engineered for enhanced hFcRn affinity by the following mutations: M252Y, S254T, T256E, H433K, and N434F (EU numbering). Taken together, these mutations are the so-called "Abdeg" mutation, which result in enhanced Fc-FcRn binding at both pH 6.0 (acidified endosomal pH) and pH 7.4 (extracellular pH). The Abdeg mutation blocks binding of circulating IgG to FcRn and accelerates clearance of IgG through lysosomal degradation. See, for example, WO 2006/130834 and WO 2015/100289.

In certain embodiments, the FcRn antagonist consists of a variant Fc region consisting of two Fc domains which form a homodimer, wherein the amino acid sequence of each of the Fc domains consists of SEQ ID NO: 1.

In certain embodiments, the FcRn antagonist consists of a variant Fc region consisting of two Fc domains which form a homodimer, wherein the amino acid sequence of each of the Fc domains consists of SEQ ID NO: 2.

In certain embodiments, the FcRn antagonist consists of a variant Fc region consisting of two Fc domains which form a homodimer, wherein the amino acid sequence of each of the Fc domains consists of SEQ ID NO: 3.

Given the essential role of the FcRn receptor in IgG homeostasis, inhibiting this FcRn function, as achieved by efgartigimod, leads to rapid degradation of endogenous IgGs, which is expected to include autoantibodies in IgG-driven autoimmune diseases. This concept has been validated in various murine disease models together with pharmacokinetic/pharmaco-dynamic (PK/PD) studies in cynomolgus monkeys. Challa D K et al., *MAbs.* 5(5): 655-9 (2013). See also US 2015/0218239.

In murine in vivo disease models for rheumatoid arthritis and multiple sclerosis, a clear improvement in disease score was observed after treatment with an Abdeg-equipped molecule. This improvement was accompanied by systemic lowering of autoantibody levels. Patel D A et al., *J Immunol.* 187: 1015-22 (2011).

Pharmacokinetic and pharmacodynamic (PD) studies in cynomolgus monkeys confirmed the antibody-clearing properties of efgartigimod in a relevant animal model. A single infusion of efgartigimod resulted in a decrease of endogenous IgG up to 55% without altering serum albumin concentrations as well as IgM or IgA levels. This PD effect was proven to be more potent than IVIg, which is considered as a SoC therapy in ITP, both in rapidity of onset as in depth of the PD effect. Repeated dosing could improve the PD effect up to a maximum IgG reduction of 75%.

As mentioned above, efgartigimod is a variant Fc region consisting of two Fc domains which form a homodimer, wherein the amino acid sequence of each of the Fc domains is set forth as SEQ ID NO: 1.

```
                                            (SEQ ID NO: 1)
DKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALKFHYTQKSLSLSPG
```

In certain embodiments, the Fc domains of the variant Fc region of efgartigimod comprise an N-linked glycan having a bisecting GlcNAc (N-acetylglucosamine) at EU position 297 of the Fc domains.

A closely related variant Fc region consists of two Fc domains which form a homodimer, wherein the amino acid sequence of each of the Fc domains is set forth as SEQ ID NO: 2.

```
                                            (SEQ ID NO: 2)
DKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALKFHYTQKSLSLSPGK
```

Another closely related variant Fc region consists of two Fc domains which form a homodimer, wherein the amino acid sequence of each of the Fc domains is set forth as SEQ ID NO: 3.

```
                                            (SEQ ID NO: 3)
DKTHTCPPCPAPELLGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALKFHYTQKSLSLSPDSNLWN
```

It is customary to report the dosing of pharmaceutically active compounds in terms of weight of the compound, for example in mg, administered per kg of body weight of the human subject. Available hFcRn antagonists span a wide range of molecular weights. For example, the molecular weight of rozanolixizumab is about 150 kDa; that of efgartigimod is about 54 kDa. The mechanism of action is at the molecular level, making it more meaningful to express the dosing as nanomoles per kg body weight (nmol/kg). In any event, the skilled person can readily convert nmol/kg as used herein to mg/kg, if desired.

In certain embodiments, the hFcRn antagonist is administered in one or more doses of from about 10 nmol/kg to about 1000 nmol/kg. In general, the clinician aims to select the highest possible dose that does not unduly expose the subject to side effects. It has been found that rozanolixizumab is preferably administered in doses in the range of from about 20 nmol/kg to about 50 nmol/kg (i.e., about 3 mg/kg to about 7.5 mg/kg). Efgartigimod has been found to have a good safety profile and may be administered to human subjects in doses ranging from about 50 nmol/kg to about 300 nmol/kg (i.e., about 2.7 mg/kg to about 16.2 mg/kg), preferably from about 90 nmol/kg to about 200 nmol/kg (i.e., about 4.9 mg/kg to about 10.8 mg/kg).

In certain embodiments, the subject has newly diagnosed ITP. In certain embodiments, the subject has persistent ITP. In certain embodiments, the subject has chronic ITP.

In certain embodiments, the subject has a platelet count of $<100\times10^9$/L prior to treatment in accordance with a method of the invention. In certain embodiments, the subject has a platelet count of $\leq50\times10^9$/L prior to treatment in accordance with a method of the invention. In certain embodiments, the subject has a platelet count of $\leq30\times10^9$/L prior to treatment in accordance with a method of the invention. In certain embodiments, the subject has a platelet count of $\leq20\times10^9$/L prior to treatment in accordance with a method of the invention. In certain embodiments, the subject has a platelet count of $\leq10\times10^9$/L prior to treatment in accordance with a method of the invention.

In certain embodiments, the subject has a platelet count of $<100\times10^9$/L on standard-of-care treatment with at least one compound approved for standard-of-care treatment for ITP prior to treatment in accordance with a method of the invention. In certain embodiments, the subject has a platelet count of $\leq50\times10^9$/L on standard-of-care treatment with at least one compound approved for standard-of-care treatment for ITP prior to treatment in accordance with a method of the invention. In certain embodiments, the subject has a platelet count of $\leq30\times10^9$/L on standard-of-care treatment with at least one compound approved for standard-of-care treatment for ITP prior to treatment in accordance with a method of the invention. In certain embodiments, the subject has a platelet count of $\leq20\times10^9$/L on standard-of-care treatment with at least one compound approved for standard-of-care treatment for ITP prior to treatment in accordance with a method of the invention. In certain embodiments, the subject has a platelet count of $\leq10\times10^9$/L on standard-of-care treatment with at least one compound approved for standard-of-care treatment for ITP prior to treatment in accordance with a method of the invention.

In some embodiments, a subject to be treated in accordance with a method of the invention has ITP without clinical evidence of bleeding. In some embodiments, a subject to be treated in accordance with a method of the invention has ITP without clinical evidence of bleeding.

According to certain embodiments of the present invention, a human subject is administered an effective amount of the hFcRn antagonist alone, i.e., not in conjunction with administration of any compound or compounds approved for standard-of-care treatment for ITP. For example, a subject having ITP with a platelet count >30×10$^9$/L and/or without evidence of bleeding can be administered an effective amount of the hFcRn antagonist to treat the ITP. According to such embodiments, the method comprises administering to the subject one or more doses of a human FcRn (hFcRn) antagonist while on wait-and-see approved standard-of-care treatment for ITP. In certain embodiments, the FcRn antagonist is efgartigimod (ARGX-113).

According to certain other embodiments of the present invention, the human subject is administered at least one compound approved for standard-of-care treatment for ITP, in addition to the hFcRn antagonist. The hFcRn antagonist and the at least one compound approved for standard-of-care treatment may be administered jointly or separately. They may be administered closely together in time, or their administrations may be staggered. When they are administered separately, in certain embodiments the hFcRn antagonist is administered before the compound or compounds approved for standard-of-care treatment for ITP. When they are administered separately, in certain embodiments the compound or compounds approved for standard-of-care treatment for ITP is or are administered before the hFcRn antagonist. The hFcRn antagonist and the at least one compound approved for standard-of-care treatment may be administered by the same or different routes of administration.

In certain embodiments, a compound approved for standard-of-care treatment for ITP may comprise a corticosteroid, such as oral or intravenous prednisone, methylprednisone, dexamethasone, and combinations thereof. In certain embodiments, a compound approved for standard-of-care treatment for ITP may consist of a corticosteroid, such as oral or intravenous prednisone, methylprednisone, dexamethasone, and combinations thereof. In certain embodiments, a compound approved for standard-of-care treatment for ITP may exclude a corticosteroid, such as oral or intravenous prednisone, methylprednisone, dexamethasone, and combinations thereof.

In certain embodiments, a compound approved for standard-of-care treatment for ITP may comprise IVIg or anti-D. In certain embodiments, a compound approved for standard-of-care treatment for ITP may consist of IVIg. In certain embodiments, a compound approved for standard-of-care treatment for ITP may consist of anti-D. In certain embodiments, a compound approved for standard-of-care treatment for ITP may exclude IVIg. In certain embodiments, a compound approved for standard-of-care treatment for ITP may exclude anti-D. In certain embodiments, a compound approved for standard-of-care treatment for ITP may exclude both IVIg and anti-D.

In certain embodiments, a compound approved for standard-of-care treatment for ITP may comprise cyclosporine. In certain embodiments, a compound approved for standard-of-care treatment for ITP may consist of cyclosporine. In certain embodiments, a compound approved for standard-of-care treatment for ITP may exclude cyclosporine.

In certain embodiments, a compound approved for standard-of-care treatment for ITP may comprise dapsone. In certain embodiments, a compound approved for standard-of-care treatment for ITP may consist of dapsone. In certain embodiments, a compound approved for standard-of-care treatment for ITP may exclude dapsone.

In certain embodiments, a compound approved for standard-of-care treatment for ITP may comprise azathioprine. In certain embodiments, a compound approved for standard-of-care treatment for ITP may consist of azathioprine. In certain embodiments, a compound approved for standard-of-care treatment for ITP may exclude azathioprine.

In certain embodiments, a compound approved for standard-of-care treatment for ITP may comprise rituximab. In certain embodiments, a compound approved for standard-of-care treatment for ITP may consist of rituximab. In certain embodiments, a compound approved for standard-of-care treatment for ITP may exclude rituximab.

In certain embodiments, a compound approved for standard-of-care treatment for ITP may comprise alemtuzumab. In certain embodiments, a compound approved for standard-of-care treatment for ITP may consist of alemtuzumab. In certain embodiments, a compound approved for standard-of-care treatment for ITP may exclude alemtuzumab.

In certain embodiments, a compound approved for standard-of-care treatment for ITP may comprise fostamatinib. In certain embodiments, a compound approved for standard-of-care treatment for ITP may consist of fostamatinib. In certain embodiments, a compound approved for standard-of-care treatment for ITP may exclude fostamatinib.

In certain embodiments, a compound approved for standard-of-care treatment for ITP may comprise one or more TPO-R agonists, e.g., romiplostim, eltrombopag, and avatrombopag. In certain embodiments, a compound approved for standard-of-care treatment for ITP may consist of one or more TPO-R agonists, e.g., romiplostim, eltrombopag, and avatrombopag. In certain embodiments, a compound approved for standard-of-care treatment for ITP may exclude one or more TPO-R agonists, e.g., romiplostim, eltrombopag, and avatrombopag.

In certain embodiments, the at least one compound approved for standard-of-care treatment for ITP consists of a single compound. In certain embodiments, the at least one compound approved for standard-of-care treatment for ITP consists of two compounds, from the same or different classes. In certain embodiments, the at least one compound approved for standard-of-care treatment for ITP consists of three compounds, from one, two, or three classes. In certain embodiments, the at least one compound approved for standard-of-care treatment for ITP consists of four or more compounds, from one, two, three, or four or more classes.

Exemplary classes of compounds approved for standard-of-care treatment for ITP include (i) broadly immunosuppressive agents such as corticosteroids, cyclosporine, and azathioprine; (ii) preparations of naturally occurring immunoglobulin, such as IVIg and anti-D; (iii) antigen-specific monoclonal antibodies, such as rituximab and alemtuzumab; (iv) TPO-R agonists, such as eltrombopag, romiplostim, and avatrombopag; and (v) small molecule inhibitors of spleen tyrosine kinase (Syk), such as fostamatinib (Tavalisse). Rozanolixizumab is currently in clinical trials for ITP in adult humans.

For example, in certain embodiments, the method comprises administering to the subject one or more doses of a hFcRn antagonist and one or more doses of a corticosteroid.

As another example, in certain embodiments, the method comprises administering to the subject one or more doses of a hFcRn antagonist, one or more doses of a corticosteroid, and one or more doses of a TPO-R agonist.

In embodiments calling for more than a single compound approved for standard-of-care treatment for ITP, the two or more compounds approved for standard-of-care treatment for ITP may be administered on the same or different schedules. Furthermore, in embodiments calling for more than a single compound approved for standard-of-care treatment for ITP, the two or more compounds approved for standard-of-care treatment for ITP may be administered independently on the same or different schedules from that of the FcRn antagonist. Yet further, in embodiments calling for more than a single compound approved for standard-of-care treatment for ITP, the two or more compounds approved for standard-of-care treatment for ITP may be administered independently in their original or different amounts (e.g., reduced amounts), and on the same or different schedules from that of the FcRn antagonist.

It will be understood that some of these combinations can be expected to be more effective than others. For example, corticosteroids are believed to decrease the production of autoantibodies, which complements the action of the hFcRn antagonist of clearing the autoantibodies from the patient's body. In accordance with the instant invention, the combination of corticosteroids and hFcRn antagonist has indeed been found to be beneficial.

On the other hand, the mechanisms of IVIg and the hFcRn antagonist are believed to be similar insofar as they both bind to FcRn and act as competitive inhibitors of FcRn-mediated IgG recycling. The effect of IVIg may be compromised by that of the hFcRn antagonist, the latter being more efficient.

Combined administration according to the method of the instant invention may take any of a variety of forms. In an embodiment a human subject diagnosed with ITP initially receives standard-of-care treatment comprising administration of at least one compound approved for standard-of-care treatment for ITP. If this treatment does not, or does not sufficiently, elevate the patient's platelet count, administration of a hFcRn antagonist is commenced. At this time the administration of the at least one compound approved for standard-of-care treatment for ITP may be discontinued. Alternatively, at this time the administration of the at least one compound approved for standard-of-care treatment for ITP may be continued, but at a reduced administration rate (i.e., reduced amount and/or frequency). In yet another embodiment, at this time the administration of the at least one compound approved for standard-of-care treatment for ITP may continue unchanged while the patient receives the hFcRn antagonist.

In certain embodiments, the FcRn antagonist is administered periodically in an ongoing manner, e.g., one or more doses can be administered every two, three, four, five, six, seven, or eight or more weeks. The time between such repeated administrations can be set by schedule or by monitoring clinical and/or laboratory parameters such as presence or absence of bleeding and/or platelet count falling at or below a specified threshold level, e.g., $10 \times 10^9$/L, $15 \times 10^9$/L, $20 \times 10^9$/L, $25 \times 10^9$/L, or $30 \times 10^9$/L.

In certain embodiments, one or more doses of the FcRn antagonist is administered every two weeks. In certain embodiments, one or more doses of the FcRn antagonist is administered every three weeks. In certain embodiments, one or more doses of the FcRn antagonist is administered every four weeks. In certain embodiments, one or more doses of the FcRn antagonist is administered every five weeks. In certain embodiments, one or more doses of the FcRn antagonist is administered every six weeks. In certain embodiments, one or more doses of the FcRn antagonist is administered every seven weeks. In certain embodiments, one or more doses of the FcRn antagonist is administered every eight or more weeks.

In certain embodiments, one or more doses of the FcRn antagonist is administered every two weeks after completing an initial treatment period comprising four administrations of the FcRn antagonist over three weeks. In certain embodiments, one or more doses of the FcRn antagonist is administered every three weeks after completing an initial treatment period comprising four administrations of the FcRn antagonist over three weeks. In certain embodiments, one or more doses of the FcRn antagonist is administered every four weeks after completing an initial treatment period comprising four administrations of the FcRn antagonist over three weeks. In certain embodiments, one or more doses of the FcRn antagonist is administered every five weeks after completing an initial treatment period comprising four administrations of the FcRn antagonist over three weeks. In certain embodiments, one or more doses of the FcRn antagonist is administered every six weeks after completing an initial treatment period comprising four administrations of the FcRn antagonist over three weeks. In certain embodiments, one or more doses of the FcRn antagonist is administered every seven weeks after completing an initial treatment period comprising four administrations of the FcRn antagonist over three weeks. In certain embodiments, one or more doses of the FcRn antagonist is administered every eight or more weeks after completing an initial treatment period comprising four administrations of the FcRn antagonist over three weeks.

In certain embodiments the administrations of the hFcRn antagonist and the at least one compound approved for standard-of-care treatment for ITP may be contemporaneous or staggered. Alternatively, the administration of the at least one compound approved for standard-of-care treatment for ITP may be tapered down after the administration of the hFcRn antagonist has commenced. Other permutations will be apparent to the skilled person. In general, the patient's platelet count will be monitored, allowing for the treatment regimen to be personalized.

Combined administration of a hFcRn antagonist and a TPO-R agonist has been found, in accordance with the instant invention, to be effective in increasing platelet counts in human subjects diagnosed with ITP. Without wishing to be bound by theory, the instant inventors believe that this is the result of the fact that the modes of action of these agents are entirely different.

The FcRn antagonist can be administered by any suitable route or routes of administration. In certain embodiments, the FcRn antagonist is administered intravenously. In certain embodiments, the FcRn antagonist is administered intraperitoneally. In certain embodiments, the FcRn antagonist is administered subcutaneously.

For example, efgartigimod (ARGX-113) can be administered by any suitable route or routes of administration. In certain embodiments, the FcRn antagonist is administered intravenously. In certain embodiments, the FcRn antagonist is administered intraperitoneally. In certain embodiments, the FcRn antagonist is administered subcutaneously.

For subcutaneous administration, in certain embodiments the FcRn antagonist is an aqueous formulation comprising about 100-200 mg/mL efgartigimod (ARGX-113) in 20 mM histidine/histidine HCl, 60 mM sucrose, 100 mM NaCl, and 0.02%-0.04% (w/v) polysorbate 20 or polysorbate 80, pH 6.0, wherein ARGX-113 is an isolated FcRn antagonist consisting of a variant Fc region, wherein said variant Fc region consists of two Fc domains which form a homodimer, wherein the amino acid sequence of each of the Fc domains consists of SEQ ID NO: 1.

For subcutaneous administration, in certain embodiments the FcRn antagonist is an aqueous formulation comprising 150 mg/mL efgartigimod (ARGX-113) in 20 mM histidine/histidine HCl, 60 mM sucrose, 100 mM NaCl, and 0.04% (w/v) polysorbate 20, pH 6.0.

For subcutaneous administration, in certain embodiments the FcRn antagonist is an aqueous formulation comprising 175 mg/mL efgartigimod (ARGX-113) in 20 mM histidine/histidine HCl, 60 mM sucrose, 100 mM NaCl, and 0.04% (w/v) polysorbate 20, pH 6.0.

For subcutaneous administration, in certain embodiments the FcRn antagonist is an aqueous formulation comprising water, 200 mg/mL efgartigimod (ARGX-113) in 20 mM histidine/histidine HCl, 60 mM sucrose, 100 mM NaCl, and 0.04% (w/v) polysorbate 20, pH 6.0.

For subcutaneous administration, in certain embodiments the FcRn antagonist is an aqueous formulation comprising about 100-200 mg/mL efgartigimod (ARGX-113) in 20 mM histidine/histidine HCl, 60 mM sucrose, 100 mM NaCl, 10 mM L-methionine, and 0.02%-0.04% (w/v) polysorbate 20 or polysorbate 80, pH 6.0.

For subcutaneous administration, in certain embodiments the FcRn antagonist is an aqueous formulation comprising 165 mg/mL efgartigimod (ARGX-113) in 20 mM histidine/histidine HCl, 60 mM sucrose, 100 mM NaCl, 10 mM L-methionine, and 0.04% (w/v) polysorbate 20, pH 6.0.

For subcutaneous administration, in certain embodiments the FcRn antagonist is an aqueous formulation comprising 175 mg/mL efgartigimod (ARGX-113) in 20 mM histidine/histidine HCl, 60 mM sucrose, 100 mM NaCl, 10 mM L-methionine, and 0.03% (w/v) polysorbate 20, pH 6.0.

For subcutaneous administration, in certain embodiments the FcRn antagonist is an aqueous formulation comprising 200 mg/mL efgartigimod (ARGX-113) in 20 mM histidine/histidine HCl, 60 mM sucrose, 100 mM NaCl, 10 mM L-methionine, and 0.03%0 (w/v) polysorbate 20, pH 6.0.

For subcutaneous administration, in certain embodiments the FcRn antagonist is an aqueous formulation comprising about 100-200 mg/mL efgartigimod (ARGX-113) in 50 mM histidine/histidine HCl, 60 mM sucrose, 100 mM arginine HCl, and 0.02%/-0.04% (w/v) polysorbate 20 or polysorbate 80, pH 6.0.

For subcutaneous administration, in certain embodiments the FcRn antagonist is an aqueous formulation comprising about 100-200 mg/mL efgartigimod (ARGX-113) in 20 mM histidine/histidine HCl, 60 mM sucrose, 100 mM arginine HCl, 10 mM L-methionine, and 0.02%-0.04% (w/v) polysorbate 20 or polysorbate 80, pH 6.0.

For subcutaneous administration, in certain embodiments the FcRn antagonist is an aqueous formulation comprising 175 mg/mL efgartigimod (ARGX-113) in 20 mM histidine/histidine HCl, 60 mM sucrose, 100 mM arginine HCl, 10 mM L-methionine, and 0.03% (w/v) polysorbate 20, pH 6.0.

For subcutaneous administration, in certain embodiments the FcRn antagonist is an aqueous formulation comprising 200 mg/mL efgartigimod (ARGX-113) in 20 mM histidine/histidine HCl, 60 mM sucrose, 100 mM arginine HCl, 10 mM L-methionine, and 0.03% (w/v) polysorbate 20, pH 6.0.

Antiplatelet autoantibodies are believed to negatively affect the platelet count in at least two ways. Houwerzijl E J, *Blood* 103: 500-506 (2004); Kuter D J et al., *Hematol Oncol Clin North Am* 23: 1193-1211 (2009). Such antibodies are believed to bind to megakaryocytes, which leads to their apoptosis. As a result there are fewer megakaryocytes capable of producing platelets. In a second mode of action, such autoantibodies bind to newly formed platelets. These platelets painted with autoantibodies are removed by the spleen. Plasma levels of TPO are regulated by binding of TPO to circulating platelets which results in its removal from circulation and subsequent degradation. Stasi R et al., *Blood Rev* 24(4-5): 179-90 (2010). As a result, the autoantibodies cause a TPO deficiency.

By removing autoantibodies from circulation, the hFcRn antagonist increases the available TPO. The TPO-R agonist makes the available TPO more effective. Thus, the administration of hFcRn antagonist reinforces or amplifies the effect of the TPO-R agonist, and vice versa.

Accordingly, in certain embodiments, the method of treatment comprises the administration of a TPO-R agonist and a hFcRn antagonist. At this time preferred TPO-R agonists are eltrombopag, romiplostim, and avatrombopag.

Eltrombopag (e.g., PROMACTA®, Novartis) is a small molecule (MW ca. 442 Da), and its pharmacokinetics are believed not to be affected by the co-administration of the hFcRn antagonist.

Similar to eltrombopag, avatrombopag (e.g., DOPTELET®, Dova Pharmaceuticals) is a small molecule (MW ca. 650 Da), and its pharmacokinetics are believed not to be affected by the co-administration of the hFcRn antagonist.

Romiplostim (e.g., NPLATE®, Amgen) is a fusion molecule comprising an Fc domain for improved half-life. The effect of the Fc domain is counteracted by the hFcRn antagonist. For co-administration with a hFcRn antagonist, the romiplostim molecule may be modified by, for example, not including the Fc domain portion and retaining the TPO-R binding portion. This results in a smaller molecule that is easier to manufacture and to administer.

EXAMPLES

Example 1: Single-Dose Toxicity Study of ARGX-113 in Cynomolgus Monkeys

ARGX-113 was administered by a 2-hour IV infusion to cynomolgus monkeys at four dose levels (10, 30, 50, and 100 mg/kg body weight [b.w.]) and controls. No ARGX-113-related signs of local intolerance were noted at any of the tested dose levels. No ARGX-113-related effects were noted on behavior, body weight, food consumption, electrocardiographic parameters, circulatory functions, hematological parameters, lymphocyte typing, urinary parameters, ophthalmological and auditory functions, and organ weights of any of the animals at any dose level. In addition, no macroscopic or microscopic systemic organ changes were noted in any of the animals examined, in particular no histopathological changes were noted in livers of the monkeys at any tested dose level.

Administration of ARGX-113 resulted in significant changes in biochemical parameters, which were considered not to be adverse in nature. A decrease in serum concentrations of γ-globulins was noted in all ARGX-113-treated groups. As ARGX-113 enhances antibody clearance by binding to FcRn-receptor, a reduction of the overall immunoglobulins (γ-globulin fraction) was not considered to be an adverse effect and should be considered related to ARGX-13 mechanism of action. Accordingly, reduction in γ-globulin resulted in a decrease of the overall globulins of the IgG isotype and an increase in the albumin/globulin ratios.

However, no such decreases were noted for IgM, IgA, or albumin levels as compared to the control group.

On the basis of these observations, the No Observed Adverse Effect Level (NOAEL) of ARGX-13 was 100 mg/kg b.w.

Example 2: Repeated-Dose Toxicity Study of ARGX-113 in Cynomolgus Monkeys

In the repeat dose one-month toxicology study in cynomolgus monkeys, ARGX-113 was administered at 3 dose levels (3, 30, and 100 mg/kg). Ten animals, 5 male and 5 female cynomolgus monkeys, were treated at each dose level and received IV infusions every 48 hours with ARGX-113 for a total of 15 infusions. ARGX-113 was well tolerated at all doses by all animals as determined by clinical signs, body weight, macroscopic examination, histopathology, food consumption, and hematology and serum biochemistry parameters. No macroscopic ARGX-113-related changes were observed. The histopathological examination revealed liver changes at doses of 100 mg/kg ARGX-113. Liver changes included cytoplasmic alterations and degeneration, and diffuse mixed inflammatory cell infiltrates. There was no liver pathology in animals in the 100 mg/kg dose group at the end of the treatment-free recovery phase. No apparent ARGX-113-related changes were observed for the 3 mg/kg or 30 mg/kg dose groups.

The NOAEL in this study was therefore considered to be 30 mg/kg.

In the chronic 26-week toxicity study in cynomolgus monkeys, ARGX-113 was administered by repeated 30-min I.V. infusion to 24 male and 24 female cynomolgus monkeys. Reversibility of any effect was assessed after a recovery period of at least 8 weeks. ARGX-113 or vehicle was administered once every week for 26 weeks at doses of 0 (vehicle), 10, 30, and 100 mg/kg.

There were no effects of ARGX-113 on clinical signs, body weight, food consumption, ECGs, circulatory functions, coagulation, urinary status, ophthalmological and auditory functions, relative and absolute organ weights, and myeloid to erythroid ratio at any study dose level. No animal died prematurely during the study.

No ARGX-113-related signs of local intolerance were reported for any of the treated animals.

The administration of ARGX-113 resulted in significant changes in biochemical parameters, which were considered not to be adverse in nature when following a similar rationale to that described for previous toxicity studies.

Lymphocyte typing did not reveal ARGX-113-related change in composition or grade of activation of the investigated cell subsets (NK cells, T-helper cells, activated T-helper cells, cytotoxic T-cells, activated cytotoxic T-cells, immature T cells, and B cells). No ARGX-113-related changes in hematological parameters were observed.

No macroscopic or microscopic adverse test item-related changes were reported for any of the animals examined.

From these observations, the NOAEL of ARGX-113 was 100 mg/kg administered once weekly by a 30-min IV infusion.

Example 3: Repeated-Dose Toxicity Study of ARGX-113 in Rats

In the repeat dose one-month toxicology study in rats, ARGX-113 was administered at 3 dose levels (10, 30, and 100 mg/kg). Twenty animals, ten male and ten female animals, were treated at each dose level and received IV injection every 48 hours with ARGX-113 for a total of 15 infusions. ARGX-113 was well tolerated at all doses by all animals as determined by clinical signs, body weight, macroscopic examination, histopathology, food consumption, and hematology and serum biochemistry parameters. No macroscopic ARGX-113-related changes were observed. The histopathological examination revealed test item-related histopathological lesion in the liver at doses of 100 mg/kg ARGX-113 in some animals. This lesion consisted of Kupffer cell hypertrophy/hyperplasia which was observed in both sexes of the group treated with 100 mg/kg of ARGX-113. There was no liver pathology in animals in the 100 mg/kg dose group at the end of the treatment-free recovery phase. No apparent ARGX-113-related changes were observed for the 10 mg/kg or 30 mg/kg dose groups.

The NOAEL in this study was therefore considered to be 30 mg/kg.

Example 4: Phase 1 Dose-Escalation Clinical Trial of Efgartigimod in Healthy Humans In a Phase 1 dose-escalation study in healthy humans, after single IV administration of efgartigimod (ARGX-113) at doses of 0.2, 2.0, 10, 25 and 50 mg/kg, $C_{max}$ of efgartigimod increased more than dose-proportionally between 0.2 and 10 mg/kg (with a 115-fold increase for a 50-fold dose increase), and then overall dose-proportionally over 10 to 50 mg/kg (with a 5.6-fold increase, for a 5-fold dose increase). The $AUC_{0-96\ h}$ of efgartigimod increased more than dose proportionally between 0.2 and 2.0 mg/kg (with a 16.6-fold increase for a 10-fold dose increase). Both $AUC_{0-96\ h}$ and $AUC_{0-\infty}$ increased overall dose-proportionally over 2.0 to 50 mg/kg (with a 23.5- and 25.1-fold increase, respectively, for a 25-fold dose increase).

In all cohorts, median time to reach $C_{max}$ was 2.0 h (i.e., the end of the infusion). The half-life of efgartigimod was of about 85.1 h to 104 h over 2.0 to 50 mg/kg and about 140 h in the 0.2 mg/kg dose group (however, most likely the terminal phase was not yet reached).

Efgartigimod was not quantifiable in urine over the 0-72 h period after single IV administration of efgartigimod at doses of 0.2 and 2.0 mg/kg. At the higher tested dose levels, the excretion of efgartigimod in urine was very low (<0.1%) and rapid (from 55 to 100% within the first 12 h).

In the multiple ascending dose phase of the study the pharmacokinetics (PK) of efgartigimod after the first administration in all treatment groups was consistent with what was observed in the single ascending dose phase of the study.

Overall, no accumulation of efgartigimod was observed after q4d dosing for 21 days and q7d dosing for 22 days, with accumulation ratio ($R_{ac}$) geometric mean values ranging from 0.814 to 1.26. The PK profiles after the last dosing day (i.e., after multiple administrations) were similar than after the first dose.

After a single administration of efgartigimod, a reduction of total IgG level in serum was observed for all the dose groups compared to subjects who received placebo, except at the lowest dose (0.2 mg/kg). Mean maximal reduction ($E_{max}$) was the highest (from 53.1 to 62.8%) when efgartigimod was given at doses over 10 to 50 mg/kg. A dose/response effect occurred not only at level of the reduction observed, but also on the duration of the reducing effect, covering 96 h to 336 h postdose for the 2.0 mg/kg dose and from 48 h to the last sample collection time (i.e., 672 h postdose) for the doses over 10 to 50 mg/kg. Thus, the higher doses resulted in a more sustained reduction of total IgG in serum.

In general manner, the different IgG subtypes (1, 2, 3, and 4) had their serum level reduced in a similar extent, although of a bit lesser extent for the subtype 4.

A reduction of total IgG level was observed after a single administration of efgartigimod compared to placebo. At both dose levels (10 and 25 mg/kg) this inhibition was enhanced after multiple administrations of efgartigimod.

Following multiple administrations of 10 mg/kg q4d, 10 mg/kg q7d, or 25 mg/kg q7d efgartigimod, the respective mean $E_{max}$ ranged from 69.4 to 77.5%. In general manner, the different IgG subtypes (1, 2, 3, and 4) had their serum level reduced in a similar extent, although of a bit lesser extent for the subtype 4.

The extent of total IgG level reduction in serum was not significantly different between the tested doses or regimens, suggesting that the maximal reduction of total IgG level by efgartigimod was already reached with the 10 mg/kg dose q7d. This was also reflected in the IgG subtype levels, except for the IgG subtype 2.

A correlation could be observed between efgartigimod overall systemic exposure and pharmacodynamics (PD) effect in terms of decrease in total IgG serum levels (area under the effect curve (AUEC). Similar results were observed for the IgG subtypes (1, 2, 3 and 4).

The administration of efgartigimod did not induce a relevant decrease in IgA, IgD, IgE, and IgM serum levels.

The most frequently reported treatment-emergent adverse events (TEAEs) after a single administration of efgartigimod at doses of 0.2, 2.0, 10, 25, and 50 mg/kg or placebo were abnormal differential white blood cell (WBC) count, increased C-reactive protein (CRP), headache, dizziness, and chills.

The events of CRP increase were considered moderate in severity in the 25 mg/kg efgartigimod dose group and mild in severity in the 50 mg/kg efgartigimod dose group. The TEAE chills was reported as moderate in 1 subject (50 mg/kg efgartigimod). All other reported TEAEs were considered mild in severity.

All events of abnormal differential WBC count, increased CRP, headache, dizziness, and chills were considered related to the study drug by the investigator in the highest dose groups (i.e., 25 and 50 mg/kg) only. The reported events of abnormal differential WBC count were associated with immunological laboratory abnormalities of decreased CD8, CD3, CD56, CD4 and CD19 lymphocyte levels.

Following multiple dosing of 10 mg/kg q4d the most frequently reported TEAEs were diarrhea and nasopharyngitis. The most frequently reported TEAEs for the subjects who received efgartigimod either 10 or 25 mg/kg q7d included headache, feeling cold, chills, fatigue, somnolence, nasopharyngitis, back pain and catheter site pain. The TEAEs feeling cold, back pain, chills, fatigue and somnolence were only reported at the highest dose (25 mg/kg q7d). Headache was considered related to the study drug by the investigator in 3 subjects (all 25 mg/kg q7d) and for one of these subjects the headache was of moderate severity. All events of feeling cold, chills and fatigue were considered mild and related to the study drug by the investigator. No notable changes of lymphocyte subsets were reported in the multiple dose groups. One serious adverse event (SAE) of hyperventilation was observed in the 25 mg/kg q7d group which was considered unlikely related to the study medication. It should be noted that none of the TEAEs in this Phase 1 study were considered certainly related to the study drug according to the investigator.

With the exception of transient, out-of-range values of CRP and some lymphocyte subsets that were reported as TEAEs, laboratory results did not show clinically relevant changes. No clinically relevant changes were observed in electrocardiograms (ECGs).

Example 5: Phase 2 Clinical Trial of Efgartigimod in Humans with Primary ITP

Figure 2:
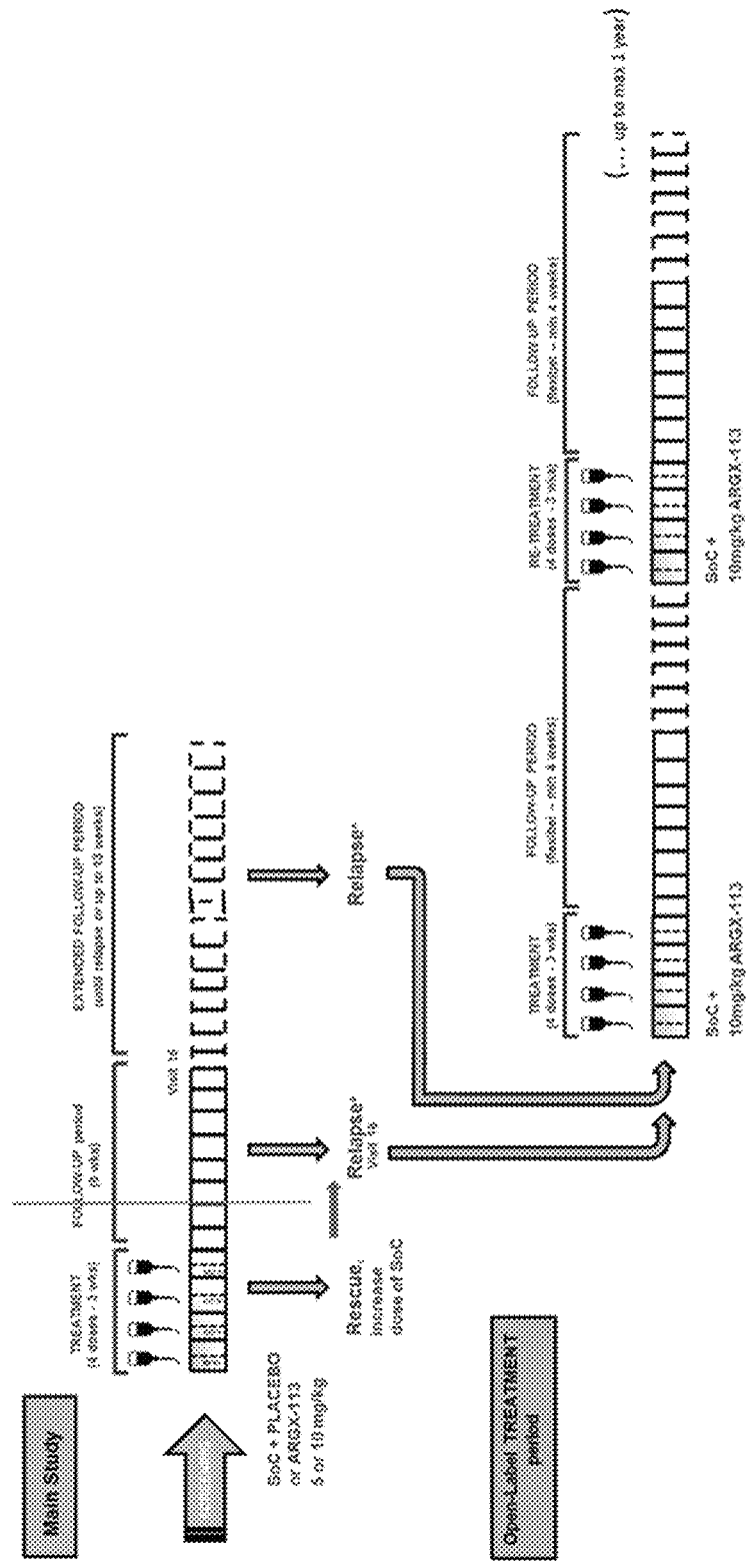
FIG. 2 depicts the design of the open-label extension portion of the clinical trial described in Example 6.

This example describes a completed randomized, double-blind, placebo-controlled Phase 2 study to evaluate the safety, efficacy, pharmacokinetics, and pharmacodynamics of efgartigimod in patients with primary immune thrombocytopenia (main study), followed by an optional open-label extended treatment period (described in Example 6). FIG. 1 shows the overall design of the study. FIG. 2 shows the design of the open-label study.

Study Design

Briefly, the main study involved a randomized, double-blind, placebo-controlled Phase 2 study which included a 2-week screening period, a 3-week treatment period and 8-week follow-up (FU) period. After amendment of the protocol, patients who completed the initial 8-week FU period with a platelet count ≥30×10$^9$/L and had at least doubling of baseline platelet count could enter an extended FU period for up to 13 weeks, and patients who relapsed (defined as platelet count below 30×10$^9$/L) could be retreated in a 1-year open-label extension (OLE) period.

The study included patients aged 18 to 85 years, with confirmed primary ITP and average platelet count <30× 10$^9$/L during screening (average of 2 counts, with no single reading >35×10$^9$/L). Oral corticosteroids, oral immunosuppressants, and/or TPO-RA were permitted during the study and had to be stable in dose and frequency for at least 4 weeks prior to screening and during the study. Additionally, patients with total IgG level <6 g/L at screening were excluded. Patients were described as newly diagnosed (within 3 months of diagnosis), persistent (between 3-12 months from diagnosis), and chronic (lasting for more than 12 months).

Treatment Interventions

Patients were randomized 1:1:1 to receive 4 weekly intravenous infusions (at days 1, 8, 15, and 22) of either placebo or efgartigimod at a dose of 5 mg/kg or 10 mg/kg body weight. Patients who entered the OLE period received cycle(s) of 4 weekly infusions of efgartigimod 10 mg/kg. Rescue therapy (defined as start of a new ITP therapy or increase in dose or dosing frequency of concomitant ITP therapy) was permitted during the study at the discretion of the investigator when deemed medically necessary. Patients receiving rescue therapy were discontinued from the investigational medicinal product and followed until the end of the study for safety.

Patient Disposition, Demographics, and Baseline Characteristics

Sixty-two patients were screened, of which 38 patients were randomized 1:1:1 to receive a total of 4 weekly intravenous infusions of either placebo (N=12) or efgartigimod at a dose of 5 (N=13) or 10 mg/kg (N=13). Overall, 35 (92.1%) patients completed the treatment period and 32 (84.2%) completed 8 weeks FU. Fourteen (36.8%) patients entered extended FU (6 patients in efgartigimod 5 mg/kg, 6 in efgartigimod 10 mg/kg, and 2 in placebo group). Finally, 12 (31.6%) patients entered the OLE period and received 1 or more cycles of 4 weekly infusions of efgartigimod 10 mg/kg. Among these 12 patients, 2 (15.4%) patients had received efgartigimod 5 mg/kg in the randomized period, 6 (46.2%) efgartigimod 10 mg/kg, and 4 (33.3%) placebo.

Study demographics and baseline characteristics were generally comparable across the study groups (Table 1). Twenty-eight (73.7%) patients were classified as chronic ITP and 2 (5.3%) patients as newly diagnosed ITP (≤3 months duration). Median duration of ITP was 4.8 years (range 0.1-47.8). Twenty (52.6%) patients had baseline platelet count <15×10'L. Median number of prior ITP treatments was 2.0 (1-10). Nine patients (23.7%) had previously received rituximab, 14 (36.8%) a TPO-RA of whom 10 (26.3%) were receiving a TPO-RA treatment at baseline, and 6 (15.8%) had prior splenectomy. Twenty-seven (71.1%) patients were receiving at least 1 concomitant ITP therapy at baseline.

evaluation of the pharmacodynamic (PD) markers (total IgG, subtypes IgG1, IgG2, IgG3, and IgG4) and pharmacokinetics (PK), and the presence of anti-drug antibodies (ADA). Measurements of platelet-bound IgG anti-platelet activity were performed according to manufacturer's instructions at Sanquin Diagnostic Laboratory using a commercially available solid-phase ELISA (PakAuto®Assay, Immucor GTI Diagnostic, Inc, USA).

Efficacy assessments were also assessed as secondary endpoints, and included frequency and proportion of patients with platelet count increase to ≥50×$10^9$/L and ≥100×$10^9$/L at any time, mean platelet count change, the International Working Group definition of "response" (platelet count ≥30 and <100×$10^9$/L, and a greater than 2-fold increase from baseline, confirmed on at least 2 separate consecutive occasions ≥7 days apart, and the absence of bleeding), and "complete response" (platelet count ≥100× $10^9$/L, confirmed on at least 2 separate consecutive occa-

TABLE 1

Summary of demographics and baseline characteristics (full analysis set).

| | Placebo (N = 12) | Efgartigimod: 5 mg/kg (N = 13) | Efgartigimod: 10 mg/kg (N = 13) | Total (N = 38) |
|---|---|---|---|---|
| Age (years), median (range) | 38.5 (19-69) | 41.0 (22-77) | 46.0 (29-62) | 44.4 (19-77) |
| Gender, n (%) | | | | |
| Male | 5 (41.7) | 4 (30.8) | 9 (69.2) | 18 (47.4) |
| Female | 7 (58.3) | 9 (69.2) | 4 (30.8) | 20 (52.6) |
| ITP Classification, n (%) | | | | |
| Newly diagnosed (≤3 months) | — | 2 (15.4) | — | 2 (5.3) |
| Persistent (>3 and ≤12 months) | 3 (25.0) | 1 (7.7) | 4 (30.8) | 8 (21.1) |
| Chronic (>12 months) | 9 (75.0) | 10 (76.9) | 9 (69.2) | 28 (73.7) |
| Duration of ITP (years), median years (range) | 3.51 (0.3-47.8) | 4.46 (0.1-34.2) | 5.42 (0.7-28.7) | 4.82 (0.1-47.8) |
| Baseline platelet count (×$10^9$/L), mean (range) | 18 (4-40) | 18 (6-49) | 15 (5-35) | 17 (4-49) |
| Baseline platelet count <15 × $10^9$/L, n (%) | 6 (50.0) | 7 (53.8) | 7 (53.8) | 20 (52.6) |
| Number of prior treatments for ITP, median (range) | 2.0 (1-7) | 2.0 (1-8) | 1.0 (1-10) | 2.0 (1-10) |
| Number of patients with prior ITP therapy, n (%) | 12 (100.0) | 13 (100.0) | 12 (92.3) | 37 (97.4) |
| Prior ITP therapy: | | | | |
| Corticosteroids n (%) | 9 (75.0) | 11 (84.6) | 12 (92.3) | 32 (84.2) |
| IVIg or anti-D Ig, n (%) | 5 (41.7) | 4 (30.8) | 2 (15.4) | 11 (28.9) |
| TPO-RA, n (%) | 4 (33.3) | 6 (46.2) | 4 (30.8) | 14 (36.8) |
| Rituximab, n (%) | 3 (25.0) | 4 (30.8) | 2 (15.4) | 9 (23.7) |
| Immunosuppressants, n (%) | 5 (41.7) | 3 (23.1) | 1 (7.7) | 9 (23.7) |
| Danazol, n (%) | 1 (8.3) | 1 (7.7) | — | 2 (5.3) |
| Splenectomy, n (%) | 1 (8.3) | 2 (15.4) | 3 (23.1) | 6 (15.8) |
| Other, n (%) | 3 (25.0) | 2 (15.4) | — | 5 (13.2) |
| Number of patients with concomitant ITP therapy, n (%) | 8 (66.7) | 12 (92.3) | 10 (76.9) | 30 (78.9) |
| Concomitant ITP therapy: | | | | |
| Corticosteroids, n (%) | 3 (25.0) | 10 (76.9) | 6 (46.2) | 19 (50.0) |
| TPO-RA, n (%) | 3 (25.0) | 4 (30.8) | 3 (23.1) | 10 (26.3) |
| Immunosuppressants, n (%) | 1 (8.3) | — | 1 (7.7) | 2 (5.3) |
| Other, n (%) | 1 (8.3) | 1 (7.7) | — | 2 (5.3) |

Ig: immunoglobulin.
ITP: primary immune thrombocytopenia,
IV: intravenous,
N: number of patients in the analysis set,
n: observed number of patients within each treatment group,
TPO-RA: thrombopoietin receptor agonist.
Note:
percentages are based on N.

Primary endpoints were changes in vital signs, electrocardiogram parameters, and clinical laboratory assessments and the incidence and severity of treatment-emergent adverse events (TEAE). Secondary endpoints included the sions ≥7 days apart, and the absence of bleeding), and bleeding assessment using the World Health Organization (WHO) bleeding scale and ITP-specific bleeding assessment tool (ITP-BAT). Post hoc analyses included percentage of patients with a platelet count ≥50×10⁹/L on at least 2 occasions, and in patients achieving this threshold the duration of platelet count ≥50×10⁹/L. Additionally, the proportion of patients with platelet count ≥50×10⁹/L for at least 10 cumulative days was calculated. A schedule of assessments is shown in Table 2.

TABLE 2

Schedule of assessments: Main study including extended follow-up period.

| Assessments | Screening[a] | Visits | | | | | | | | | |
|---|---|---|---|---|---|---|---|---|---|---|---|
| | Screening | Treatment Period | | | | | | | Follow-Up Period | | |
| Visits | Visit | V1 | V2 | V3 | V4 | V5 | V6 | V7 | V8 | V9 | V10 |
| Study Day* | | 1 | 4 ± 1 | 8 ± 1 | 11 ± 1 | 15 ± 1 | 18 ± 1 | 22 ± 1 EoT | 25 ± 1 | 29 ± 1 | 36 ± 1 |

| | | | | | | | | | Weeks post last infusion | |
|---|---|---|---|---|---|---|---|---|---|---|---|
| | | | | | | | | | | 1 | 2 |
| Informed consent[b] | X[y] | | | | | | | | | | |
| Inclusion/exclusion criteria | X | X[b] | | | | | | | | | |
| Medical/surgical history | X | | | | | | | | | | |
| Demographic data | X | | | | | | | | | | |
| Vital signs | X | X | | X | | X | | X | | X | X |
| Physical examination including height, weight[c] | X | X | | X | | X | | X | | X | X |
| General Bleeding Assessment (WHO and SMOG) | X | X | | X | | X | | X | | X | X |
| SF-36 and FACT-Th6[d] | X | X | | | | | | | | X | |
| Hematology and chemistry tests[e, t, u] | X | X | | X | | X | | X | | X | X |
| Platelet counts | X[g] | X[r] | X | X[r] | X | X[r] | X | X[r] | X | X[r] | X[r] |
| Coagulation, thyroid, and autoimmune antibody testing[h,u,v] | X | | | | | | | | | | |
| Follicle-stimulating hormone[i, u] | X | | | | | | | | | | |
| ECG | X | X | | | | | | X[s] | | X | |
| Urinalysis[u] | X | X | | X | | X | | X | | X | X |
| Pharmacokinetics | | X[q] | X | X[q] | X | X[q] | X | X[q] | X | X | X |
| Pharmacodynamics[j] | | X | X | X | X | X | X | X | X | X | X |
| Antiplatelet antibodies and IgG and its subtypes | | X | | X | | X | | X | | X | X |
| Antidrug antibodies | | X | | X | | X | | X | | X | X |
| Pregnancy test[k] | X | X | | | | | | | | X | |
| Viral tests and TB serology[l] | X | | | | | | | | | | |
| Randomization[m] | | X | | | | | | | | | |
| Pharmacogenetics[n] | | X | | | | | | | | | |
| Administration of IMP[f] | | X[o] | | X[o] | | X[o] | | X[o] | | | |
| Concomitant therapies/procedures[p] | | | | | | | | | | | |
| Aes[p] | | | | | | | | | | | |

| | | Visits | | | | | | |
|---|---|---|---|---|---|---|---|---|
| Assessments | | Follow-Up Period | | | | | | Extended |
| Visits | | V11 | V12 | V13 | V14 | V15 | V16 | FU Period |
| Study Day* | | 43 ± 1 | 50 ± 1 | 57 ± 1 | 64 ± 1 | 71 ± 1 | 78 ± 3 (EoS)/ED | Safety visit 78 ± 3 up to 169 ± 7 EoFU[z] |

TABLE 2-continued

Schedule of assessments: Main study including extended follow-up period.

| | Weeks post last infusion | | | | | | | |
|---|---|---|---|---|---|---|---|---|
| | 3 | 4 | 5 | 6 | 7 | 8 | | |
| Informed consent[b] | | | | | | | | |
| Inclusion/exclusion critetia | | | | | | | | |
| Medical/surgical history | | | | | | | | |
| Demographic data | | | | | | | | |
| Vital signs | X | X | X | X | X | X | X | |
| Physical examination including height, weight[c] | X | X | X | X | X | X | X | |
| General Bleeding Assessment (WHO and SMOG) | X | X | X | X | X | X | | X[x] |
| SF-36 and FACT-Th6[d] | | X | | | X | | | |
| Hematology and chemistry tests[e, f, u] | X | X | X | X | X | X | X | |
| Platelet counts | X[r] | X[r] | X[r] | X[r] | X[r] | X[r] | | X[w] |
| Coagulation, thyroid, and autoimmune antibody testing[h,u,v] | | | | | | | | |
| Follicle-stimulating hormone[i, u] | | | | | | | | |
| ECG | | | | | | X | X | |
| Urinalysis[u] | X | X | X | X | X | X | X | |
| Pharmacokinetics | X | X | | | | | | |
| Pharmacodynamics[j] | X | X | X | X | X | X | | |
| Antiplateleti antibodies and IgG and its subtypes | | | | | | | | |
| Antidrug antibodies | X | X | X | X | X | X | | |
| Pregnancy test[k] | | | X | | | X | X | |
| Viral tests and TB serology[l] | | | | | | | | |
| Randomization[m] | | | | | | | | |
| Pharmacogenetics[n] | | | | | | | | |
| Administration of IMP[f] | | | | | | | | |
| Concomitant therapies/procedures[p] | | | | | | | | |
| Aes[p] | | | | | | | | |

Abbreviations:
AEs = adverse events;
DNA = Deoxyribonucleic acid;
ECG = electrocardiogram;
ED = early discontinuation;
EoFU = end of follow-up;
EoS = end of study;
EoT = end of treatment;
FACT-Th6 = Functional Assessment of Cancer Therapy Questionnaire-Th6;
HBcAb = hepatitis B core antibody;
HBsAg = hepatitis B surface antigen;
HIV = human immunodeficiency virus;
ICF = informed consent form;
IgG = immunoglobulin G;
IMP = investigational medicinal product;
SMOG/ITP-BAT = immune thrombocytopenia-bleeding assessment tool;
SAE = serious adverse event;
SF-36 = Short Form-36;
TB = tuberculosis;
US = unscheduled visit;
WHO = World Health Organization.

*The allowed window period between visits in Treatment period and Follow-up period is ±1 day provided that 2 consecutive visits are 3 days apart at a minimum. Every effort should be made to schedule every visit on the exact Day (which is relative to the Baseline visit or [Visit 1]) as described in above Schedule of Assessments without the window.
[a]Took place between 1 and 14 days prior to first administration of IMP at Visit 1.
[b]No study-related assessment was carried out before signing of the informed consent form. The assessment of inclusion and exclusion criteria for further confirmation of eligibility was performed at Visit 1 prior to start of other study specific procedures/randomization.
[c]Height was measured at Screening (and Body Mass Index calculated accordingly). Weight was recorded at Screening and before each administration of IMP (as IMP depends on patient weight).
[d]Patient reported outcome assessments were mandatory to be performed before any other assessments at the visit.

TABLE 2-continued

Schedule of assessments: Main study including extended follow-up period.

$^e$Hematology and blood chemistry included all of clinical chemistry (sodium, potassium, chloride, glucose, bicarbonate, creatinine, blood urea nitrogen, alanine transaminase, AST, total bilirubin, gamma-GT, CRP, AP, lactate dehydrogenase, uric acid, total protein, and albumin), hematology (hemoglobin, hematocrit, mean corpuscular volume, mean corpuscular hemoglobin, mean corpuscular hemoglobin concentration, red blood cell count, platelet count, white blood cell count with differential), and urinalysis (abnormal blood on dipstick). Patients were fasting for at least 8 hours prior to blood glucose assessment at Screening. At all other visits (including Visit 1 pre-dose sampling), patient need not be fasting since blood glucose testing was done by the measurement of HbA1c.
$^f$Assessments were completed pre-dose on all study drug infusion days.
$^g$To determine eligibility of patients, platelet counts were be performed at 2 separate visits, during Screening, at least 1 day apart. The first count was made by the central laboratory based on the sample taken at Screening. The second count could be based on local laboratory result and was no more than 3 days prior to commencing study treatment. Samples for central laboratory were collected at this visit.
$^h$Antinuclear antibody, prothrombin time, international normalized ratio, activated partial thromboplastin time, thyroglobulin, thyroid stimulating hormone.
$^i$Evaluated to confirm post-menopausal status in women who have been amenorrheic for 12 months or more and who were not on hormonal replacement therapy.
$^j$Total IgG, IgG subtypes (IgG1, IgG2, IgG3, and IgG4), antiplatelet antibodies. Pharmacodynamic samples were collected pre-dose on all dosing days. In addition, IgA, IgD, IgE, and IgM were assessed. Antiplatelet antibodies were measured with two different assays (PakAuto assay (Visit 1 pre-dose, Visit 8 [or Visit 9] and Visit 16) and non-validated assay [Visit 1 to Visit 16]).
$^k$Serum pregnancy test was performed at Screening and a urine pregnancy test at randomization and all other relevant visits.
$^l$Includes HBsAg, HBcAb, anti-HBs and anti-HCV, HIV 1 and 2 antibodies and TB serology (QuantiFERON ®-TB Gold).
$^m$Randomization was completed before administration of IMP.
$^n$A blood sample (for future association studies of FcRn genotype with the PK and safety characteristics obtained) was collected at any point prior to first dosing (Visit 1) after a separate pharmacogenetic ICF had been signed. In case the blood draw at Baseline was missed, the sample was taken prior to dosing at the next visit during the study.
$^o$Investigational medicinal product or placebo was administered as an IV infusion over a period of 2 hours at Visits 1, 3, 5, and 7. Patient was monitored in-house for at least 2 hours post-infusion.
$^p$Adverse events, intake of concomitant medication(s) and new procedure were monitored continuously from signing the ICF until the last study-related activity. In case of early discontinuation, any AEs/SAEs were assessed for 30 days following the Early Discontinuation visit or until satisfactory resolution or stabilization.
$^q$PK assessments were done both pre- and post-dose (within 30 minutes prior to start of infusion for pre-dose sample and within 30 minutes after end of infusion for post-dose sample) on all IMP infusion days.
$^r$At these visits, platelet counts were obtained as part of the hematology tests. Values from the central and local laboratory were taken as Baseline for all future platelet count measurements.
$^s$At Visit 7 the ECG was taken post-infusion.
$^t$At Screening: Total immunoglobulin G (IgG) level at screening was determined by the local laboratory (excl. crit. 10.g.)
$^u$At Screening: If the investigator determined a screening laboratory abnormality, this result was confirmed by the local laboratory.
$^v$Either TSH or thyroglobulin was measured at Screening. In case the results from the selected test were not available by the time of randomization then the alternative test (TSH or thyroglobulin) was measured.
$^w$Extended FU period: platelet counts from local laboratoty and rescue medication will be collected retrospectively/prospectively from the patient's medical file.
$^x$Only WHO bleeding scale if available in the patient's medical file will be reported.
$^y$The amended ICF of the main study must be signed by all patients.
$^z$End of follow-up visit for the extended FU period was considered the visit at which relapse was observed and rescue treatment given or, in case no relapse occurred, the nearest visit before the end of the 13-week extended FU period.

Clinical Pharmacology

Figure 3:
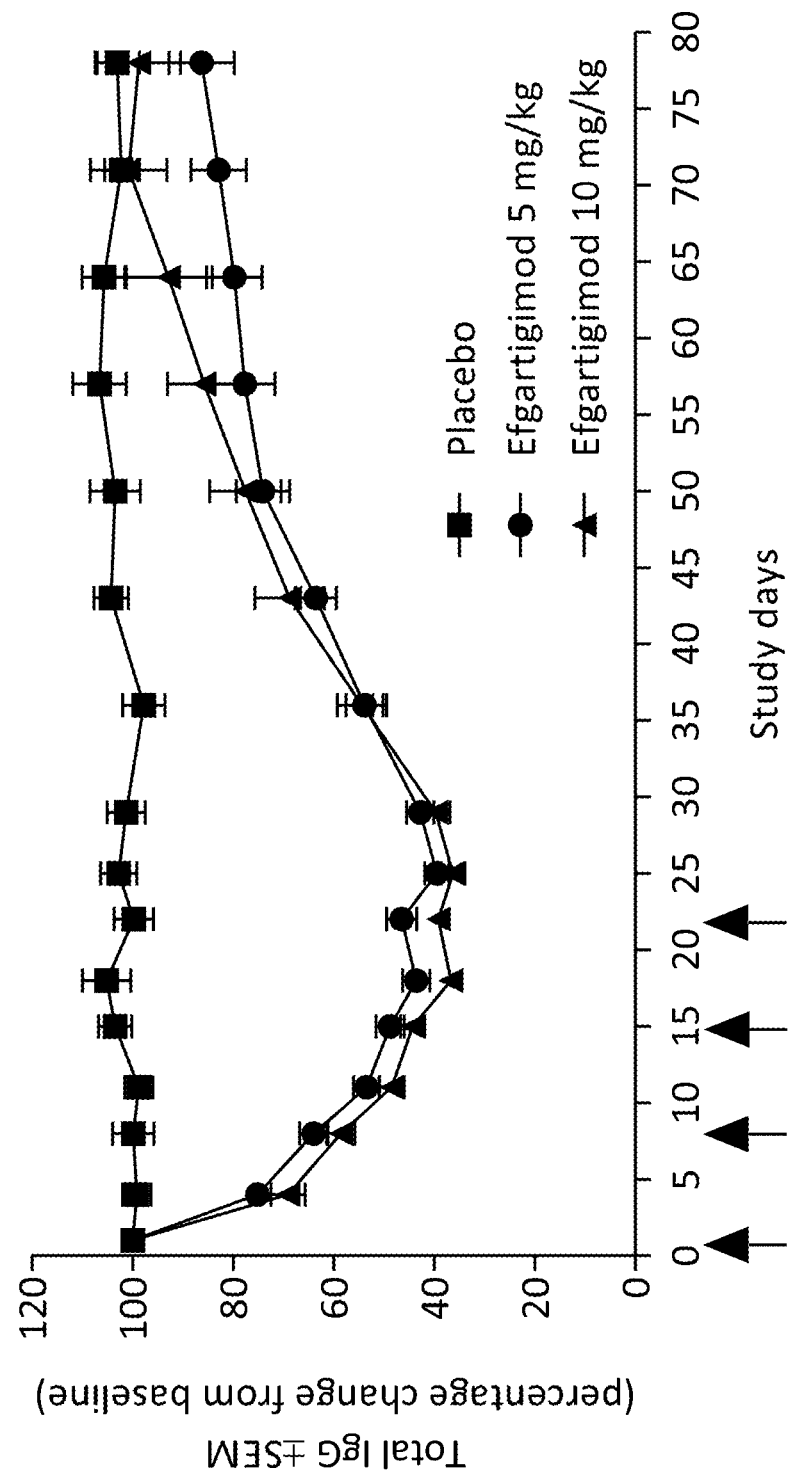
FIG. 3 is a graph depicting percentage reduction of total IgG assessed during the main study described in Example 5.
Figure 4A:
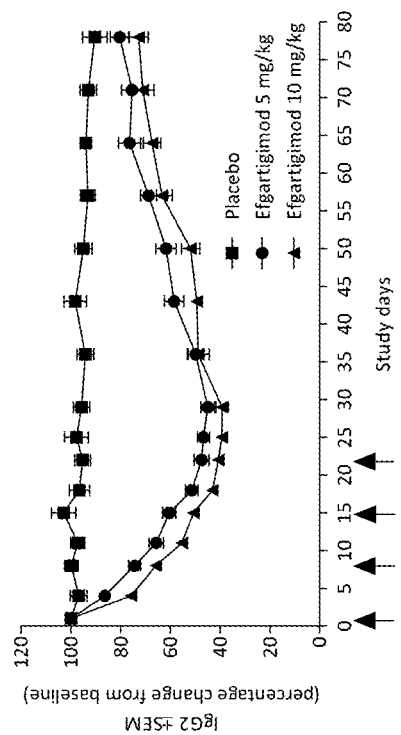
FIGS. 4A-4D are graphs depicting percentage reduction of each IgG subtype assessed during the main study described in Example 5.
Figure 4B:
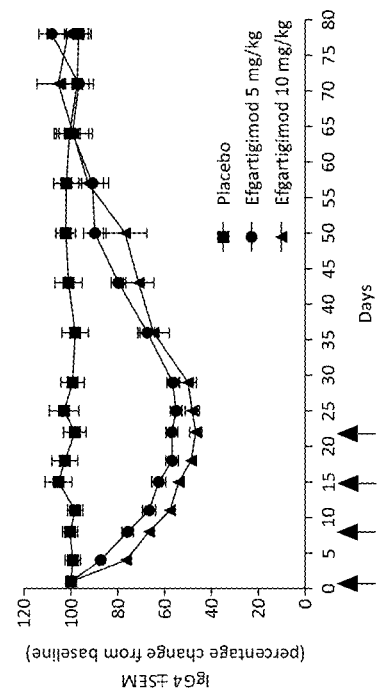
Figure 4C:
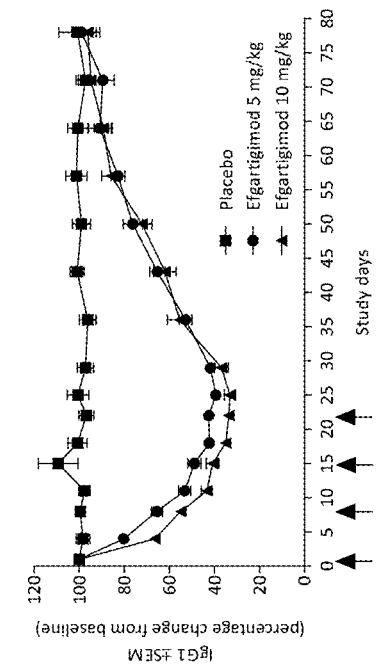
Figure 4D:
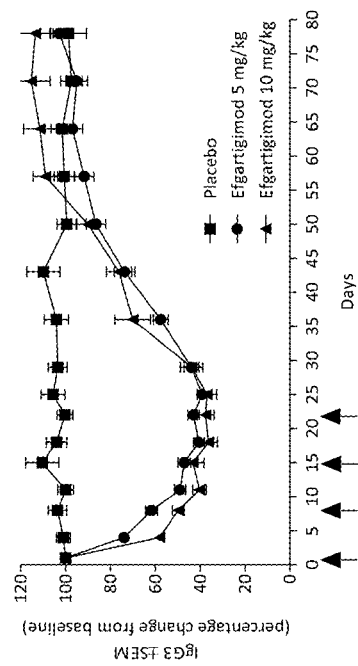

Efgartigimod 5 and 10 mg/kg induced a rapid reduction of total IgG (FIG. 3), up to a maximum mean change of 60.4% on efgartigimod 5 mg/kg (from 9.9 g/L [SD=3.2] at baseline to 4.0 g/L [SD=0.8]) and 63.7% on 10 mg/kg (from 10.6 g/L [SD=5.1] at baseline to 4.1 g-L [SD=2.0]) at day 25, compared with no distinguishable change from baseline in the placebo group. IgG reduction was observed in all IgG subtypes (FIG. 4).

Mean percent changes from baseline in IgA, IgD, IgE, IgM were similar between placebo and the efgartigimod treated groups, mostly within ±10-15% of baseline (data not shown) and changes were not considered clinically relevant. Positive pre-dose ADA were detectable in 1 (7.7%) patient treated with efgartigimod 5 mg/kg, 3 (23.1%) efgartigimod 10 mg/kg, and 2 (16.7%) placebo. Positive post-dose ADA titers were detected in 5 (38.5%) patients treated with efgartigimod 5 mg/kg, 4 (30.8%) efgartigimod 10 mg/kg, and 2 (16.7%) placebo. ADA titers were typically low and did not have an apparent effect on PK/PD. Analysis of the antiplatelet antibody eluates revealed the presence of platelet-associated autoantibodies (GPIIb/IIIa, GPIb/IX, GPIa/IIa) in all randomized patients. In 8/12 (66.7%) patients treated with 5 mg/kg efgartigimod and 7/10 (70.0%) patients in 10 mg/kg group a reduction greater than 40% in the platelet-associated autoantibody signal for at least 1 type of autoantibody was observed upon treatment at days 25/29 and/or 78. One patient (7.7%) in the 5 mg/kg group and 3 (23.1%) patients in the 10 mg/kg group were not evaluable either due to a missing baseline sample or because all post-dose samples were obtained after rescue therapy. Presence of autoantibodies in serum was less prevalent.

Efficacy

Figure 5:
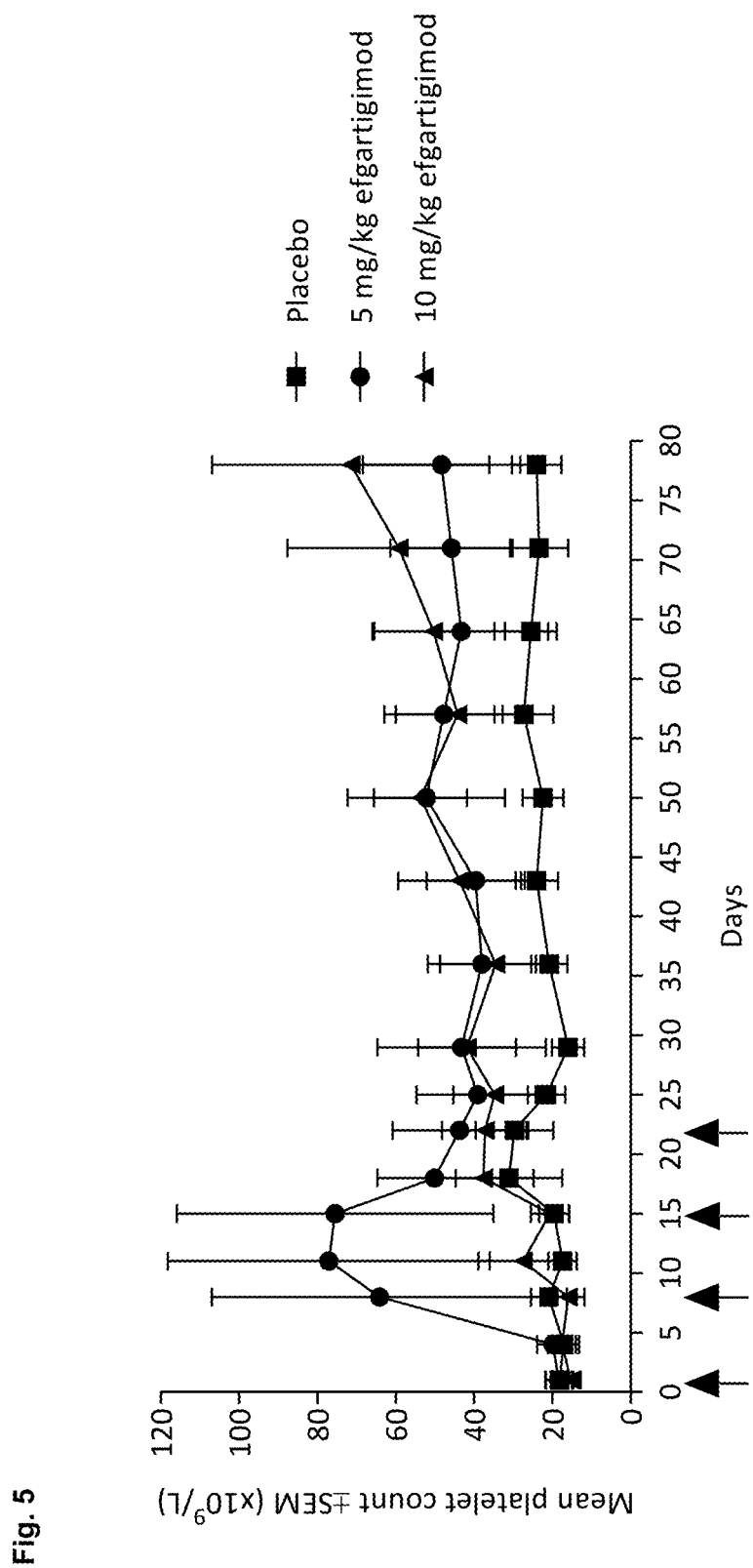
FIG. 5 is a graph depicting mean platelet count and standard error of the mean per patient group during the main study described in Example 5. Arrows indicate the timing of efgartigimod administration.
Figure 6:
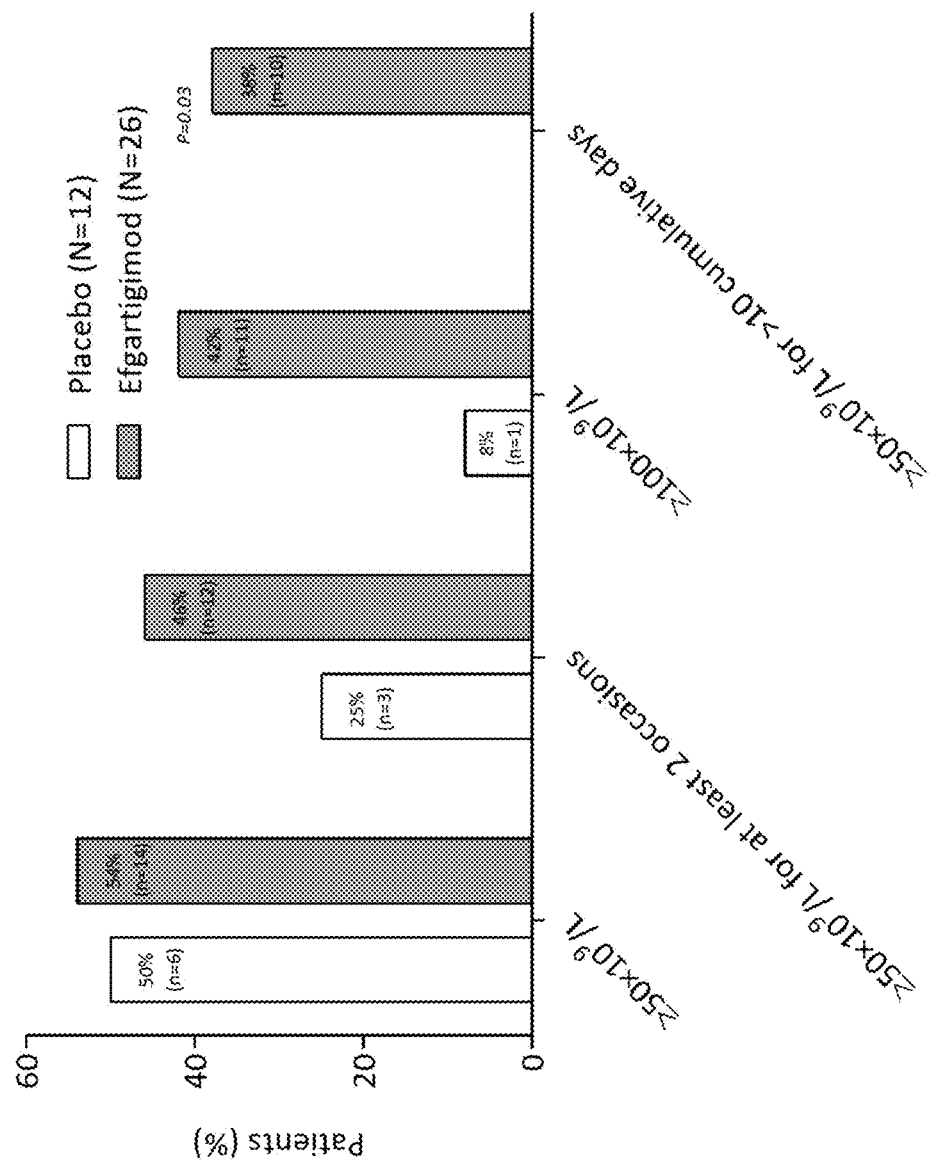
FIG. 6 depicts proportion of patients achieving increasing thresholds of platelet count increase assessed in the main study described in Example 5.

Both efgartigimod-treated groups achieved a higher maximum mean platelet count change from baseline compared to the placebo group ($77.2 \times 10^9$/L at day 11 in the 5 mg/kg group, $71.5 \times 10^9$/L at day 78 in the 10 mg/kg group, $31.1 \times 10^9$/L at day 18 in placebo) (FIG. 5). Platelet count of $>50 \times 10^9$/L at any time was achieved by 7 (53.8%) patients in both efgartigimod-treated group, and 6 (50.0%) in placebo group (FIG. 6). A platelet count $\geq 100 \times 10^9$/L at any time was achieved by 6 (46.2%) patients in efgartigimod 5 mg/kg group, 5 (38.5%) in efgartigimod 10 mg/kg treatment group, and 1 (8.3%) in placebo group. The International Working Group definition of "response" or "complete response" was achieved by 5 (38.5%) patients in efgartigimod 5 mg/kg group, 4 (30.8%) in efgartigimod 10 mg/kg treatment group, and 2 (16.7%) in placebo group. Otherwise, 2 newly diagnosed ITP patients and 1 chronic ITP patient maintained an increased platelet count throughout the extended FU period (up to day 162).

Post hoc analyses were performed (FIG. 6). Platelet count $\geq 50 \times 10^9$/L on at least 2 occasions was achieved by 6 (46.2%) patients in both efgartigimod-treated group, and 3 (25.0%) in the placebo group. For these patients, the mean cumulative duration of platelet count $\geq 50 \times 10^9$/L was 24.5 days (SD=20.70) ranging between 3 and 73 days for efgartigimod-treated patients, and 7.3 days (SD=2.89) ranging between 4 and 9 days for placebo-treated patients. Additionally, 10 (38.5%) efgartigimod-treated patients and 0 (0.0%) placebo-treated patients achieved a platelet count $\geq 50 \times 10^9$/L for a cumulative duration of more than 10 days. The first time of achieving a platelet count $\geq 50 \times 10^9$/L (for patients achieving a platelet count $\geq 50 \times 10^9$/L on at least 2 occasions) ranged from 8 to 43 days for the efgartigimod-treated patients.

Four (30.8%) patients in the efgartigimod 5 mg/kg treatment group received rescue treatment during the randomized period, 3 had not achieved platelet count $\geq 50 \times 10^9$/L. Three (23.1%) patients received rescue therapy in the efgartigimod 10 mg/kg treatment group during the randomized period, 2 (15.4%) of whom had only received 3 doses. None of the patients had achieved a platelet count ≥50×10⁹/L. One placebo patient received rescue therapy at day 53.

Figure 10:
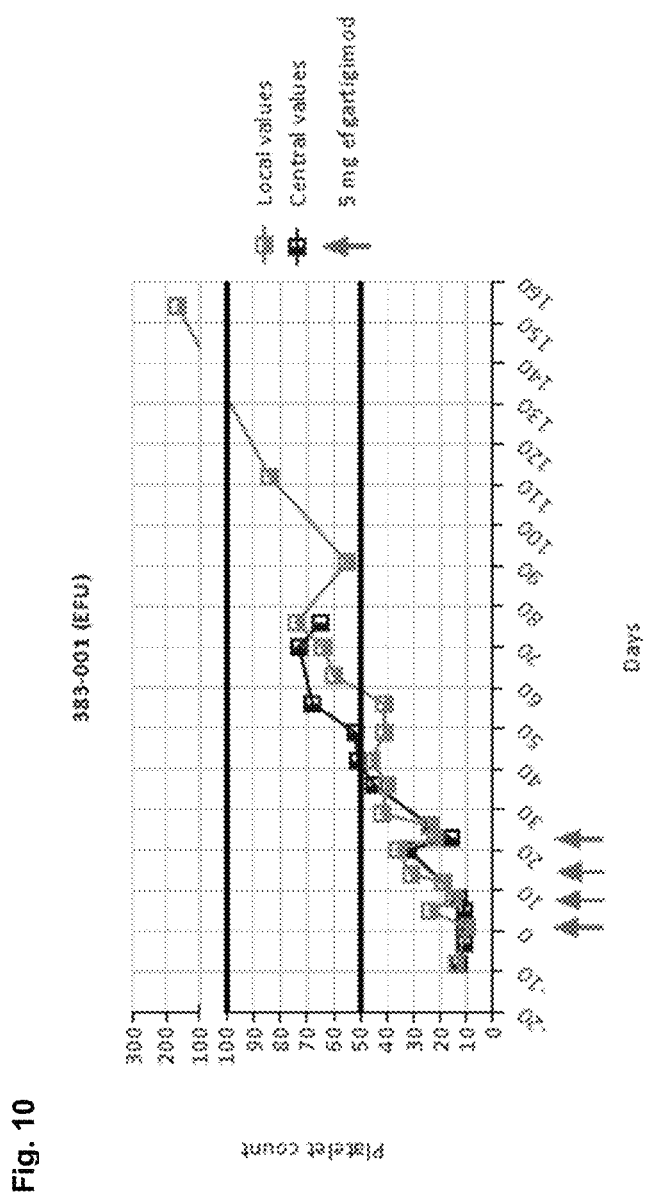
FIG. 10 depicts platelet count response in a patient with newly diagnosed ITP treated with 5 mg/kg efgartigimod as described in Example 5. Platelet count shown is expressed in terms of $\times 10^9$/L.

Of the 12 patients who entered the OLE period and received 4 weekly infusions of 10 mg/kg, 3 (25.0%) patients had achieved platelet counts ≥50×10⁹/L on at least 2 occasions during the randomized period, all treated with efgartigimod 10 mg/kg (Table 3). Eight out of 12 (66.7%) patients achieved platelet counts ≥50×10⁹/L on at least 2 occasions in the first cycle of the OLE period. Amongst these 8 patients, 2 from efgartigimod 5 mg/kg and 3 from placebo had not achieved this threshold in the randomized period, and 3 patients re-treated with efgartigimod 10 mg/kg who reached this threshold in the randomized period, achieved this in both the randomized and OLE periods.

fourth dose of efgartigimod 5 mg/kg. Patient 383-001 (FIG. 10) was a 50-year-old female diagnosed with ITP about 2 1/2 months prior to screening for the study, maintained on SoC treatment consisting of prednisone 10 mg p.o. daily since about two months after her diagnosis. As shown in FIG. 10, she had a baseline platelet count of about 15×10⁹/L and achieved a sustained platelet count of >50×10⁹/L beginning about three weeks after she received the fourth dose of efgartigimod 5 mg/kg.

Figure 9:
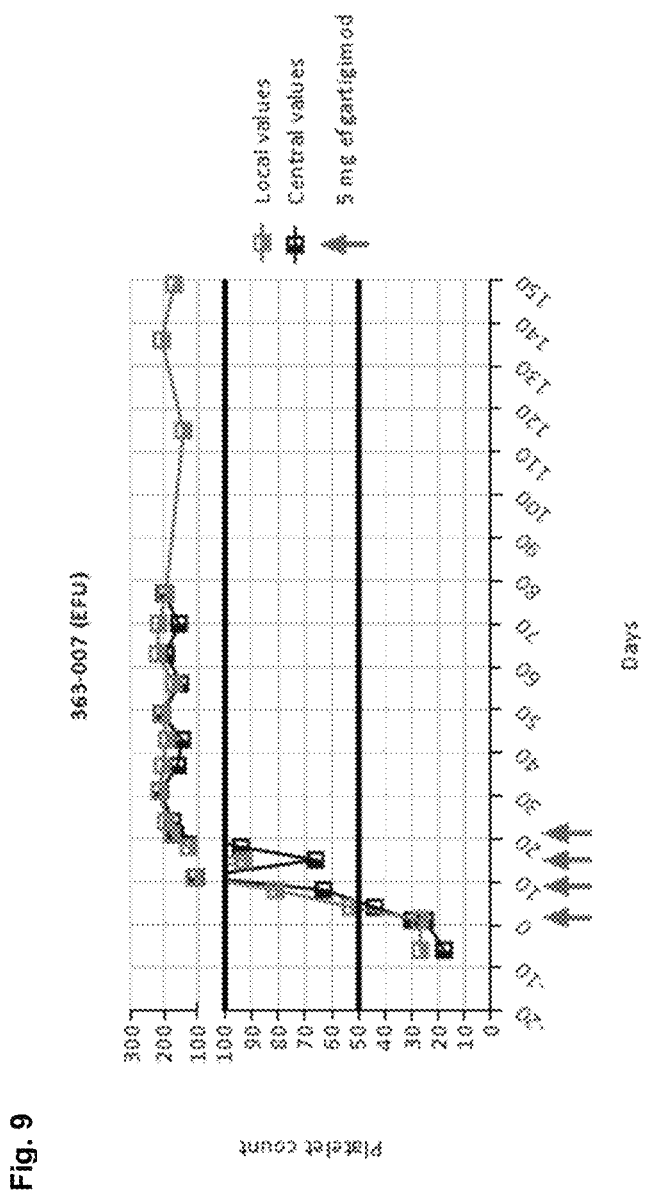
FIG. 9 depicts platelet count response in a patient with newly diagnosed ITP treated with 5 mg/kg efgartigimod as described in Example 5. Platelet count shown is expressed in terms of $\times 10^9$/L.
Figure 11:
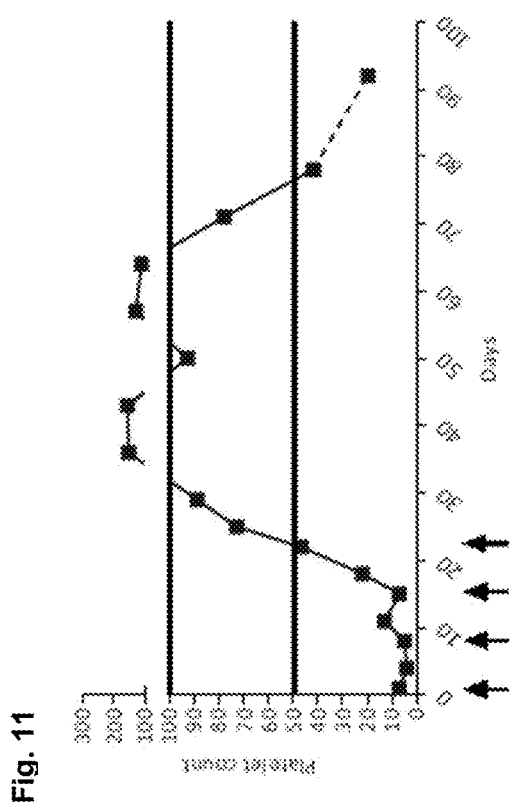
FIG. 11 depicts platelet count response in a patient with persistent ITP who was receiving no treatment (i.e., was on approved wait-and-see approach for treatment with at least one compound approved for treatment of ITP) prior to entry into the Phase 2 study and was treated with 10 mg/kg efgartigimod as described in Example 5. Platelet count shown is expressed in terms of $\times 10^9$/L.

FIG. 11 shows results in a patient with persistent ITP treated with 10 mg/kg efgartigimod. This patient (331-003) was on "wait-and-see" treatment (observation without active intervention) prior to entry into the study. As shown in FIG. 9, this patient had a baseline platelet count <10×10⁹/L and

TABLE 3

Patients achieving different platelet thresholds in the first cycle of the open label extension period (N = 12).

| | Main study (screening, treatment, and follow-up periods) | | | | Open-label extension period | | | |
|---|---|---|---|---|---|---|---|---|
| Patient | Dose | ≥ 50 × 10⁹/L | ≥ 50 × 10⁹/L for at least 2 occasions | ≥ 50 × 10⁹/L for at least 10 cumulative days | Dose | ≥ 50 × 10⁹/L | ≥ 50 × 10⁹/L for at least 2 occasions | ≥ 50 × 10⁹/L for at least 10 cumulative days |
| 1 | Placebo | | | | 10 mg/kg | X | X | X |
| 2 | | | | | | | | |
| 3 | | X | | | | X | X | X |
| 4 | | | | | | X | X | |
| 5 | 5 mg/kg | | | | | X | X | |
| 6 | | | | | | X | X | X |
| 7 | 10 mg/kg | X | X | X | | X | X | X |
| 8 | | X | | | | | | |
| 9 | | X | X | | | X | X | X |
| 10 | | | | | | | | |
| 11 | | | | | | | | |
| 12 | | X | X | | | X | X | X |
| Total | n (%) | 5 (41.7) | 3 (25.0) | 1 (8.3) | n (%) | 8 (66.7) | 8 (66.7) | 6 (50.0) |

N: number of patients in the analysis set,
n: observed number of patients within each treatment group.
Note:
percentages are based on N.

Figure 7:
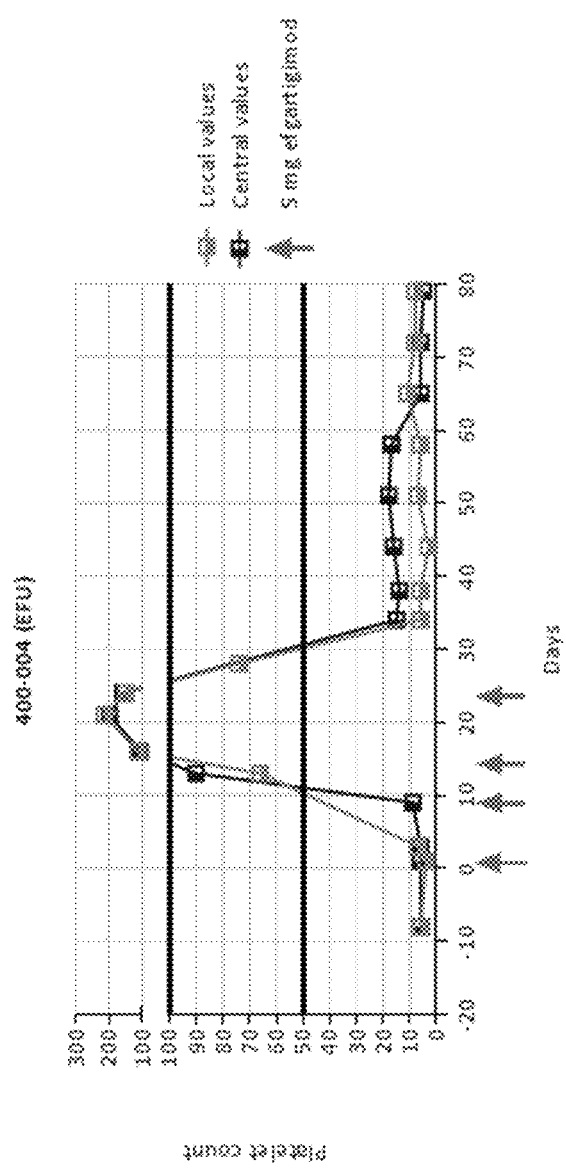
FIG. 7 depicts platelet count response in a patient with chronic ITP treated with 5 mg/kg efgartigimod as described in Example 5. Platelet count shown is expressed in terms of $\times 10^9$/L.
Figure 8:
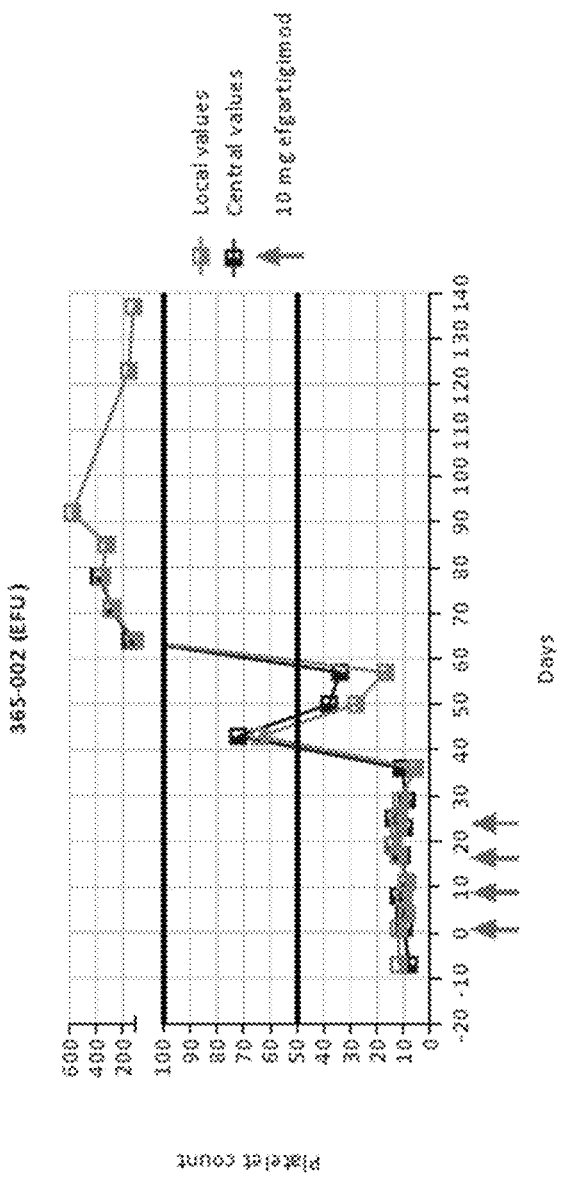
FIG. 8 depicts platelet count response in a patient with chronic ITP treated with 10 mg/kg efgartigimod as described in Example 5. Platelet count shown is expressed in terms of $\times 10^9$/L.

FIG. 7 and FIG. 8 show results in two patients with chronic ITP treated with 5 mg/kg or 10 mg/kg efgartigimod, respectively. Patient 400-004 (FIG. 7) was a 41-year-old female with ITP originally diagnosed in 1984, maintained on SoC treatment consisting of eltrombopag 75 mg p.o. daily since 2014. As shown in FIG. 7, she had a baseline platelet count <10×10⁹/L, and she achieved a platelet count of ~200×10⁹/L by the time she received the fourth dose of efgartigimod 5 mg/kg. Patient 365-002 (FIG. 8) was a 57-year-old male with ITP originally diagnosed in 2005, maintained on SoC treatment consisting of methylprednisolone 100 mg p.o. daily since 2017. As shown in FIG. 8, he had a baseline platelet count of about 10×10⁹/L, and he achieved a sustained response of >100×10⁹/L beginning about 60 days after receiving his first dose of efgartigimod 10 mg/kg.

FIG. 9 and FIG. 10 show results in two patients with newly diagnosed ITP treated with 5 mg/kg efgartigimod. Patient 363-007 (FIG. 9) was a 32-year-old female diagnosed with ITP about one month prior to screening for the study, maintained on SoC treatment consisting of solumedrol 12 mg p.o. daily since shortly after her diagnosis. As shown in FIG. 9, she had a baseline platelet count ~20×10⁹/L, and she achieved a sustained increased platelet count of ~200×10⁹/L beginning around the time she received the achieved an increased platelet count of >about 100×10⁹/L for about 6 weeks beginning around a week after receiving the fourth dose of efgartigimod 10 mg/kg.

Bleeding-Related Events

Figure 12:
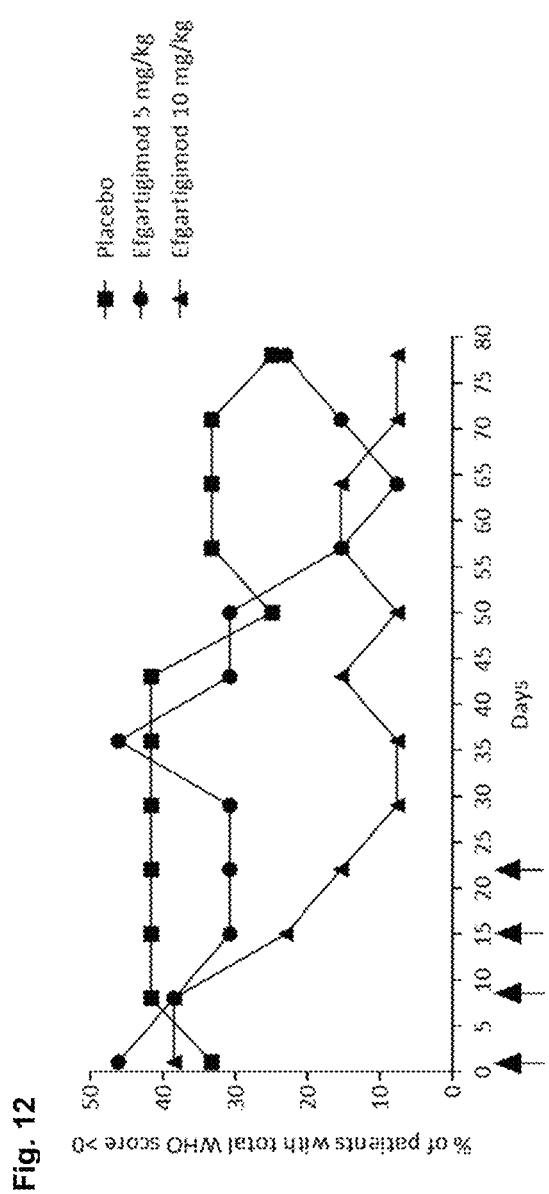
FIG. 12 is a graph depicting percent of patients with bleeding events assessed using the World Health Organization (WHO) scale.
Figure 13:
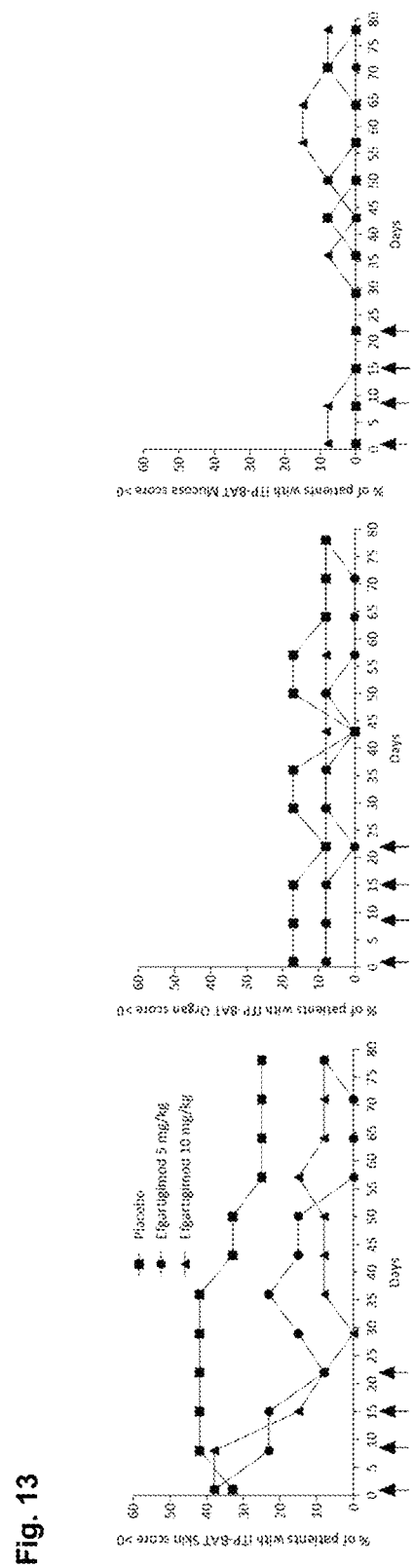
FIG. 13 is a series of three graphs depicting percent of patients with bleeding events assessed using the ITP-specific bleeding assessment tool (ITP-BAT) scale. Left to right: skin score>0, organ score>0, and mucosa score>0.

At least 1 bleeding TEAE was reported in 5 (38.5%) patients in each treatment group, and 3 (25.0%) in placebo group. No bleeding TEAEs were deemed study drug-related and no severe bleeding events were reported. The incidence, location and severity of any bleeding symptoms were also recorded using the WHO and ITP-BAT scales (FIGS. 12 and 13, respectively). The proportion of patients with bleeding (total WHO>0) decreased in both efgartigimod 5 and 10 mg/kg groups, from 46.2% to 7.7% at day 64, and from 38.5% to 7.7% at day 29, respectively.

Discussion

This randomized, double-blind, placebo-controlled Phase 2 study assessed the safety and efficacy of efgartigimod in patients with predominantly longstanding ITP (median disease duration of 4.82 [0.1-47.8] years), who had an insufficient response to prior ITP therapy. More than half of the patient population (20 [52.6%]) had a baseline platelet count <15×10⁹/L.

Efgartigimod was well tolerated with no dose-related safety observations. The safety profile was consistent with previous observations in healthy volunteers and myasthenia gravis patients. No increased rate of infection was observed in the efgartigimod-treated groups. One case of pneumonia was reported in the OLE period, occurring 8 weeks after the last dose of efgartigimod, when total IgG levels were approaching baseline and in a patient with a history of splenectomy.

Targeting FcRn with efgartigimod was selective for IgG reduction and did not impact the levels of other immunoglobulin isotypes. Additionally, the total IgG reduction did not reach the very low levels observed to be associated with increased risk of infection in diseases causing hypogammaglobulinemia. Notably, efgartigimod administration did not result in a reduction of albumin levels, which has been observed with some anti-FcRn monoclonal antibodies, suggesting differences in mechanisms between these 2 types of FcRn antagonists.

Treatment with a short cycle of efgartigimod resulted in a rapid and marked reduction of total IgG and all IgG subtypes in all treated patients and a greater numerical reduction was observed in the efgartigimod 10 mg/kg group. Whereas as many as 60% to 70% of patients with ITP have detectable platelet associated autoantibodies, generally directed at the most abundant platelet surface GP, GPIIb/IIIa, GPIb/IX, GPIa/IIa, they were identified in all patients in this study and reduced following efgartigimod treatment.

Mean platelet count increased in both efgartigimod-treated groups. The early and substantial increase in the efgartigimod 5 mg/kg group could be explained by 1 patient, who was receiving eltrombopag as concomitant ITP therapy, and whose platelet count increased to more than $500 \times 10^9$/L from day 8 to 15. It will be interesting to further study whether there is a synergistic effect of IgG-depletion by efgartigimod and other ITP treatments with different mechanism of actions, such as the TPO-RA.

A surprisingly high number of patients receiving placebo achieved a single platelet count $\geq 50 \times 10^9$/L during the study (6 [50%] compared to 14% across two 24-week fostamatinib Phase 3 studies for example). However, post hoc analyses requiring greater frequency or duration of platelet count $\geq 50 \times 10^9$/L, or increased platelet count $\geq 100 \times 10^9$/L, demonstrated the efficacy of efgartigimod. Six patients (46%) treated in both efgartigimod groups showed an increase in platelet count $>50 \times 10^9$/L on at least 2 occasions. Additionally, statistically significantly more active-treated patients achieved a platelet count $\geq 50 \times 10^9$/L for more than 10 cumulative days compared to the placebo group (10 [38%] vs. 0 [0%], respectively).

Autoantibodies in ITP can opsonize platelets resulting in clearance by splenic macrophages, can inhibit megakaryocyte proliferation and differentiation resulting in diminished platelet production, and can induce platelet apoptosis or complement-dependent lysis. Recently, it has also been reported that some anti-GP antibodies can interfere with platelet functionality, either inhibiting platelet aggregation and blood clot formation or inducing desialylation of platelets and Fc-independent liver clearance. More precisely, 3 different patient profiles have been observed in this study. More precisely, a high variability in onset and duration of response was observed following a short exposure of efgartigimod. As shown in FIG. 7, a quick increase in platelet counts was observed in some efgartigimod-treated patients (3 in the efgartigimod 5 mg/kg group and 2 in the 10 mg/kg), which is similar to the time to response reported for an anti-CD16 antibody, IVIg and splenectomy. This suggests that in some patients a limited reduction of autoantibody levels may be sufficient to inhibit the Fc gamma receptor-mediated phagocytosis of antibody-covered platelets as the above-mentioned treatments/procedures are thought to interfere with this pathogenic mechanism. In other patients the time to response was delayed as exemplified in FIG. 11. For those patients, a rise in platelets was observed after the fourth infusion (day 22), which could indicate that a more profound autoantibody reduction is needed and/or that autoantibodies are predominantly affecting the platelet production by the megakaryocytes in the bone marrow, and their removal takes longer to impact the systemic platelet counts. Additionally, few patients demonstrated a double platelet peak following efgartigimod treatment (as illustrated in FIG. 11), suggesting 2 distinct pathogenic autoantibody mechanisms with different kinetics. Interestingly, this phenomenon was also described in acute patients with ITP treated with plasmapheresis. The majority of patients who responded to efgartigimod had a transient increase in platelet counts, with counts returning to baseline levels in the treatment-free FU period. Two newly diagnosed ITP patients and 1 chronic ITP patient maintained an increased platelet count throughout the extended FU period (up to day 162). Similar observations were made for "acute" patients with ITP following plasmapheresis, but responses for chronic patients were solely reported to be transient.

Encouragingly in subgroup analyses based on ITP classification (newly diagnosed, persistent or chronic ITP), concomitant ITP treatment or use of TPO-RA, there were examples of efgartigimod-treated patients with apparent efficacy based on an increase in platelet count. Nevertheless, as anticipated in a study with limited number of patients, there were no clear differences in each of these subcategories.

In the OLE period, 12 patients received efgartigimod 10 mg/kg, including 4 patients from the placebo group in the randomized study. The results obtained demonstrated the repeatability of the efgartigimod-induced platelet increases as 3 patients in the efgartigimod 10 mg/kg group who had achieved platelet count $\geq 50 \times 10^9$/L on at least 2 occasions during the randomized period, achieved this threshold again in the OLE period. Interestingly, the 2 patients initially treated with efgartigimod 5 mg/kg who did not show an increase in platelet count, did so when treated with efgartigimod 10 mg/kg in the OLE period, suggesting the need for the higher dose or longer exposure to efgartigimod (Table 3).

The observation that efgartigimod induces an increased platelet count in patients with ITP predominantly refractory to previous lines of ITP therapy, regardless of prior use of ITP therapies (e.g. steroids, rituximab. TPO-RA, splenectomy), supports the central role of pathogenic IgGs in ITP and potential utility of IgG depletion. Patients benefited at both doses tested, further supporting the IgG reduction hypothesis. There were some signals that the 10 mg/kg dose may be superior, including the facts that there were no newly diagnosed patients in this group, 2 patients in the main study did not receive all four 10 mg/kg doses, and 2 patients whose platelet counts did not increase with efgartigimod 5 mg/kg in the main study, did increase upon treatment with efgartigimod 10 mg/kg in the OLE period (Table 3). Additionally, there was a decreased incidence of bleeding, measured using the bleeding scales (total WHO and ITP-BAT scores >0), in both efgartigimod-treated groups, with numerically greater reduction in the efgartigimod 10 mg/kg group.

Example 6: Open-Label Extension Period

Any evaluable patient who relapsed on their current SoC while participating in the main study described in Example 5 was given the option to enter the open-label extension period of the study to further explore the safety and tolerability, efficacy, and PK/PD of efgartigimod. During the main study follow-up period (i.e., the 8-week follow-up period plus the 13-week extended follow-up period), a relapse was characterized as a patient platelet count that decreased below $30\times10^9$/L with the absence of bleeding, or a patient platelet count that never reached $30\times10^9$/L with the absence of bleeding. FIG. 2 shows the design of the open-label extension study. Endpoint assessments were performed according to the Schedule of Assessments as detailed in Table 4 and Table 5.

TABLE 4

Schedule of assessments: Open-label treatment period—first treatment cycle.

| Assessments | Treatment Evaluation Visit[a] | Treatment Period | | | | | | | Follow-Up Period | | | | | Safety Visit | FU until next Relapse[q] |
|---|---|---|---|---|---|---|---|---|---|---|---|---|---|---|---|
| Visits | | V17 | V18 | V19 | V20 | V21 | V22 | V23 | V24 | V25 | V26 | V27 | V28 | | |
| Study Day* | | 1 | 4 ± 1 | 8 ± 1 | 11 ± 1 | 15 ± 1 | 18 ± 1 EoT | 22 ± 1 | 25 ± 1 | 29 ± 1 | 36 ± 1 | 64 ± 1 | 78 ± 3 (EoC)/ED[r] | US | EoC[q] |
| | | | | | | | | | | Weeks post last infusion | | | | | |
| | | | | | | | | | | 2 | 4[m] | 6[m] | 8[m] | | |
| Informed consent[b] | X | | | | | | | | | | | | | | |
| Eligibility/exclusion criteria | X[b] | X | | | | | | | | | | | | | |
| Additional Medical/surgical history | X | | | | | | | | | | | | | | |
| Vital signs | X | X | | X | | X | | X | | X | | X | X | | |
| Physical examination including height, weight[c] | X | X | | X | | X | | X | | X | X | X | X | | |
| General Bleeding Assessment (WHO and SMOG) | X | X | | X | | X | | X | | X | X | X | X | | X[o] |
| SF-36 and FACT-Th6[d] | X | X | | | | | | | | X | | X | X | | |
| Hematology and chemistry tests[g,m] | X[m] | X | | X | | X | | | | X | | X | X | X | |
| Platelet counts | X[f] | X[l] | X | X[l] | X | X[l] | X | X | X | X[l] | X | X[l] | X[l] | | X[n] |
| ECG | X | X | | | | | | X[p] | | X | | | X | X | |
| Urinalysis | X | X | | | | | | | | | | | X | X | |
| Pharmacokinetics | | X[k] | | X[k] | | X[k] | | X[k] | | X | X | X | | | |
| Pharmacodynamics[h] | | X | | X | | X | | X | | X | X | X | X | | |
| Antiplatelet antibodies and IgG | | | | | | | | | | | | | | | |
| Antidrug antibodies | | X | | | | | | X | | | | X | | | |
| Urine Pregnancy test | X | X | | | | | | | | | | X | | | |
| Administration of IMP[e] | | X[i] | | X[i] | | X[i] | | X[i] | | | | | | | |
| Concomitant therapies/procedures[j] | | | | | | | | | | | | | | | |
| AEs[j] | | | | | | | | | | | | | | | |

Abbreviations:
AEs = adverse events;
ED = early discontinuation;
EoC = end of cycle;
EoS = end of study;
EoT = end of treatment;
FACT-Th6 = Functional Assessment of Cancer Therapy Questionnaire-ThC;?
ICF = informed consent form;
IgG = immunoglobulin G;
G; IMP = investigational medicinal product;
SMOG/ITP-BAT = immune thrombocytopenia-bleeding assessment tool;
SAE = serious adverse event;
SF-36 = Short Form-36;?
US = unscheduled visit;
WHO = World Health Organization.?

*The allowed window period between visits in Treatment period and Follow-up period is ±1 day provided that 2 consecutive visits are 3 days apart at a minimum. Every effort should be made to schedule every visit on the exact Day (which is relative to Visit 17) as described in above Schedule of Assessments without the window.?
[a]If procedures listed for the EoS visit (Visit 16) in Table 2 were performed within one week before the first administration of ARGX-113 10 mg/kg in the open label treatment phase those procedures were not repeated in the Treatment Evaluation Visit. ARGX-113 could only be administered if the patient agreed to take part in the open-label treatment period of the study and signed the ICF?
[b]The specific ICF for the open-label treatment period had to be signed prior to assessment of the inclusion and exclusion criteria for confirmation of eligibility of the patient to the open-label treatment period.?
[c]Height was measured at Treatment Evaluation Visit (and Body Mass Index calculated accordingly). Weight was recorded at Treatment Evaluation Visit and before each administration of IMP (as IMP depends on patient weight).?
[d]Patient reported outcome assessments were mandatory to be performed before any other assessments at the visit.?
[e]Assessments was completed pre-dose on all study drug infusion days.?
[f]To determine eligibility of patients, platelet counts were performed during Treatment Evaluation Visit or was performed during EoS (Visit 16).?
[g]Hematology and blood chemistry included all of clinical chemistry (sodium, potassium, chloride, glucose, bicarbonate, creatinine, blood urea nitrogen, alanine transaminase, AST, total bilirubin, gamma-GT, CRP, AP, lactate dehydrogenase, uric acid, total protein, and albumin), hematology (hemoglobin, hematocrit, mean corpuscular volume, mean corpuscular hemoglobin, mean corpuscular hemoglobin concentration, red blood cell count, platelet count, white blood cell count with differential), and urinalysis (abnormal blood on dipstick).?

TABLE 4-continued

Schedule of assessments: Open-label treatment period—first treatment cycle.

[h]Total IgG, antiplatelet antibodies. Pharmacodynamic samples were collected pre-dose on all dosing days. Antiplatelet antibodies were measured with a validated assay (Visits 17, 25 and 28)?
[i]Investigational medicinal product was administered as an IV infusion over a period of 2 hours at Visits 17, 19, 21, and 23, Patient was monitored in-house for at least 2 hours postinfusion.?
[j]Adverse events, intake of concomitant medication(s) and new procedure were monitored continuously from signing the ICF until the last study-related activity. In case of early discontinuation, any AEs/SAEs were assessed for 30 days following the Early Discontinuation visit or until satisfactory resolution or stabilization.?
[k]PK assessments were done both pre- and post-dose (within 30 minutes prior to start of infusion for pre-dose sample and within 30 minutes after end of infusion for post-dose sample) on all IMP infusion days.?
[l]At these visits, platelet counts were obtained as part of the hematology tests.?
[m]If the patient relapsed between Visit 26 and Visit 28, those visits were considered EoC visit and/or treatment evaluation visit for next cycle,?
[n]Extended FU period: platelet counts from local laboratory, WHO bleeding scale and rescue medication will be collected retrospectively/prospectively from the patient's medical file.?
[o]Only WHO bleeding scale if available in the patient's medical file will be reported.?
[p]At Visit 23, the ECG was taken post-infusion.?
[q]End of cycle visit for the first open-label treatment cycle was considered the visit at which relapse was observed and rescue treatment given.?
[r]If the patient relapsed between Visit 26 and Visit 28, those visits were considered EoC visit andlor treatment evaluation visit for next cycle.?

TABLE 5

Schedule of assessments: Open-label treatment period—subsequent treatment cycle(s).

| Assessments | Retreatment Evaluation | Treatment Period | | | | Follow-Up Period | | | | Safety | Extended FU until next relapse/end |
|---|---|---|---|---|---|---|---|---|---|---|---|
| Visits | Visit* | V29** | V30 | V31 | V32 | V33 | V34 | V35 | V36 | Visit | of Month 12 |
| Study Day*** | | 1 | 8 ± 1 | 15 ± 1 | 22 ± 1 EoT | 36 ± 1 | 50 ± 1 | 64 ± 1 | 78 ± 3 (EoC)/ED | US | EoC/EoS[l] |
| | | | | | | Weeks post last infusion | | | | | |
| | | | | | | 2 | 4 | 6 | 8 | | |
| Vital signs | X | X | X | X | X | X | X | X | X | X | |
| Physical examination including height, weight[a] | X | X | X | X | X | X | X | X | X | X | |
| General Bleeding Assessment (WHO and SMOG) | X | X | X | X | X | X | X | X | X | | X[k] |
| SF-36 and FACT-Th6[c] | X | X | | | | X | | X | X | | |
| Hematology and chemistry Tests[b, e] | X | X | X | X | X | X | X | X | X | X | |
| Platelet counts | X[g] | X[g] | X[g] | X[g] | X[g] | X[g] | X[g] | X[g] | X[g] | | X[j] |
| Urinalysis | X | X | | | | | | | X | X | |
| ECG | | X[b] | | | X[b] | | | | | | |
| Pharmacodynamics | | X | | | | X | | X | | | |
| Antiplatelet antibodies and IgG[f] | | X | | | | | | | | | |
| Antidrug antibodies | | X | | | X | | | | X | | |
| Urine Pregnancy test | | X | | | | | | | | | |
| Administration of IMP[d,h] | | X | X | X | X | | | | | | |
| Concomitant therapies/ procedures AEs[i] | | | | | | | | | | | |

Abbreviations:
AEs = adverse events;
ED = early discontinuation;
EoC = end of cycle;
EoS = end of study;
EoT = end of treatment;
FACT-Th6 = Functional Assessment of Cancer Therapy Questionnaire-Th6;
IMP = investigational medicinal product;
SMOG/ITP-BAT = immune thrombocytopenia-bleeding assessment tool;
SAE = serious adverse event;
SF-36 = Short Form-36;
US = unscheduled visit;
WHO = World Health Organization.
*The time window between 2 consecutive (re)treatment cycles was at least 4 weeks of FU. If patient relapsed between V34 and V36, those visits were considered EoC visit and/or treatment evaluation visit for next cycle. In case of retreatment, the EoC visit in the extended follow-up period from a cycle could be combined with the treatment evaluation visit of a subsequent cycle.
**The last retreatment cycle started not later than the first half of the 10th month of the open-label treatment period. The duration of the open-label treatment period was up to maximum 12 months from signing the ICF for the open-label treatment period.
***The allowed window period between visits in Treatment period and Follow-up period is ±1 day. Every effort was made to schedule every visit on the exact Day (which is relative to the Visit 29) as described in above Schedule of Assessments without the window.
[a]Height was measured at Retreatment Evaluation Visit (and Body Mass Index calculated accordingly). Weight was recorded before each administration of IMP (as IMP depends on patient weight).
[b]At Visit 29, the ECG was taken pre-infusion. At Visit 32, the ECG was taken post-infusion.
[c]Patient reported outcome assessments were mandatory to be performed before any other assessments at the visit.
[d]Assessments were completed pre-dose on all study drug infusion days.

TABLE 5-continued

Schedule of assessments: Open-label treatment period—subsequent treatment cycle(s).

| Assessments | Retreatment Evaluation | Treatment Period | | | | Follow-Up Period | | | | Safety | Extended FU until next relapse/end |
|---|---|---|---|---|---|---|---|---|---|---|---|
| Visits | Visit* | V29** | V30 | V31 | V32 | V33 | V34 | V35 | V36 | Visit | of Month 12 |
| Study Day*** | | 1 | 8 ± 1 | 15 ± 1 | 22 ± 1 EoT | 36 ± 1 | 50 ± 1 | 64 ± 1 | 78 ± 3 (EoC)/ED | US | EoC/EoS$^l$ |
| | | | | | | Weeks post last infusion | | | | | |
| | | | | | | 2 | 4 | 6 | 8 | | |

$^e$Hematology and blood chemistry included all of clinical chemistry (sodium, potassium, chloride, glucose, bicarbonate, creatinine, blood urea nitrogen, alanine transaminase, AST, total bilirubin, gamma-GT, CRP, AP, lactate dehydrogenase, uric acid, total protein, and albumin), hematology (hemoglobin, hematocrit, mean corpuscular volume, mean corpuscular hemoglobin, mean corpuscular hemoglobin concentration, red blood cell count, platelet count, white blood cell count with differential), and urinalysis (abnormal blood on dipstick).
$^f$Total IgG, antiplatelet antibodies. Pharmacodynamic samples were collected pre-dose on the dosing day. Antiplatelet antibodies were measured with a validated assay (Visit 29 and Visit 36).
$^g$At these visits, platelet counts were obtained as part of the hematology tests.
$^h$Investigational medicinal product was administered as an IV infusion over a period of 2 hours at Visits 29, 30, 31, and 32, Patient was monitored in-house for at least 2 hours postinfusion.
$^i$Adverse events, intake of concomitant medication(s) and new procedure was monitored continuously from signing the ICF until the last study-related activity. In case of early discontinuation, any AEs/SAEs were assessed for 30 days following the Early Discontinuation visit or until satisfactory resolution or stabilization.
$^j$Extended FU period: platelet counts from local laboratory and rescue medication were collected retrospectively/prospectively from the patient's medical file.?
$^k$Only WHO bleeding scale if available in the patient's medical file will be reported.
$^l$End of cycle visit for the open-label treatment period was considered the visit at which relapse was observed and rescue treatment given. If relapse occurred within 4 weeks after the treatment period the patient could not be considered for a next treatment cycle. In case no relapse occurred, the nearest visit before the end of the 12-month open-label treatment period was considered the End of Study visit.

As shown in FIG. 2, the open-label extension period of the Phase 2 study extended for a maximum of 1 year. Each patient received efgartigimod at a dose of 10 mg/kg b.w. in cycles of 4 weekly IV infusions (i.e., 4 doses over 3 weeks in addition to SoC), with a minimum of 4 weeks separating individual treatment cycles. During open-label treatment, no changes in the dose administration and frequency of efgartigimod or the SoC were allowed. However, during the follow-up period, tapering of the SoC by a level of 25% was permitted at the discretion of the investigator, when deemed medically needed and only in patients who achieved complete response.

The first open-label extension cycle included a 1-week treatment evaluation visit, a 3-week open-label treatment period (Visit 17 through Visit 23), and a 4-week minimum follow-up period (Visit 24 through Visit 28). Short safety evaluation visits were scheduled between two of the treatment visits. The allowed window between visits in the first open-label treatment period and the follow-up period was ±1 day, provided that the two consecutive visits were at least 3 days apart. Every effort was made to schedule each visit on the same day (relative to Visit 17) as described in Table 4.

Each subsequent retreatment cycle included a 1-week retreatment evaluation visit, a 3-week open-label treatment period (e.g., Visit 29 through Visit 32), and 4-week minimum follow-up period (e.g., Visit 33 through Visit 36). The allowed window between visits in each open-label treatment period and the follow-up period was ±1 day. Every effort was made to schedule each visit on the same day (e.g., relative to the Visit 29) as described in Table 5.

The time window between consecutive (re)treatment cycles was a minimum of 4 weeks. For each (re)treatment cycle, the 4-week follow-up period could be extended by a flexible follow-up period. Information collected from daily practice included, e.g., platelet counts, rescue treatment, bleeding events, and any serious adverse events, until relapse and/or administration of the next treatment for ITP.

Results

A total of 12 patients from the three treatment arms of the main study were treated during the open-label period. Several patients with low platelet counts (e.g., less than $15 \times 10^9$/L) achieved platelet counts in excess of $50 \times 10^9$/L or $100 \times 10^9$/L in response to treatment during the open-label extension. Notably, one patient from the 5 mg/kg efgartigimod treatment arm achieved a platelet count of approximately $80 \times 10^9$/L during the open-label extension, despite never having achieved platelet counts in excess of $30 \times 10^9$/L throughout the entire duration of the main study.

Example 7. Phase 3 Clinical Trial of Efgartigimod in Humans with Primary ITP

This example describes a phase 3, multicenter, randomized, double-blinded, placebo-controlled, up to 30-week trial to evaluate the efficacy and safety of efgartigimod (ARGX-113) 10 mg/kg intravenous in adult patients with primary immune thrombocytopenia (ITP). The primary objective of this trial is to evaluate the efficacy of efgartigimod compared to placebo in achieving a sustained platelet count response in patients with chronic primary ITP, with a sustained platelet count response defined as platelet counts of at least $50 \times 10^9$/L for at least 4 of the 6 visits between visits 19 and 24 of the trial. Secondary objectives include evaluation of the efficacy of efgartigimod compared to placebo in overall platelet count response; evaluation of the safety and tolerability of efgartigimod administered intravenously (IV) weekly or biweekly; evaluation of the incidence and severity of bleeding events while receiving treatment with efgartigimod compared to placebo; evaluation of the use of rescue treatment and changes in concurrent ITP therapy while receiving treatment with efgartigimod compared to placebo; evaluation of the effects of efgartigimod treatment on quality-of-life (QoL) measures and patient-reported outcomes (PRO) compared to placebo; assessment of the immunogenicity of efgartigimod; assessment of the pharmacokinetics (PK) of efgartigimod: and assessment of the pharmacodynamic (PD) effects of efgartigimod.

The target population are adult patients with persistent or chronic primary ITP, having an average platelet count of $<30 \times 10^9$/L and having previously received at least 1 ITP therapy. If patients are receiving concurrent ITP therapies at baseline, these therapies are maintained at a stable dose and dosing frequency for 4 weeks prior to randomization. As of week 12, an increase in dose and/or schedule of permitted concurrent ITP therapy is allowed for the patients who have an "insufficient" response (i.e., no platelet count of ≥30× $10^9$/L in any of the visits during the last 4 weeks). These patients are considered as "non-responders" for the primary endpoint analysis.

After confirmation of eligibility, the patients enter a 24-week treatment period and are randomized to receive efgartigimod 10 mg/kg IV or placebo, weekly from visits 1 to 4 and then from visits 5 to 16 either weekly or biweekly, adjusted according to their platelet counts. From visits 17 to 24, patients are fixed on the dosing schedule they are receiving at visit 16 (i.e. either weekly or biweekly).

Patients completing the 24-week randomized trial period are eligible to enter an open-label extension trial to receive efgartigimod 10 mg/kg IV according to the frequency they were receiving at the time of leaving the main trial (i.e. weekly or biweekly).

Approximately 117 patients with chronic ITP and up to 39 patients with persistent ITP are randomized in a 2:1 ratio to receive efgartigimod or placebo, respectively. All eligible patients are randomized to receive IV infusions of either efgartigimod 10 mg/kg body weight or matching placebo throughout the trial. All patients initially receive weekly IV infusions from visits 1 to 4. Based on the platelet counts as of visit 2, the dosing frequency can be altered from visits 5 to 16 according to following rules (the change in dosing frequency will occur at the current visit): (i) reduce from weekly to biweekly in patients achieving platelet counts of ≥100×$10^9$/L for 3 out of 4 consecutive visits (the $4^{th}$ visit being the current visit) and have a platelet count of ≥100× $10^9$/L at the last of these 4 visits, or 3 consecutive visits; or (ii) increase from biweekly to weekly in patients whose platelet counts drop below 100×$10^9$/L on 2 consecutive visits, or <30×$10^9$/L at 1 visit, or in patients who receive rescue therapy.

Patients receiving permitted concurrent ITP therapy are eligible for the trial, if the dose and schedule remain unchanged in the last 4 weeks before randomization (i.e., visit 1). Permitted concurrent ITP medications include oral corticosteroids, oral immunosuppressants, dapsone/danazol, and/or eltrombopag. Dose and frequency of permitted concurrent ITP therapies remain unchanged during the trial. The only exceptions are patients who are receiving concurrent treatment with the thrombopoietin receptor agonist (TPO-RA) eltrombopag in whom dose reduction of eltrombopag is permitted at label-defined platelet thresholds.

Patients not receiving concurrent ITP therapy are also eligible for the trial.

Patients randomized to receive efgartigimod are administered 10 mg efgartigimod/kg body weight as IV infusion over a period of 1 hour at infusion visits. The maximum total dose per infusion is 1,200 mg for patients with body weight ≥120 kg measured at infusion visits. Patients randomized to receive placebo are administered matching placebo with the same excipients as the efgartigimod, but without efgartigimod, as an IV infusion over a period of 1 hour at infusion visits.

Figure 14:
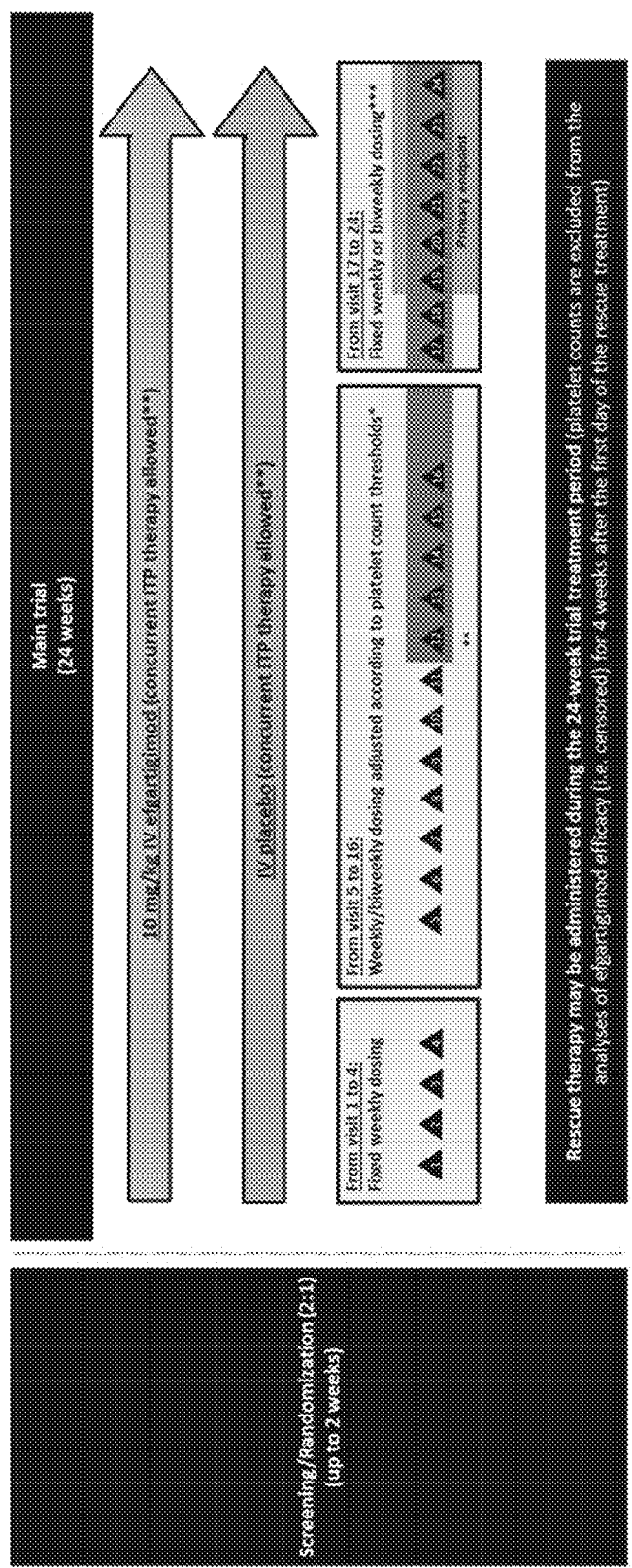
FIG. 14 depicts the design of the Phase 3 clinical trial described in Example 7.

FIG. 14 depicts the general design of this study.

Results of this study confirm that efgartigimod dosed at 10 mg/kg body weight is effective compared to placebo in achieving a sustained platelet count response in patients with chronic primary ITP, with a sustained platelet count response defined as platelet counts of at least 50×$10^9$/L for at least 4 of the 6 visits between visits 19 and 24 of the trial.

Example 8. Comparison with Rozanolixizumab

Results of a Phase 2 study of anti-FcRn monoclonal antibody rozanolixizumab (UCB7665) were recently reported. Robak T et al., *Blood* 130: 15 (2017). In that study 30 adult patients with chronic or persistent ITP were treated with multiple doses of rozanolixizumab, either 5 weekly doses of 4 mg/kg administered subcutaneously (s.c.) or 3 weekly doses of 7 mg/kg s.c. Unlike in the Phase 2 trial of efgartigimod (ARGX-113) described herein, in the rozanolixizumab study a high variability in pharmacodynamic effects, as measured by mean decrease in total IgG, was observed. For example, whereas the ranges of maximal IgG reduction with 4 and 7 mg/kg rozanolixizumab were 29.9-65% and 29.5-65.5%, respectively, the ranges of maximal IgG reduction with 5 and 10 mg/kg efgartigimod were 48-81% and 46-72%, respectively. In both studies, in many patients a response was lost within a month of the last dose. However, unlike in the rozanolixizumab study, patients in the Phase 2 trial of efgartigimod described herein included patients with responses lasting longer than 30 days, and some had long-term response. This prolonged response observed with efgartigimod was surprising given the relatively short treatment period and the results reported in the rozanolixizumab study.

Example 9. Treatment of ITP Using Affibody or Affibody Derivative

An affibody specific for human FcRn is expressed alone (MW ca. 6.5 kDa) or as a fusion protein with either an albumin binding domain (ABD; fusion protein MW ca. 19 kDa, see Seijsing et al. (2014) Proc Natl Acad Sci USA 111(48): 17110-17115; Seijsing et al. (2018) Sci Rep. 8(1): 5141: WO 2014/140366) or human albumin (fusion protein MW ca. 73 kDa). In an embodiment, the affibody (and either fusion protein) has a high affinity for FcRn at pH 6.0 and a lower affinity for FcRn at pH 7.4. In another embodiment, the affibody (and either fusion protein) has a high affinity for FcRn both at pH 6.0 and at pH 7.4. The ABD is an engineered, independently folding domain that can interact with high affinity with serum albumin in blood. The ABD does not affect serum albumin interaction with its binding site on FcRn, which in turn is distinct from the binding site of IgG and affibody interaction with FcRn.

The affibody, affibody fusion protein(s), or irrelevant control is administered intravenously to mice once daily for 7-14 days, beginning on day 1. Serum total IgG is measured before the first dose and then pre-dose every other day beginning on day 4 (e.g., days 4, 6, 8, 10, 12, 14, 16, 18, and 20). Given the differences in MW, each dose of affibody alone is approximately 3 times greater (mass/kg body weight) than that of the affibody-ABD fusion protein. Alternatively or in addition, each dose of affibody-ABD fusion protein is approximately 4 times greater (mass/kg body weight) than that of the affibody-albumin fusion protein, at least approximately 3.5 times greater than that of albumin, or at least approximately 2.5 times greater than that of Fc fragment variant, e.g., efgartigimod.

In an embodiment, an affibody-ABD fusion protein comprises the amino acid sequence set forth as SEQ ID NO: 4:

(SEQ ID NO: 4)
AEAKFAKEWQQAAHEIRWLPNLTFDQRVAFIHKLRDDPSQSSELLSEAKK

LSESQAPKASGSLAEAKEAANAELDSYGVSDFYKRLIDKAKTVEGVEALK

DAILAALPGTGGGGSAEAKFAKEWQQAAHEIRWLPNLTFDQRVAFIHKLR

DDPSQSSELLSEAKKLSESQAPK where the C-terminal 58 amino acids correspond to the affibody, and the ABD and the affibody are joined by a 5-amino acid Gly-Ser linker.

Treatment with affibody alone, affibody-ABD fusion protein, or affibody-albumin fusion protein effectively reduces serum total IgG, suggesting that these agents can be used to treat ITP in humans.

INCORPORATION BY REFERENCE

All patent and non-patent literature references cited herein are incorporated herein by reference in their entirety.

EQUIVALENTS

Many modifications in addition to those described above may be made to the structures and techniques described herein without departing from the spirit and scope of the invention. Accordingly, although specific embodiments have been described, these are examples only and are not limiting upon the scope of the invention.

The invention claimed is:

1. A method of treating a human subject that has newly diagnosed, persistent, or chronic immune thrombocytopenia (ITP), the method comprising administering to the subject a human neonatal Fc receptor (hFcRn) antagonist, wherein the hFcRn antagonist is administered intravenously once weekly at a dose of about 5 mg/kg to about 10 mg/kg at least four times, wherein the hFcRn antagonist consists of a variant Fc region consisting of two Fc domains which form a homodimer, wherein the amino acid sequence of each of the Fc domains consists of SEQ ID NO: 1, SEQ ID NO: 2, or SEQ ID NO: 3, wherein the human subject has a platelet count of ≤30×10$^9$/L on standard-of-care treatment with at least one compound approved for standard-of-care treatment for ITP prior to administering the hFcRn antagonist, and wherein the subject achieves a platelet count of >50×10$^9$/L after administering four doses of the hFcRn antagonist, thereby treating the subject.

2. The method of claim 1, wherein the hFcRn antagonist is efgartigimod.

3. The method of claim 2, wherein the efgartigimod is administered intravenously at a dose dosage of about 5 mg/kg or about 10 mg/kg.

4. The method of claim 1, wherein the human subject has a platelet count of less than 30×10$^9$/L prior to administering the hFcRn antagonist.

5. The method of claim 1, wherein the human subject receives one or more doses of at least one compound approved for standard-of-care treatment for ITP.

6. The method of claim 1, wherein the human subject has persistent or chronic ITP.

7. The method of claim 5, wherein the compound approved for standard-of-care treatment for ITP is selected from the group consisting of corticosteroids, romiplostim, eltrombopag, avatrombopag, cyclosporine, dapsone, danazol, azathioprine, intravenous immunoglobulin (IVIg), Rho (D) immune globulin (anti-D), rituximab, fostamatinib, and alemtuzumab.

8. The method of claim 1, wherein the human subject has chronic ITP.

9. The method of claim 2, wherein the efgartigimod is administered intravenously at a dose of about 10 mg/kg.

10. The method of claim 9, wherein the efgartigimod is administered intravenously at a dose of about 10 mg/kg every two weeks after administering the first four doses.

11. The method of claim 5, wherein the at least one compound approved for standard-of-care treatment for ITP is administered prior to administering one or more doses of the hFcRn antagonist.

12. The method of claim 7, wherein the corticosteroid is selected from the group consisting of prednisone, methylprednisolone, and dexamethasone.

13. The method of claim 1, wherein the human subject achieves a platelet count of >50×10$^9$/L for at least 4 weeks.

14. The method of claim 1, wherein the human subject achieves a platelet count of >50×10$^9$/L for at least 4 of 6 consecutive weeks.

* * * * *

UNITED STATES PATENT AND TRADEMARK OFFICE
CERTIFICATE OF CORRECTION

| | | |
|---|---|---|
| PATENT NO. | : 12,202,900 B2 | Page 1 of 1 |
| APPLICATION NO. | : 16/435166 | |
| DATED | : January 21, 2025 | |
| INVENTOR(S) | : De Haard et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 710 days.

Signed and Sealed this
Fifth Day of August, 2025

Coke Morgan Stewart
*Acting Director of the United States Patent and Trademark Office*

SEQUENCE LISTING

```
<160> NUMBER OF SEQ ID NOS: 4

<210> SEQ ID NO 1
<211> LENGTH: 226
<212> TYPE: PRT
<213> ORGANISM: Artificial sequence
<220> FEATURE:
<223> OTHER INFORMATION: Synthetic polypeptide

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu Lys Phe His Tyr Thr Gln Lys Ser Leu Ser Leu Ser
        210                 215                 220

Pro Gly
225
```

```
<210> SEQ ID NO 2
<211> LENGTH: 227
<212> TYPE: PRT
<213> ORGANISM: Artificial sequence
<220> FEATURE:
<223> OTHER INFORMATION: Synthetic polypeptide

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly Lys
225

<210> SEQ ID NO 3
<211> LENGTH: 231
<212> TYPE: PRT
<213> ORGANISM: Artificial sequence
<220> FEATURE:
<223> OTHER INFORMATION: Synthetic polypeptide

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu Lys Phe His Tyr Thr Gln Lys Ser Leu Ser Leu Ser
    210                 215                 220
Pro Asp Ser Asn Leu Trp Asn
225                 230

<210> SEQ ID NO 4
<211> LENGTH: 173
<212> TYPE: PRT
<213> ORGANISM: Artificial sequence
<220> FEATURE:
<223> OTHER INFORMATION: Synthetic polypeptide

<400> SEQUENCE: 4

Ala Glu Ala Lys Phe Ala Lys Glu Trp Gln Gln Ala Ala His Glu Ile
1               5                   10                  15
Arg Trp Leu Pro Asn Leu Thr Phe Asp Gln Arg Val Ala Phe Ile His
            20                  25                  30
Lys Leu Arg Asp Asp Pro Ser Gln Ser Ser Glu Leu Leu Ser Glu Ala
        35                  40                  45
Lys Lys Leu Ser Glu Ser Gln Ala Pro Lys Ala Ser Gly Ser Leu Ala
    50                  55                  60
Glu Ala Lys Glu Ala Ala Asn Ala Glu Leu Asp Ser Tyr Gly Val Ser
65                  70                  75                  80
Asp Phe Tyr Lys Arg Leu Ile Asp Lys Ala Lys Thr Val Glu Gly Val
                85                  90                  95
Glu Ala Leu Lys Asp Ala Ile Leu Ala Ala Leu Pro Gly Thr Gly Gly
            100                 105                 110
Gly Gly Ser Ala Glu Ala Lys Phe Ala Lys Glu Trp Gln Gln Ala Ala
        115                 120                 125
His Glu Ile Arg Trp Leu Pro Asn Leu Thr Phe Asp Gln Arg Val Ala
    130                 135                 140
Phe Ile His Lys Leu Arg Asp Asp Pro Ser Gln Ser Ser Glu Leu Leu
145                 150                 155                 160
Ser Glu Ala Lys Lys Leu Ser Glu Ser Gln Ala Pro Lys
                165                 170
```